United States Patent
Myers et al.

(10) Patent No.: US 11,781,176 B2
(45) Date of Patent: Oct. 10, 2023

(54) METHOD FOR BLOCKING MIRNA

(71) Applicant: HudsonAlpha Institute for Biotechnology, Huntsville, AL (US)

(72) Inventors: Richard M Myers, Huntsville, AL (US); Brian S Roberts, Huntsville, AL (US)

(73) Assignee: HudsonAlpha Institute for Biotechnology, Huntsville, AL (US)

( * ) Notice: Subject to any disclaimer, the term of this patent is extended or adjusted under 35 U.S.C. 154(b) by 762 days.

(21) Appl. No.: 16/581,129

(22) Filed: Sep. 24, 2019

(65) Prior Publication Data

US 2020/0024652 A1 Jan. 23, 2020

Related U.S. Application Data

(62) Division of application No. 15/565,652, filed as application No. PCT/US2016/026846 on Apr. 10, 2016, now Pat. No. 10,480,023.

(60) Provisional application No. 62/146,015, filed on Apr. 10, 2015.

(51) Int. Cl.
| | | |
|---|---|---|
| C12Q 1/6848 | (2018.01) | |
| C12Q 1/6806 | (2018.01) | |
| C12Q 1/686 | (2018.01) | |
| C12N 15/11 | (2006.01) | |
| C12N 15/113 | (2010.01) | |
| C12Q 1/6874 | (2018.01) | |

(52) U.S. Cl.
CPC ............ *C12Q 1/6848* (2013.01); *C12N 15/11* (2013.01); *C12N 15/111* (2013.01); *C12N 15/113* (2013.01); *C12Q 1/6806* (2013.01); *C12Q 1/686* (2013.01); *C12Q 1/6874* (2013.01); *C12N 2310/113* (2013.01); *C12N 2320/10* (2013.01); *C12N 2330/31* (2013.01); *C12Q 2521/501* (2013.01); *C12Q 2525/186* (2013.01); *C12Q 2525/191* (2013.01); *C12Q 2525/207* (2013.01); *C12Q 2525/301* (2013.01); *C12Q 2537/163* (2013.01)

(58) Field of Classification Search
CPC .... C12Q 1/6848; C12Q 1/6806; C12Q 1/686; C12Q 2521/301; C12Q 2525/186; C12Q 2525/191; C12Q 2525/207; C12Q 2525/301; C12Q 2537/163
See application file for complete search history.

(56) References Cited

U.S. PATENT DOCUMENTS

| | | |
|---|---|---|
| 2004/0014105 A1 | 1/2004 | Schroeder |
| 2013/0287772 A1 | 10/2013 | Halbert |
| 2015/0105275 A1 | 4/2015 | Wong |

OTHER PUBLICATIONS

Roberts et al. Blocking of targeted microRNAs from next-generation sequencing libraries. Nucleic Acids Research 2015; 43: e145 (Year: 2015).*
Hafner et al. Identification of microRNAs and other small regulatory RNAs using cDNA library sequencing. Methods 2008; 44: 3-12 (Year: 2008).*
Chen et al. Real-time quantification of microRNAs by stem-loop RT-PCR. Nucleic Acids Research 2005; 33: e179 (Year: 2005).*
Wickersheim et al. Terminator oligo blocking efficiently eliminates rRNA from *Drosophila* small RNA sequencing libraries. BioTechniques 2013; 55: 269-272 (Year: 2013).*
Zhou et al. Rare allele enrichment and detection by allele-specific PCR, competitive probe blocking, and melting analysis. BioTechniques 2011; 50: 311-318 (Year: 2011).*
Examiner Rie Kawai "Office Action issued in co-pending Japanese patent application No. 2017-55315"—Japanese Patent Office; dated Jan. 24, 2020; pp. 1-3.

* cited by examiner

*Primary Examiner* — Angela M. Bertagna
(74) *Attorney, Agent, or Firm* — Bradley Arant Boult Cummings LLP; Aaron Chaloner

(57) ABSTRACT

A method of reducing the abundance of a non-target microRNA (miRNA) that is part of a group of miRNAs is provided, including: (a) annealing a complementary region of a blocking nucleic acid to a binding site at a first end of the unwanted miRNA, ligating an adenylated nucleic acid adapter to the group of miRNAs, and performing RT-PCR on group of miRNAs. Kits and compounds for use with the method are also provided.

15 Claims, 29 Drawing Sheets

Specification includes a Sequence Listing.

hsa-miR-16-5p  UAGCAGCACGUAAAUAUUGGCG  SEQ ID NO: 6
hsa-miR-15a-5p UAGCAGCACAUAAUCGUUUGUG SEQ ID NO: 7
hsa-miR-15b-5p UAGCAGCACAUCAUGGUUUACA SEQ ID NO: 8
hsa-miR-195-5p UAGCAGCACAGAAAUAUUGGC  SEQ ID NO: 9
hsa-miR-424-5p CAGCAGCAAUUCAUGUUUUGAA SEQ ID NO: 10
hsa-miR-497-5p CAGCAGCACACUGUGGUUUGU  SEQ ID NO: 11

SEQUENCE LISTING

<160> NUMBER OF SEQ ID NOS: 13

<210> SEQ ID NO 1
<211> LENGTH: 58
<212> TYPE: DNA
<213> ORGANISM: Artificial Sequence
<220> FEATURE:
<223> OTHER INFORMATION: Blocking nucleic acid

<400> SEQUENCE: 1
ctcagtacag gacgtactct ggactctagt cagtagcacg actagagtcc agagtacg    58

<210> SEQ ID NO 2
<211> LENGTH: 58
<212> TYPE: DNA
<213> ORGANISM: artificial sequence
<220> FEATURE:
<223> OTHER INFORMATION: Blocking nucleic acid

<400> SEQUENCE: 2
ggattacttg aacgtactct ggactctagt cagtagcacg actagagtcc agagtacg    58

<210> SEQ ID NO 3
<211> LENGTH: 58
<212> TYPE: DNA
<213> ORGANISM: artificial sequence
<220> FEATURE:
<223> OTHER INFORMATION: Blocking nucleic acid

<400> SEQUENCE: 3
tggtaacggt ttcgtactct ggactctagt cagtagcacg actagagtcc agagtacg    58

<210> SEQ ID NO 4
<211> LENGTH: 58
<212> TYPE: DNA
<213> ORGANISM: artificial sequence
<220> FEATURE:
<223> OTHER INFORMATION: Blocking nucleic acid

<400> SEQUENCE: 4
tacgtgctgc tacgtactct ggactctagt cagtagcacg actagagtcc agagtacg    58

<210> SEQ ID NO 5
<211> LENGTH: 46
<212> TYPE: DNA
<213> ORGANISM: artificial sequence
<220> FEATURE:
<223> OTHER INFORMATION: Hairpin loop forming region from 5' blocking
      nucleic acids

<400> SEQUENCE: 5
cgtactctgg actctagtca gtagcacgac tagagtccag agtacg    46

<210> SEQ ID NO 6
<211> LENGTH: 22
<212> TYPE: RNA
<213> ORGANISM: homo sapiens

<400> SEQUENCE: 6
uagcagcacg uaaauauugg cg    22

<210> SEQ ID NO 7
<211> LENGTH: 22
<212> TYPE: RNA
<213> ORGANISM: homo sapiens

```
<400> SEQUENCE: 7
uagcagcaca uaaucguuug ug                                              22

<210> SEQ ID NO 8
<211> LENGTH: 22
<212> TYPE: RNA
<213> ORGANISM: homo sapiens

<400> SEQUENCE: 8
uagcagcaca ucaugguuua ca                                              22

<210> SEQ ID NO 9
<211> LENGTH: 21
<212> TYPE: RNA
<213> ORGANISM: homo sapiens

<400> SEQUENCE: 9
uagcagcaca gaaauauugg c                                               21

<210> SEQ ID NO 10
<211> LENGTH: 22
<212> TYPE: RNA
<213> ORGANISM: homo sapiens

<400> SEQUENCE: 10
cagcagcaau ucauguuuug aa                                              22

<210> SEQ ID NO 11
<211> LENGTH: 21
<212> TYPE: RNA
<213> ORGANISM: homo sapiens

<400> SEQUENCE: 11
cagcagcaca cugugguuug u                                               21

<210> SEQ ID NO 12
<211> LENGTH: 7
<212> TYPE: RNA
<213> ORGANISM: homo sapiens

<400> SEQUENCE: 12 agcagca                                                                7

<210> SEQ ID NO 13
<211> LENGTH: 58
<212> TYPE: DNA
<213> ORGANISM: artificial sequence
<220> FEATURE:
<223> OTHER INFORMATION: Blocking nucleic acid

<400> SEQUENCE: 13
cgtactctgg actctagtca gtagcacgac tagagtccag agtacgcgcc aatattta       58
```

METHOD FOR BLOCKING MIRNA

CROSS-REFERENCE TO RELATED APPLICATIONS

This application is a division under 35 U.S.C. § 120 of U.S. patent application Ser. No. 15/565,652, filed on 10 Oct. 2017, which issued as U.S. Pat. No. 10,480,023 on 11 Nov. 2019, U.S. patent application Ser. No. 15/565,652 is a national stage under 35 U.S.C. § 371 of International App. No. PCT/US16/26846, filed 10 Apr. 2016. International App. No. PCT/US16/26846 cites the priority under 35 U.S.C. § 119 of U.S. Pat. App. No. 62/146,015, filed 10 Apr. 2015. The contents of the foregoing applications are incorporated herein by reference, although the prosecution histories of said foregoing applications are not incorporated herein.

BACKGROUND

A. Field of the Disclosure

The present disclosure generally relates to the field of molecular biology. In particular, the present disclosure pertains to generating a sequencing library of micro RNA (miRNA). More specifically, the present disclosure pertains to reducing the frequency of specific miRNAs in a sequencing library.

B. Background

Micro RNAs are naturally occurring, small non-coding RNAs that are about 17-25 nucleotide bases in length in their biologically active form. miRNAs post-transcriptionally regulate gene expression by repressing target mRNA translation and by targeting transcripts for destruction. It is thought that miRNAs function as negative regulators, such that greater amounts of a specific miRNA will correlate with lower levels of target gene expression.

Given their important role in gene regulation, and therefore human health, large scale sequencing of miRNA has become a very valuable scientific tool in the study of human disease. There are various methods known in the art of creating a miRNA library to be sequenced.

Small RNAs can be measured with a variety of technologies, including qPCR, microarrays and solution-based hybridization, amongst others. Next-generation DNA sequencing (NGS) is also a powerful method for the discovery and quantification of small RNAs due to its technical performance, low expense, ultra-high throughput and its ability to agnostically detect and measure new species.

For example, as generally shown in FIG. 1, in a protocol utilized by Illumina, Inc. and other commercial companies that make Illumina compatible kits, to generate a miRNA sequencing library, an adenylated DNA 3' adapter 40 with a blocked 3' end is ligated to an RNA molecule's 10 3' end 20 using a truncated T4 RNA ligase 2 50. This truncated T4 RNA ligase 2 50 requires the 3' adapter 40 substrate to be adenylated. The result is that fragments of other RNA species in the total RNA sample are not ligated together in this reaction; only the pre-adenylated oligonucleotide can be ligated to free 3' RNA 20 ends resulting in a miRNA molecule with a 3' adapter ligated thereto 60. Moreover, since the 3' adapter 20 is 3' blocked, it cannot serve as a substrate for self-ligation. In the next step, a 5' adapter 70 is added along with RNA ligase 1 80. Only RNA molecules 10 whose 5' ends 30 are phosphorylated will be effective substrates for the subsequent ligation reaction. After this second ligation, an miRNA with both 3' and 5' adapters ligated thereto 90 is formed. Next, reverse transcription polymerase chain reaction (RT-PCR) amplification 100 is performed. After RT-PCR amplification 100 the library may be sequenced and analyzed. This library preparation method results in an oriented library such that the sequencing always reads from the 5' end 30 to the 3' end 20 of the original RNA molecule 10

However, NGS of small RNAs has several technical challenges. Among these is the well-reported biased behavior of the modified forms of T4 RNA Ligase 2 commonly used in sequencing library generation protocols. This bias manifests in small RNA libraries as differential ligation, creating an over-representation of certain species and an under-representation of others. When small RNA libraries are constructed from many sample types, these biases in ligation efficiency, combined with inherent abundance differences, can yield inaccurate results. Highly abundant small RNA species may be preferentially ligated such that their representation in the library becomes inordinately high, diminishing the ability to measure other less abundant species. The precise detection of these underrepresented species would thus require very high sequencing depths and proportionally higher costs. Additionally, highly abundant species interfere with many normalization techniques, limiting the utility of the collected reads.

In small RNA libraries made from human plasma and serum, many of the most highly abundant species are probably derived from blood cell populations. While these may be of interest in some applications, miRNAs and other small RNAs that act as biomarkers for many diseases, such as cancer and neurodegenerative disease, may be of low abundance in the blood of afflicted patients. Accordingly, the problem facing researchers interested in blood-based miRNA biomarkers is how to measure precisely low-abundance species in a background of highly abundant and less informative species that comprise most of the reads in sequencing library.

Accordingly, there is a need for an effective method for reducing the frequency of overrepresented or abundant miRNAs 10 in miRNA sequencing libraries.

SUMMARY

The above problems (as well as others) are addressed by the inventions provided in this disclosure, although not every embodiment disclosed here will address every problem disclosed above.

In a first aspect, a blocking nucleic acid for use in reducing the abundance of a unwanted micro-RNA (miRNA) in an miRNA library is provided, the blocking nucleic acid comprising: a 5' end of the blocking nucleic acid and a 3' end of the blocking nucleic acid; a single-stranded complementary region at one of the 5' end of the blocking nucleic acid or the 3' end of the blocking nucleic acid, that anneals with a binding region at a first end of the unwanted miRNA under stringent conditions, wherein said first end is either the 5' end or the 3' end of the unwanted miRNA, and wherein the complementary region has a terminal end; a hairpin loop forming region adjacent to the complimentary region, the hairpin loop forming region having a ligative terminal end; and a first blocking moiety linked to the terminal end of the hairpin loop forming region, in which said first blocking moiety cannot serve as a substrate for ligases.

In a second aspect, a blocking nucleic acid for use in reducing the abundance of an unwanted miRNA in an miRNA library is provided, the blocking nucleic acid comprising: a Crick strand having a 3' end and a 5' end; a single stranded complementary region at one of the 5' end of the Crick strand or the 3' end of the Crick strand, that anneals with a binding region at a first end of the unwanted miRNA under stringent conditions, wherein said first end is the 5' end or the 3' end of the unwanted miRNA; a double-stranded region on the Crick strand adjacent to the complementary region, the double-stranded region comprising a Watson strand that is annealed to the Crick strand, the Watson strand having a 5' end and a 3' end; a first blocking moiety linked to the 3' end of the Crick strand, wherein the first blocking moiety cannot serve as a substrate for ligases; a second blocking moiety linked to the 5' end of the Crick strand, wherein the second blocking moiety cannot serve as a substrate for ligases; a third blocking moiety linked to the 3' end of the Watson strand if the complementary region is at the 3' end of the Crick strand, or linked to the 5' end of the Watson strand if the complementary region is at the 5' end of the Crick strand, wherein the third blocking moiety cannot serve as a substrate for ligases; and a ligative terminal end on the Watson strand, the ligative terminal end located at the 3' end of the Watson strand if the complementary region is at the 5' end of the Crick strand, or at the 5' end of the Watson strand if the complementary region is at the 3' end of the Crick strand.

In a third aspect, a method of preventing an unwanted miRNA from participating in reverse transcription polymerase chain reactions (RT-PCR) is provided, the unwanted miRNA having a 5' end and a 3' end, the method comprising: annealing the complementary region of either of the blocking nucleic acids above to the binding site at the first end of the unwanted miRNA, wherein the first end of the unwanted miRNA is one of the 5' end or the 3' end. The product of the method is also provided.

In a fourth aspect, a method of reducing the abundance of an unwanted miRNA in an miRNA library is provided, the unwanted miRNA having a 5' end and a 3' end, the method comprising: purifying RNA from a sample comprising a plurality of miRNAs; introducing an adenylated nucleic acid adapter and a first DNA/RNA ligase under conditions to allow the adenylated nucleic acid adapter to ligate to the 3' end of the plurality of miRNAs; introducing either of the blocking nucleic acids above under conditions to allow the complementary region of the blocking nucleic acid to anneal to the binding region of the unwanted miRNA, to produce a blocked sample; introducing an RNA adapter and an RNA ligase under conditions to allow the RNA adapter to ligate the 5' end of the plurality of miRNAs; introducing a reverse transcriptase to the blocked sample under conditions to allow the reverse transcription of the plurality of miRNAs to produce a cDNA sample; and performing the polymerase chain reaction (PCR) on the cDNA sample to produce the miRNA library with reduced abundance of unwanted miRNA. The miRNA library with reduced abundance of non-target miRNA that is the product of this method is also provided.

In a fifth aspect, a kit for reducing the frequency of an miRNA in an miRNA library is provided, the kit comprising either of the blocking nucleic acids above.

In a sixth aspect, a blocked miRNA complex is provided, comprising: an miRNA; and either of the blocking nucleic acids above annealed to the binding region at the first end of the miRNA, wherein the first end is one of the 5' end or the 3' end.

In a seventh aspect, a nucleic acid is provided, comprising a sequence having at least a certain level of identity to one of SEQ ID NO: 1-4 and 13. In an eighth aspect, a nucleic acid is provided that anneals under highly stringent conditions with the nucleic acid of the seventh aspect. In a ninth aspect, an organism or vector is provided comprising any of the nucleic acids of the seventh and eight aspects.

The above summary presents a simplified summary in order to provide a basic understanding of some aspects of the claimed subject matter. This summary is not an extensive overview. It is not intended to identify key or critical elements or to delineate the scope of the claimed subject matter. Its sole purpose is to present some concepts in a simplified form as a prelude to the more detailed description that is presented later.

BRIEF DESCRIPTION OF THE DRAWINGS

A more particular description of the invention will be rendered by reference to specific embodiments thereof which are illustrated in the drawings. It is appreciated that these drawings are not intended to limit the scope of the claims.

FIG. 22. An embodiment of the blocking nucleic acid without a hairpin loop in the method of blocking an miRNA. FIG. 22A shows 5' blocking nucleic acid.

DETAILED DESCRIPTION

A. Definitions

Figure 1:
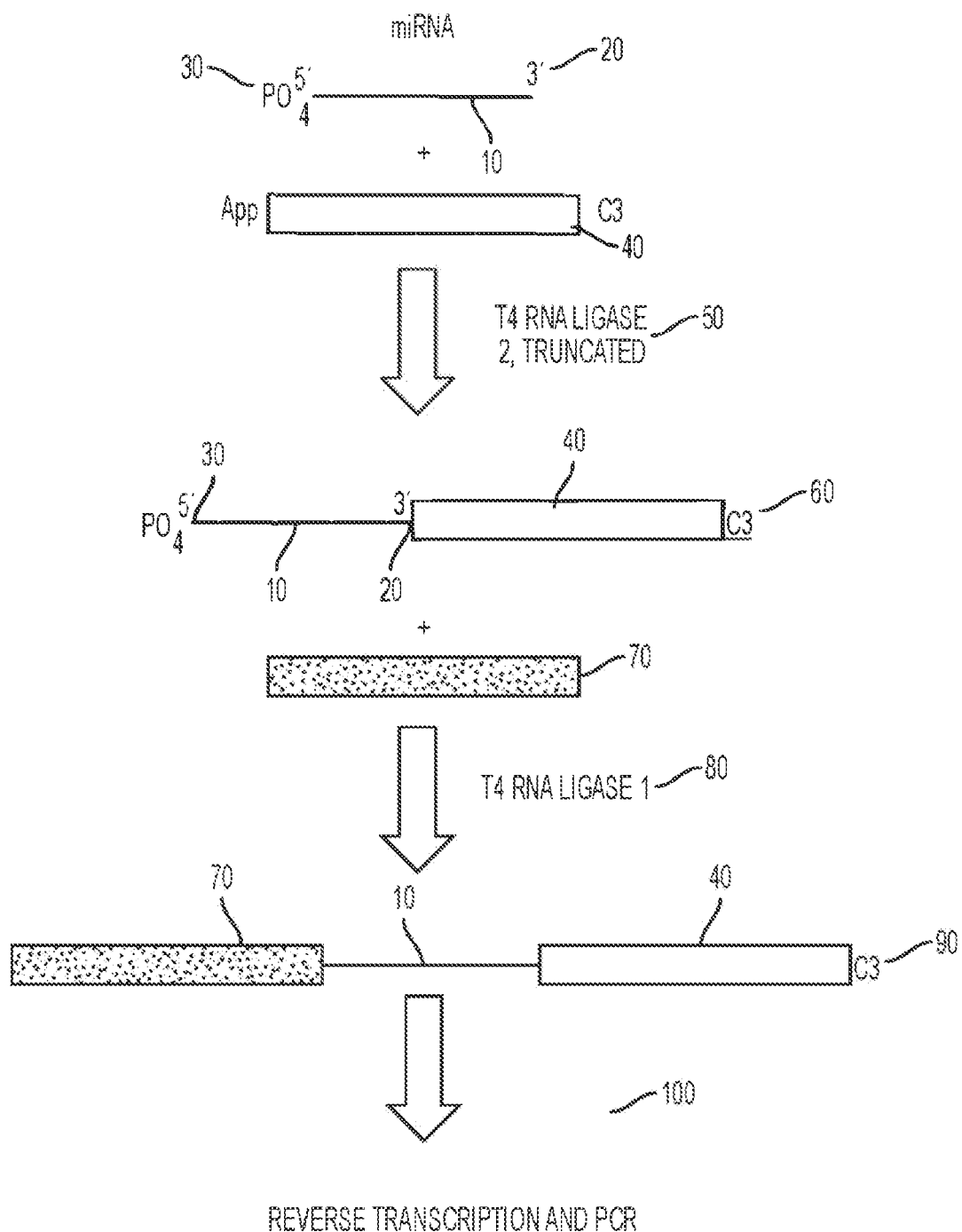
FIG. 1. Flow chart of an earlier protocol, in which a preadenylated adaptor is ligated to the 3' end of a small RNA pool using T4 RNA Ligase 2, truncated. Subsequently, a second adaptor is added to the 5' end of the miRNA with T4 RNA Ligase 1, followed by reverse transcription and PCR.

Unless otherwise defined, all terms (including technical and scientific terms) used herein have the same meaning as commonly understood by one of ordinary skill in the art of this disclosure. It will be further understood that terms, such as those defined in commonly used dictionaries, should be interpreted as having a meaning that is consistent with their meaning in the context of the specification and should not be interpreted in an idealized or overly formal sense unless expressly so defined herein. Well known functions or constructions may not be described in detail for brevity or clarity.

The terminology used herein is for the purpose of describing particular embodiments only and is not intended to be limiting. As used herein, the singular forms "a", "an" and "the" are intended to include the plural forms as well, unless the context clearly indicates otherwise.

The terms "first," "second," and the like are used herein to describe various features or elements, but these features or elements should not be limited by these terms. These terms are only used to distinguish one feature or element from another feature or element. Thus, a first feature or element discussed below could be termed a second feature or element, and similarly, a second feature or element discussed below could be termed a first feature or element without departing from the teachings of the present disclosure.

With reference to the use of the word(s) "comprise" or "comprises" or "comprising" in the foregoing description and/or in the following claims, those words are used on the basis and clear understanding that they are to be interpreted inclusively, rather than exclusively, and that each of those words is to be so interpreted in construing the foregoing description and/or the following claims.

The term "consisting essentially of" means that, in addition to the recited elements, what is claimed may also contain other elements (steps, structures, ingredients, components, etc.) that do not adversely affect the operability of what is claimed for its intended purpose as stated in this disclosure. Importantly, this term excludes such other elements that adversely affect the operability of what is claimed for its intended purpose as stated in this disclosure, even if such other elements might enhance the operability of what is claimed for some other purpose.

The term "individual", "subject" or "patient" as used herein refers to any animal, including mammals, such as mice, rats, other rodents, rabbits, dogs, cats, swine, cattle, sheep, horses, or primates, and humans. The term may specify male or female or both, or exclude male or female.

The terms "about" and "approximately" shall generally mean an acceptable degree of error or variation for the quantity measured given the nature or precision of the measurements. Typical, exemplary degrees of error or variation are within 20 percent (%), preferably within 10%, and more preferably within 5% of a given value or range of values. For biological systems, the term "about" refers to an acceptable standard deviation of error, preferably not more than 2-fold of a given value. Numerical quantities given herein are approximate unless stated otherwise, meaning that the term "about" or "approximately" can be inferred when not expressly stated.

The term "nucleotides" as used herein refer to any such known groups, natural or synthetic. It includes conventional DNA or RNA bases (A, G, C, T, U), base analogs, e.g., inosine, 5-nitroindazole and others, imidazole-4-carboxamide, pyrimidine or purine derivatives, e.g., modified pyrimidine base 6H,8H-3,4-dihydropyrimido[4,5-c][1,2]oxazin-7-one (sometimes designated "P" base that binds A or G) and modified purine base N6-methoxy-2,6-diaminopurine (sometimes designated "K" base that binds C or T), hypoxanthine, N-4-methyl deoxyguanosine, 4-ethyl-2'-deoxycytidine, 4,6-difluorobenzimidazole and 2,4-difluorobenzene nucleoside analogues, pyrene-functionalized LNA nucleoside analogues, deaza- or aza-modified purines and pyrimidines, pyrimidines with substituents at the 5 or 6 position and purines with substituents at the 2, 6 or 8 positions, 2-aminoadenine (nA), 2-thiouracil (sU), 2-amino-6-methylaminopurine, O-6-methylguanine, 4-thio-pyrimidines, 4-amino-pyrimidines, 4-dimethylhydrazine-pyrimidines, O-4-alkyl-pyrimidines and hydrophobic nucleobases that form duplex DNA without hydrogen bonding. Nucleobases can be joined together by a variety of linkages or conformations, including phosphodiester, phosphorothioate or methylphosphonate linkages, peptide-nucleic acid linkages.

The term "polynucleotide" as used herein refers to a multimeric compound comprising nucleotides linked together to form a polymer, including conventional RNA, DNA, LNA, BNA, copolymers of any of the foregoing, and analogs thereof.

The term "nucleic acid" as used herein refers to a single stranded polynucleotide or a duplex of two polynucleotides. Such duplexes need not be annealed at all locations, and may contain gaps or overhangs.

The term "nick" as used herein refers to a discontinuity in a double stranded nucleic acid molecule where there is no phosphodiester bond between adjacent nucleotides of one strand.

The term "miRNA" is used herein according to its ordinary and plain meaning in the art, and refers to a microRNA molecule found in eukaryotes that is involved in RNA-based gene regulation. The term will be used to refer to the single-stranded RNA molecule processed from a precursor. Individual miRNAs have been identified and sequenced in different organisms, and they have been given names. The methods and compositions should not be limited to miRNAs identified in the application, as they are provided as examples, not necessarily as limitations of the invention.

Nucleic acids are "complementary" to each other, as used herein, when a nucleotide sequence in one strand of a nucleic acid, due to orientation of its nucleotide hydrogen atoms, hydrogen bonds to another sequence on an opposing nucleic acid strand (of course, a strand of a nucleic acid may be self-complementary as well). The complementary bases typically are, in DNA, A with T, and C with G, and, in RNA, C with G, and U with A. Complementarity can be perfect or substantial/sufficient. Perfect complementarity between two nucleic acids means that the two nucleic acids can form a duplex in which every base in the duplex is bonded to a complementary base by Watson-Crick pairing. "Substantial" or "sufficient" complementary means that a sequence in one strand is not perfectly complementary to a sequence in an opposing strand, but that sufficient bonding occurs between bases on the two strands to form a stable hybrid complex at a given set of hybridization conditions (e.g., salt concentration and temperature). Such conditions can be predicted by using the sequences and standard models to predict the $T_m$ of hybridized strands, or by empirical determination of $T_m$ by using established methods. $T_m$ refers to the temperature at which a population of hybridization complexes formed between two nucleic acid strands are 50% denatured. At a temperature below the $T_m$, formation of a hybridization complex is favored, whereas at a temperature above the Tm, melting or separation of the strands in the hybridization complex is favored.

The term "ligase" as used herein refers to an enzyme that catalyzes the formation of a phosphodiester bond between two polynucleotides, or between the ends of a single polynucleotide. Ligases include ATP-dependent double-strand polynucleotide ligases, NAD+-dependent double-strand DNA or RNA ligases and single-strand polynucleotide ligases. Specific examples of ligases include, but are not limited to, bacterial ligases such as E. coli DNA ligase and Taq DNA ligase, Ampligase® thermostable DNA ligase (Epicentre® Technologies Corp., part of Illumina®, Madison, Wis.), phage ligases such as T3 DNA ligase, T4 DNA ligase and T7 DNA ligase and mutants thereof and T4 RNA ligase 1 and T4 RNA ligase 2 and mutants thereof such as Sso7 fusion proteins, T4 truncated and mutated (K227Q) RNA ligase 2. In this disclosure the term "DNA/RNA ligase" or "RNA/DNA ligase" refers to a ligase that catalyzes the formation of a phosphodiester bond between an RNA molecule and a DNA molecule. Examples of DNA/RNA ligases include T4 DNA ligase and T4 RNA ligase 2.

The term "ligative" means available for a ligation reaction, or a suitable substrate for a ligase.

B. Blocking Nucleic Acids

A blocking nucleic acid 120 for use in reducing the abundance of a non-target micro-RNA (miRNA) in an miRNA library is provided, including: a single-stranded complementary region 130 at one of the 5' end of the blocking nucleic acid 120 or the 3' end of the blocking nucleic acid 120, that anneals with a binding region at a first end of the unwanted miRNA 10; a hairpin loop forming region 140 or other double-stranded region 170 adjacent to the complimentary region 130, in which all of the terminal ends of the blocking nucleic acid 120 except one are unavailable to participate in ligase reactions. The available terminal end will be immediately adjacent to the miRNA when the miRNA is annealed to the complementary region 130, leaving a nick that can be filed using an appropriate ligase. The terminal ends are rendered unavailable to participate in ligase reactions by removing or masking the 4' phosphate group or 3' hydroxyl group. In this disclosure, if the complementary region 130 of the blocking nucleic acid 120 is complementary to the 5' end of the unwanted miRNA 30 in question, it is referred to as a "5' blocking nucleic acid." Similarly, if the complementary region 130 of the blocking nucleic acid is complementary to the 3' end of the unwanted miRNA 20 in question, it is referred to as a "3' blocking nucleic acid."

Figure 2:
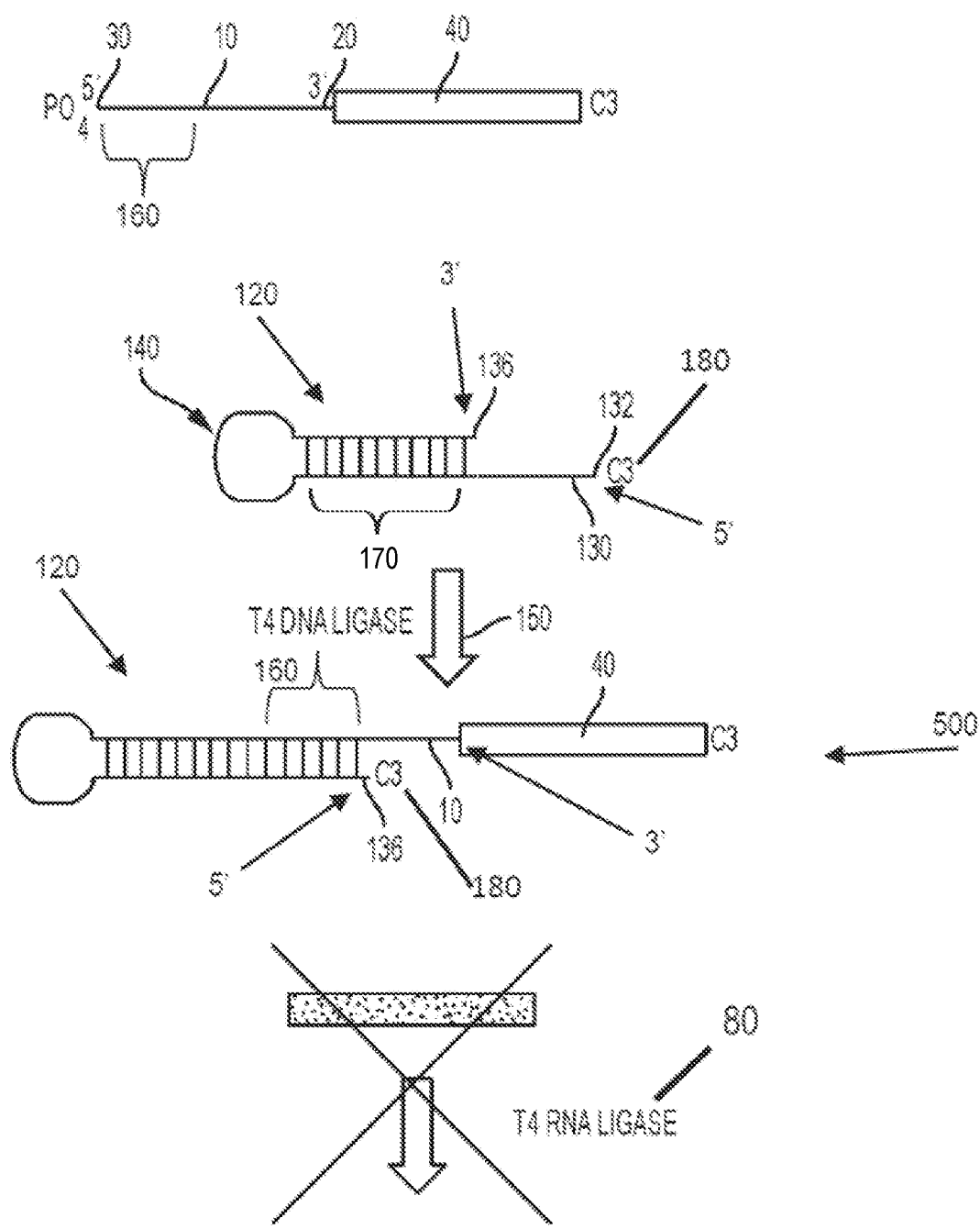
FIG. 2. Flow chart on an exemplary embodiment of the method, in which a hairpin oligonucleotide with an overhang complementary to the 5' end of the targeted miRNA is attached via ligation with T4 DNA Ligase to the 5' end of the miRNA subsequent to the ligation of the adaptor to the 3' end. This prevents the ligation of the second adaptor to the 5' end of the miRNA, resulting in a product that does not amplify during PCR.

A first aspect of the blocking nucleic acid 120 comprises a hairpin loop forming region 140. Embodiments of the first aspect comprise a single-stranded complementary region 130 at one of the 5' end of the blocking nucleic acid 120 or the 3' end of the blocking nucleic acid 120, that anneals with a binding region at a first end of the unwanted miRNA 10 under stringent conditions, wherein said first end is either the 5' end or the 3' end of the unwanted miRNA 20, and wherein the complementary region 130 has a terminal end 132; a hairpin loop forming region 140 adjacent to the complimentary region, the hairpin loop forming region 140 having a ligative terminal end 136; and a first blocking moiety 180 linked to the terminal end of the hairpin loop forming region 140, in which said first blocking moiety 180 cannot serve as a substrate for ligases. The presence of the hairpin loop reduces the number of terminal ends that must be rendered unavailable for ligase reactions. It therefore has the advantage of simplifying the protocol. An embodiment of the first aspect of the blocking nucleic acid 120 is shown in FIG. 2.

Figure 22B:
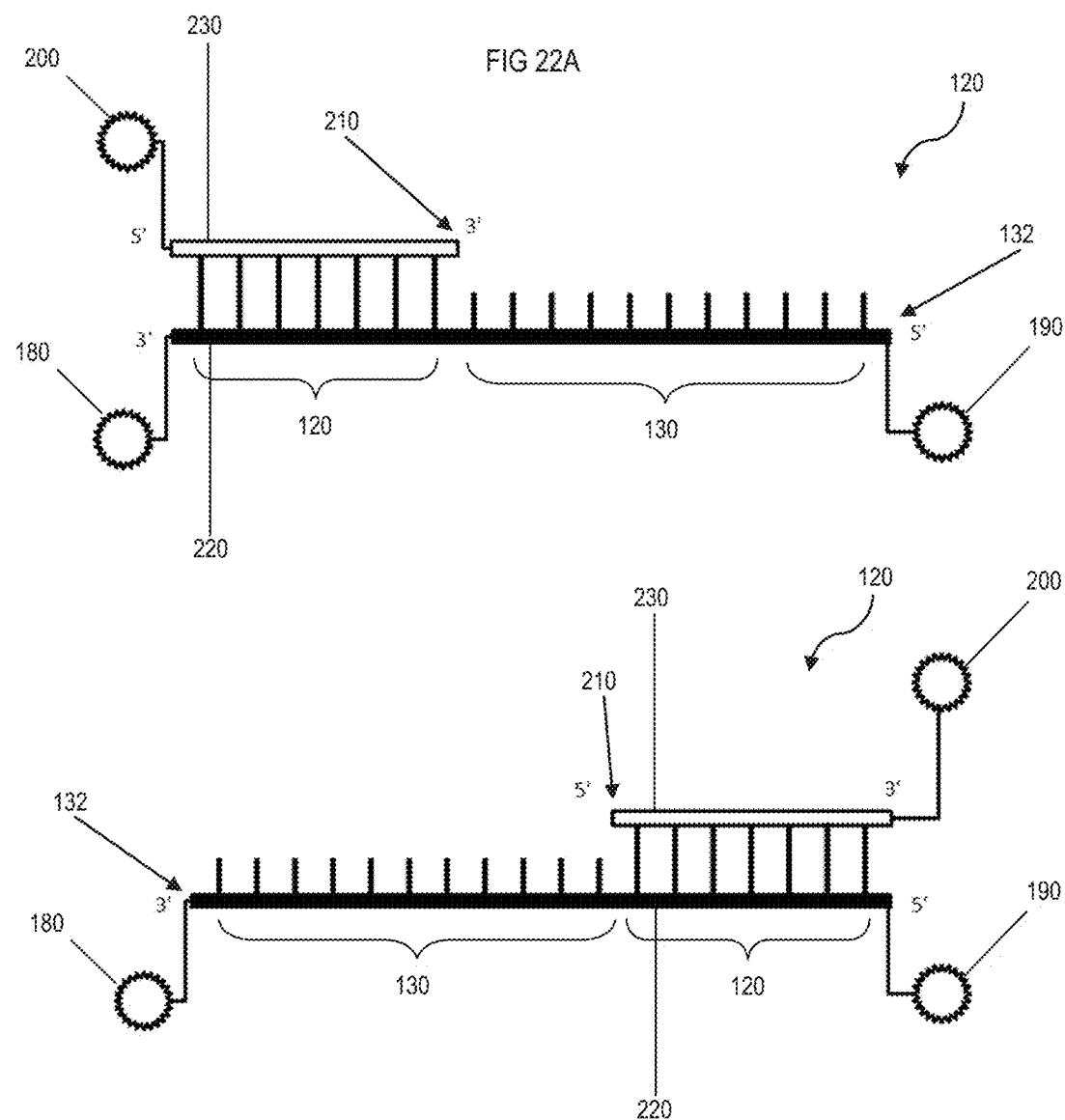
FIG. 22B shows a 3' blocking nucleic acid.

A second aspect of the blocking nucleic acid 120 does not necessary have a hairpin loop forming region 140, but has a double-stranded region 170 that may be formed by a second strand (or by a hairpin loop or other structure of the first strand). Embodiments of the second aspect of the blocking nucleic acid 120 comprise: a Crick strand 220; a single stranded complementary region 130 at one of the 5' end of the Crick strand 220 or the 3' end of the Crick strand 220, that anneals with a binding region at a first end of the unwanted miRNA 10 under stringent conditions, wherein said first end is the 5' end or the 3' end of the unwanted miRNA (30 and 20, respectively); a double-stranded region 170 on the Crick strand 220 adjacent to the complementary region 130, the double-stranded region 170 comprising a Watson strand 230 that is annealed to the Crick strand 220; a first blocking moiety 180 linked to the 3' end of the Crick strand 220, wherein the first blocking moiety 180 cannot serve as a substrate for ligases; a second blocking moiety 190 linked to the 5' end of the Crick strand 220, wherein the second blocking moiety 190 cannot serve as a substrate for ligases; a third blocking moiety 200 linked to the 3' end of the Watson strand 230 if the complementary region 130 is at the 3' end of the Crick strand 220, or linked to the 5' end of the Watson strand 230 if the complementary region 130 is at the 5' end of the Crick strand 220, wherein the third blocking moiety 200 cannot serve as a substrate for ligases; and a ligative terminal end 210 on the Watson strand 230, the ligative terminal end 210 located at the 3' end of the Watson strand 230 if the complementary region 130 is at the 5' end of the Crick strand 220, or at the 5' end of the Watson strand 230 if the complementary region 130 is at the 3' end of the Crick strand 220. An embodiment of the second aspect of the blocking nucleic acid 120 is shown in FIG. 22.

The miRNA is referred to as "unwanted," as one useful application of the blocking nucleic acid 120 is to reduce the abundance of over-represented miRNAs in miRNA libraries, but the blocking nucleic acid 120 can be used to bind to one end of any RNA molecule for a variety of applications. The descriptor "unwanted" should not be seen as an indication that the blocking nucleic acid 120 cannot or should not be used with any given RNA or type of RNA.

The complementary region 130 is described as single-stranded as it must be non-annealed in order to anneal with the miRNA, which is critical to its functioning. Of course, the blocking nucleic acid 120 could be prepared such that the complementary region 130 is annealed with another polynucleotide prior to use (for example, to aid in stability during storage and prevent dimerization), and then denatured in preparation for use. The complementary region 130 will be designed to be of sufficient length to be specific to its intended target(s), but short enough to bind easily to the binding region at the annealing temperature. Some embodiments of the complementary region 130 are about 5-50 nucleotides in length. Further embodiments of the complementary region 130 are about 8-20 nucleotides in length. Still further embodiments of the complementary region 130 are about 10-15 nucleotides in length. In a specific embodiment of the blocking nucleic acid 120, the complementary region 130 is 12 nucleotides in length.

The complementary region 130 is described as being at the 5' end or the 3' end of its associated polynucleotide to assure that the respective terminal end 210 is available for ligation. It is possible, however, that a blocking polynucleotide could be designed to place the complementary region 130 proximate to the 3' or 5' end, but not at the terminal end 210 itself; in such an embodiment, after annealing with the unwanted miRNA 10 the un-annealed tail could be clipped off with an endonuclease. After such endonuclease removal, and prior to ligation, the complementary region 130 would in fact be at the 5' or 3' end of the polynucleotide.

The complementary region 130 can be designed to anneal with a known sequence at the 3' or 5' end of an miRNA by those skilled in the art without undue experimentation. Thousands of miRNAs are known, and their sequences can be searched using online resources such as PHENOMIR 2.0 (provided by the Helmholtz Zentrum Munchen—German Research Center for Environmental Health IBIS Institute of Bioinformatics and Systems Biology, and available at mips.helmholtz-muenchen.de) and MIRBASE.org, managed by the Griffiths-Jones lab at the Faculty of Life Sciences, University of Manchester.

For example, one of the commonly over represented miRNA 10 molecules in miRNA sequencing libraries is mir-16, a miRNA that has been implicated in the development of B-cell lymphocytic leukemia in addition to breast, colon, brain, lung, prostate and stomach cancers. mir-16 is expressed in many tissue types and is often over-represented in miRNA sequencing libraries. Accordingly, the ability to decrease the overall frequency of mir-16 in sequencing libraries would be beneficial. Other over represented or abundant miRNAs include, but are not limited to mir-486, mir-451a and mir-26. Table 1 shows the nucleotide sequences of several blocking nucleic acids (DNAs) 120 and their respective target miRNAs 10. The complementary regions 130 of each are shown in white type on black background. The stem-and-loop forming regions of each are shown underlined. Note the consensus sequence between all four blocking nucleic acids in Table 1 at positions 13-58 (SEQ ID NO: 5). Note also that all of SEQ ID NO. 1-4 have stem-and-loop forming regions, and so form blocking nucleic acids having only one strand. It should be noted that in some situations a single blocking nucleic acid 120 may effectively reduce the frequency of more than one unwanted, over represented, or abundant miRNA 10 simultaneously.

1-4. The certain level of identity may be selected from at least 50%, 60%, 70%, 75%, 80%, 85%, 90%, 95%, 99%, and 100%. In a further embodiment, the certain level of identity is greater than 95%. In still further specific embodiments, the blocking nucleotide comprises one of SEQ ID NO: 1-4.

Some embodiments of 3' nucleic acid blockers specific to hsa-miR-16-5p comprise a sequence with a certain level of identity with SEQ ID NO: 13. The certain level of identity may be selected from at least 50%, 60%, 70%, 75%, 80%, 85%, 90%, 95%, 99%, and 100%. In a further embodiment, the certain level of identity is greater than 95%. The 3' end of SEQ ID NO: 13 is the complementary region 130 to a binding region on the 3' end of hsa-miR-16-5p.

The complementary region 130 will anneal with a binding region at the first end of the unwanted miRNA 10 under stringent conditions. Such stringency is based on the melting temperature ($T_m$) of the nucleic acid binding complex, as taught in Berger and Kimmel (1987, Guide to Molecular Cloning Techniques, Methods in Enzymology, 152, Academic Press, San Diego Calif.). The $T_m$ of an annealed duplex depends on the base composition of the duplex, the frequency of base mismatches, and the ionic strength of the reaction medium. The $T_m$ of a duplex can be calculated by those of ordinary skill in the art based on these two factors using accepted algorithms. Maximum stringency typically occurs at about 5° C. below $T_m$; high stringency at about 5-10° C. below $T_m$; intermediate stringency at about 10-20° C. below $T_m$; and low stringency at about 20-25° C. below $T_m$. As will be understood by those of skill in the art, a maximum stringency hybridization can be used to identify or detect identical nucleotide sequences while an intermediate (or low) stringency hybridization can be used to identify or detect similar or related sequences. The term "stringent" by itself in this context refers to intermediate stringency. Terms such as maximally stringent, highly stringent, and poorly stringent, refer to conditions of maximal stringency, high stringency, and low stringency respectively.

An example of maximally stringent conditions is provided in the working example below. Specifically, the stringent conditions may be the conditions set forth in the "Supplemental Methods" section of Working Example 1, under "Blocking Ligation." Note that the hybridization temperature in that example was 30° C., while the calculated $T_m$ of the duplex between the blocking nucleic acid 120 and the miRNA was 35° C.

TABLE 1

Exemplary 5' Blocking Nucleic Acids

| miRNA | Nucleotide Sequence (5' to 3') | SEQ ID NO. |
|---|---|---|
| mir-486 | CTCAGTACAGGACGTACTCTGGACTCTAGTCAGTAGCACGACTAGAGTCCAGAGTACG | 1 |
| mir-26 | GGATTACTTGAACGTACTCTGGACTCTAGTCAGTAGCACGACTAGAGTCCAGAGTACG | 2 |
| mir-451 | TGGTAACGGTTTCGTACTCTGGACTCTAGTCAGTAGCACGACTAGAGTCCAGAGTACG | 3 |
| mir-16 | TACGTGCTGCTACGTACTCTGGACTCTAGTCAGTAGCACGACTAGAGTCCAGAGTACG | 4 |

It is contemplated that the complementary region 130 of any of the 5' blocking nucleic acids 120 will share a certain level of identity with positions 1-12 of one of SEQ ID NO:

The complementary region 130 will generally function to anneal under stringent conditions with at least 5 consecutive bases in the miRNA. Examples of the sequences of overrepresented miRNAs in miRNA libraries are provided in SEQ ID NO: 6-11. In embodiments of the blocking nucleic acid 120 useful to block those miRNAs, the complementary region 130 may anneal under stringent conditions with at least 5 consecutive bases of at least one of SEQ ID NOS: 6-11. In some such embodiments, the complementary region 130 may anneal under stringent conditions with at least 8 consecutive bases of at least one of SEQ ID NOS: 6-11. In further embodiments, the complementary region 130 may anneal under stringent conditions with at least 10 consecutive bases of at least one of SEQ ID NOS: 6-11. In further embodiments, the complementary region 130 may anneal under stringent conditions with positions 2-8 of at least one of SEQ ID NOS: 6-11 (SEQ ID NO: 12). In specific embodiments, the complementary region 130 may anneal under stringent conditions with positions 1-9 of at least one of SEQ ID NOS: 6-11.

In further embodiments of the blocking nucleic acid 120, the complementary region 130 will anneal with a binding region at the first end of the unwanted miRNA 10 under highly stringent conditions. In still further embodiments of the blocking nucleic acid 120, the complementary region 130 will anneal with a binding region at the first end of the unwanted miRNA 10 under maximally stringent conditions.

The blocking moieties are moieties that are not available for ligation reactions, i.e., they cannot serve as substrates for ligases. Various known ligases are capable of ligating specific nucleic acids, but not others. Ligases all require the nucleotides to be ligated have an available 3' hydroxyl group and an available 5' phosphate group. Some embodiments of the blocking moieties are nucleotides from which the 3' hydroxyl group has been removed or the 5' phosphate group has been removed (or possibly both). The blocking moieties could also be non-nucleotide groups bonded to the terminal nucleotide in the strand. Such non-nucleotide groups include "spacers" such as C3 spacer (phosphoramidite), Spacer 9 (triethylene glycol), and Spacer 18 (hexa-ethyleneglycol). Other non-nucleotide spacers can include a propyl group, a propanol group, other organic alcohols, and other glycol compounds. Examples of nucleotide blocking moieties include an inverted deoxynucleotide, a dideoxynucleotide, and an inverted dideoxynucleotide. The first, second, and third blocking moieties when present may be the same moieties, or they may be independently selected, so long as each effectively prevents the associated polynucleotide from undergoing ligation.

The blocking moiety may be linked directly or indirectly to the blocking nucleic acid 120. If linked indirectly, a linker group may be present between the blocking group and the terminal nucleotide. Such linker groups may include, for example, Spacer 9 (triethylene glycol) and Spacer 18 (hexa-ethyleneglycol).

In contrast, the blocking nucleic acid 120 also has a ligative terminal end (136 or 210). In the first aspect (hairpin loop) of the nucleic acid, the ligative terminal end 136 is found at the end of the hairpin-loop forming region 140. In the second aspect, the ligative terminal end 210 is found at one end of the Watson strand 230. The ligative terminal end (136 or 210) is intended to be ligated to one of the ends of the miRNA. The ligative terminal end (136 or 210) will in many embodiments be a terminal nucleotide with an available 3' hydroxyl group, an available 5' phosphate group, or both. In some embodiments of the blocking nucleic acid 120, the ligative terminal end (136 or 210) is a natural nucleotide (e.g., A, T, C, G, U) with an available 3' hydroxyl group, an available 5' phosphate group, or both. In further embodiments, the ligative terminal end (136 or 210) is a non-natural nucleotide with an available 3' hydroxyl group, an available 5' phosphate group, or both. A group is "available" if it has at least one oxygen atom that can form a phosphodiester bond, and is not sterically hindered (or otherwise hindered) from doing so.

Some embodiments of the blocking nucleic acid 120 comprise the hairpin forming region. The presence of the hairpin forming region reducing the number of terminal ends that require blocking to avoid unwanted ligation. A hairpin loop occurs when two regions of the same strand, usually complementary in nucleotide sequence when read in opposite directions, base-pair to form a double helix that ends in an unpaired loop. The formation of a stem-loop structure is dependent on the stability of the resulting helix and loop regions. The first prerequisite is the presence of a sequence that can fold back on itself to form a paired double helix. The stability of this helix is determined by its length, the number of mismatches or bulges it contains (a small number are tolerable, especially in a long helix) and the base composition of the paired region. The stability of the loop also influences the formation of the stem-loop structure. Loops that are less than three bases long are sterically impossible and do not form. Large loops with no secondary structure of their own (such as pseudoknot pairing) are also unstable. Optimal loop length tends to be about 4-8 bases long. Commonly used 4 base pair loops ("tetraloops") include ANYA, CUYG, GNRA, UMAC and UNCG. Suitable hairpin loop structures can be designed by those of ordinary skill in the art. Specific embodiments of the hairpin loop forming region 140 comprise a sequence with a certain level of identity with SEQ ID NO: 5. The certain level of identity may be selected from at least 50%, 60%, 70%, 75%, 80%, 85%, 90%, 95%, 99%, and 100%. In a further embodiment, the certain level of identity is greater than 95%.

In the second aspect of the nucleic acid blocker, a double stranded region is present that is not necessarily a hairpin loop forming structure. It is described as having a Watson strand 230 and a Crick strand 220, although in some cases this may be the same strand folded over on itself. The terms "Watson" and "Crick" have no descriptive or restrictive meaning, except to mean that the two strands are at least partially annealed to one another. In the absence of a hairpin loop, blocking moieties as described above are present on both ends of the Crick strand 220. A blocking moiety will also be present on the end of the Watson strand 230 farthest from the single-stranded region. In this particular context, the blocking moieties on the two terminal ends (on Watson and Crick) farthest from the single-stranded region may be embodied in a polynucleotide linking Watson and Crick. As described above, a hairpin loop can serve this function, but the polynucleotide linking Watson and Crick need not have a hairpin loop structure to serve the purpose of making the two terminal ends farthest from the single-stranded complementary region 130 unavailable for ligation.

In the second aspect of the blocking nucleotide, the Watson strand 230 has only one blocking moiety, referred to as the "third blocking moiety" (200). As shown in FIG. 22, the third blocking moiety 200 will be on the terminal end of Watson farthest from the single-stranded complementary region 130. As the terminal end of Watson that is closest to the complementary region 130 must be ligated with the miRNA, it will not be blocked.

C. Methods of Excluding miRNA from RT-PCR

A method of preventing the unwanted miRNA 10 from participating in RT-PCR is provided. In a general embodiment, the method comprises annealing any of the blocking nucleic acids 120 described above to the binding region of the unwanted miRNA 160. After annealing, the blocking nucleic acid 120 may be ligated to the "first end" of the miRNA where the binding region 160 is located. As should be apparent from the schemes shown in FIGS. 2 and 22, the binding region 160 will be on the 5' end of the miRNA if the complementary region 130 is at the 5' of the blocking nucleic acid 120, and the binding region 160 will be on the 3' end of the miRNA if the complementary region 130 is at the 3' end of the blocking nucleic acid 120.

The annealing step will generally be carried out under at least intermediate stringent conditions. The higher the stringency, the less likely it will be that the complementary region 130 binds to an unintended miRNA. In some embodiments of the method, the annealing step will be carried out under highly stringent conditions or maximally stringent conditions.

The ligating step is carried out using the appropriate ligase. If the blocking nucleic acid 120 is an RNA, then an RNA/RNA ligase must be used. If the blocking nucleic acid 120 is a DNA, then a DNA/RNA ligase must be used. Many ligases of both types are commercially available, and their properties and protocols for their use are known to those of ordinary skill in the art. If the blocking nucleic acid 120 is a DNA, then the ligase may be for example T4 DNA ligase, which ligates RNA to DNA when an RNA/DNA duplex has been formed.

The method may be carried out on any RNA, and as explained above the term "unwanted" to characterize the miRNA refers only to one intended use of the method, and does not limit the structure or source of the RNA involved. Some embodiments of the method are for the purpose of preventing one or more unwanted miRNAs 10 from participating in RT-PCR, and in such embodiments the miRNA may be "unwanted" because it is a very abundant or over-represented miRNA in a sample. Examples of such abundant miRNA include mir-16, mir-486, mir-451, and mir-26. Accordingly, in some embodiments of the method the unwanted miRNA 10 is selected from those miRNAs. In some cases the complementary region 130 and annealing conditions may be designed to allow the complementary region 130 to anneal with more than one miRNA, and any such additional miRNAs could be any taught to be suitable in the method by themselves.

The product of the method will be an miRNA that is annealed to the blocking polynucleotide ("blocked miRNA complex" 500). Such a blocked miRNA complex 500 will be unable to participate in at least one of a 5' ligation reaction or a 3' ligation reaction.

D. Reducing the Abundance of Unwanted miRNA in an miRNA Library

A method of reducing the abundance of an unwanted miRNA 10 in an miRNA library is provided, using any of the blocking nucleic acids 120 provided above. A general embodiment of the method comprises the following steps in no particular order: (a) purifying RNA from a sample comprising a plurality of miRNAs; (b) introducing an adenylated nucleic acid adapter 40 and a first DNA/RNA ligase 50 under conditions to allow the adenylated nucleic acid adapter 40 to ligate to the 3' end of the plurality of miRNAs; (c) introducing any of the blocking nucleic acids 120 disclosed above under conditions to allow the complementary region 130 of the blocking nucleic acid 120 to anneal the binding region of the unwanted miRNA 160, to produce a blocked sample 450; (d) introducing an RNA adapter 70 and an RNA ligase 80 under conditions to allow the RNA adapter 70 to ligate the 5' end of the plurality of miRNAs; (e) introducing a reverse transcriptase to the blocked sample 450 under conditions to allow reverse transcription of the plurality of miRNAs, to produce a cDNA sample; and (f) performing PCR on the cDNA sample to produce the miRNA library with reduced abundance of the unwanted miRNA 10.

Steps such as the purification of RNA from a biological sample, ligating adapters to the 3' end and 5' end of the miRNA, in vitro reverse transcription, and PCR can be performed according to any suitable protocol known in the art. Some exemplary protocols can be found in the TruSeq®RNA Access Library Prep Guide, Illumina, Inc., San Diego, Calif. (2014).

Some embodiments of the method comprise introducing a second DNA/RNA ligase 150 under conditions to allow the blocking nucleic acid 120 to ligate to one of the 5' end and the 3' end of the unwanted miRNA (30 and 20, respectively). As is apparent from FIGS. 2 and 22, the blocking nucleic acid 120 will ligate to the end of the miRNA where the binding region 160 is located.

The adenylated nucleic acid adapter 40 may be any type of nucleic acid, including but not limited to DNA or RNA. Adenylated DNA adapters 40 have the advantage of superior stability, and are not vulnerable to ubiquitous RNAses. Some embodiments of the adenylated nucleic acid adapter 40 comprise a reverse transcriptase primer binding site. As is known in the art, reverse transcriptase enzymes require the binding of a primer before reverse transcribing RNA. Most known reverse transcriptase enzymes use tRNAs as primers. In retroviruses, plant pararetroviruses, and transposons containing long terminal repeats, reverse transcription is primed by specific tRNAs. All these retroelements contain a primer binding site complementary to the primer tRNA. The tRNAs most widely used as primers are tRNA(Trp), tRNA(Pro), tRNA(1,2Lys), tRNA(3Lys), tRNA(iMet). Other tRNAs such as tRNA(Gln), tRNA(Leu), tRNA(Ser), tRNA(Asn) and tRNA(Arg) are also occasionally used as primers. In the retroviruses and plant pararetroviruses, the primer binding site is complementary to the 3' end of the primer tRNA. In the case of retrotransposons, the primer binding site is either complementary to the 3' end or to an internal region of the primer tRNA. Those of ordinary skill in the art will select the reverse transcriptase primer binding site on the adenylated nucleic acid adapter 40 to bind whichever primer is known to function with the reverse transcriptase that has been selected for the method.

If a 5' blocking nucleic acid 120 is used, the adenylated nucleic acid adapter 40 may be ligated to the miRNA before or after annealing it to the blocking nucleic acid 120. In this situation the adenylated nucleic acid adapter 40 will often be ligated to the 3' end of the miRNA before ligating the blocking nucleic acid 120, to avoid the need to reduce residual ATP from the previous step. When using a 5' blocking nucleic acid 120, the step in which the blocking nucleic acid 120 is ligated to the miRNA will precede ligation of the RNA adapter 70 to the 5' end of the miRNA; otherwise blocking would be ineffective.

If a 3' blocking nucleic acid 120 is used, the adenylated nucleic acid adapter 40 must be ligated to the 3' end of the miRNA after annealing it to the blocking nucleic acid 120, or else blocking would be ineffective. In such cases it may be desirable to remove excess ATP left over from the ligation of the blocking nucleic acid 120 prior to ligating the adenylated nucleic acid adapter 40 to the 3' end of the miRNA. This can be done by any of several methods. For example, the sample may be run through a chromatographic column after ligating the blocking nucleic acid 120 to the 3' end of the miRNA, and prior to ligating the adenylated nucleic acid adapter 40 to the 3' end of the miRNA. The excess ATP could also be removed by chemical reaction, electrophoresis, or other methods. When a 3' blocking nucleic acid 120 is used, ligation of the RNA adapter 70 to the 5' end of the miRNA may occur before or after ligation of the blocking nucleic acid 120 to the 3' end of the miRNA.

The steps of reverse transcribing the blocked sample 450 and PCR amplifying the cDNA sample will occur in that order, and will occur after the steps marked (a)-(d) above.

The annealing will be carried out under stringent conditions, as described in previous sections of this disclosure. In some embodiments of the method, annealing will be carried out under highly stringent conditions or maximally stringent conditions. The creation of a duplex between the blocking nucleotide and the miRNA will leave a nick between them that will be linked by the DNA/RNA ligase.

The first DNA/RNA ligase 50 will be a ligase capable of ligating the adenylated nucleic acid adapter 40 to an RNA. One example is T4 RNA ligase 2, truncated. The truncated version has the desirable property of requiring that the DNA have an adenylated 5' terminal end, and so will function to specifically bind an adenylated nucleic acid adapter 40 to the 3' end of the miRNA. In order to prevent unwanted ligation products, the adenylated nucleic acid adapter 40 may have a blocking moiety at its 3' end. The blocking moiety may be any that is described above as suitable for use in the blocking nucleic acid 120.

The second DNA/RNA ligase 150 will be a ligase capable of ligating the binding region 160 of the miRNA to the double-stranded region 170 of the blocking nucleic acid 120. As such, it is preferably able to ligate a nick in a duplex between a DNA polynucleotide and an RNA polynucleotide where an overhang exists. A specific example of such a DNA/RNA ligase is T4 DNA ligase.

The RNA ligase 80 will be a ligase capable of ligating the 5' end of the miRNA to the 3' end of the RNA adapter 70. Any such ligases known in the art may be used. In some embodiments of the method the RNA ligase 80 will be T4 RNA ligase 1, which is capable of ligating single-stranded RNA and DNA as well as dinucleoside pyrophosphates.

The RNA adapter 70 serves to provide a known primer binding site during PCR. Consequently, it may correspond in length to a suitable length for a primer binding site. Various embodiments of the RNA adapter 70 may have lengths selected from 5-30 bases and 18-22 bases.

The miRNA library with reduced abundance of the unwanted miRNA 10 that is a product of the method is also provided. In this context "reduced abundance" refers to there being significantly less of the unwanted miRNA in the miRNA library than would be observed in a library of the same sample or a similar sample in which no blocker is used. FIG. 14-20 are clear illustrations of such reduced abundance. In some embodiments of the miRNA library, the abundance of the unwanted miRNA has been reduced by at least 50%. In further embodiment of the miRNA library, the abundance of unwanted miRNA has been reduced at least by an amount selected from the group consisting of: 60%, 70%, 75%, 80%, 85%, 90%, 95%, 97.5%, 98%, 99%, 99.5%, 99%, and 100%. Put another way, the reduced abundance may be at least a 2-fold reduction in abundance. In some embodiments of the method, the reduced abundance may be at least a 4-fold reduction, at least a 6-fold reduction, or at least an 8-fold reduction.

E. Kits

Kits are provided for reducing the frequency of an miRNA in an miRNA library, comprising any of the blocking nucleic acids 120 disclosed above. The kit may further comprise the reagents, buffers, enzymes, instruction booklets, positive and negative controls and other materials useful or necessary to carry out the methods described herein. Such additional materials may include those useful to RNA/RNA ligation, RNA/DNA ligation, PCR, reverse transcription, in situ hybridization, and RNA purification. Specific non-limiting examples of additional kit components include a container of any of the following: DNA/RNA ligase 610 capable of ligating DNA to RNA when annealed (for example, T4 DNA ligase 620); RNA/RNA ligase 630 (for example, T4 RNA ligase 1 (640)); an RNA/DNA ligase 650 (for example, T4 RNA ligase 2, truncated (660)); a plurality of DNA primers 680; a nucleotide solution 690; a PCR buffer 700; a thermophilic DNA polymerase 710, an adenylated nucleic acid adapter 720, and an RNA adapter 730. The listed additional kit components may be any that are described as suitable for the methods above. A "container of" the listed component may be any sort of container as could be easily designed by those of ordinary skill in the art. The container may contain more than one listed component, or it may contain other components apart from the ones listed. In some embodiments of the kit, the container contains only the listed component to the exclusion of others (although not necessarily to the exclusion of inactive substances such as buffers, solvents, etc.). As a result, reference to a kit comprising "a container of X and a container of Y" should be read to encompass a kit comprising two separate containers containing X and y respectively, and a kit comprising one container containing X and Y. In some embodiments of the kit, a given component may have its own container.

F. Nucleic Acids

Nucleic acid molecules are provided for use in the blocking nucleic acids 120, methods, and kits above. These include a nucleic acid comprising a sequence having at least a certain level of identity with any one of SEQ ID NO: 1-4 and 13. The level of identity may be ≥50%, 60%, 70%, 75%, 80%, 85%, 90%, 95%, 99%, and 100%. In a specific embodiment the level of identity is >95%. The nucleic acids also include those that anneal under stringent conditions with any of the foregoing. Some embodiments of the nucleic acid anneal to any of the foregoing under highly stringent conditions. In some further embodiments of the nucleic acid, the nucleic acid anneals to any of the foregoing under maximally stringent conditions. In a specific embodiment of the nucleic acid, the nucleic acid is the exact complement to any of the foregoing nucleic acids. These molecules may be any type of nucleic acid, including RNA, DNA, LNA, BNA, copolymers of any of the foregoing, and analogs thereof. In a specific embodiment, the nucleic acid is DNA.

A blocked miRNA complex 500 is also provided, comprising any of the blocking nucleic acids 120 disclosed above, and the unwanted miRNA 10 annealed to the complementary region 130. In some embodiments of the blocked miRNA complex, the blocking nucleic acid 120 is ligated to the first end of the miRNA. Some embodiments of the blocked miRNA complex 500 are the product of any of the methods of preventing an unwanted micro-RNA (miRNA) from participating in RT-PCR provided above. As such methods may be used to prevent RT-PCR on very abundant or overrepresented miRNAs in a sample, the miRNA may be any of mir-16, mir-15a, mir-15b, mir-195, mir-424, mir-497, mir-486, mir-451, and mir-26. The miRNA may comprise a sequence selected from SEQ ID NO: 6 (miR-16), 7 (miR-15a), 8 (miR-15b), 9 (miR-195), 10 (miR-424), 11 (miR-497), and 12 (consensus positions 2-8 of the foregoing). Organisms and vectors comprising any of the nucleic acids above are also provided. Examples of uses for such organisms and vectors are production of the nucleic acids, cloning of the nucleic acids, and stable storage of the same. Many suitable vectors are known in the art, such as viruses, plasmids, cosmids, fosmids, phagmids, artificial chromosomes, yeast artificial chromosomes, human artificial chormosomes, plant transformation vectors, and liposomes. Unicellular organisms are particularly useful in cloning, replicating, and maintaining nucleic acids of interest. Model unicellular organisms that are commonly used for this purpose include yeasts, other fungi, bacteria, protists, and archaea.

Specific model organisms are well known in the art, and include bacteria such as *Escherichia coli, Salmonella typhimurium, Pseudomonas fluorescens, Bacillus subtilis, Mycoplasma genitalium*, and various *Synechocystis* sp.; protists such as *Dictyostelium discoideum, Tetrahymena thermophila, Emiliania huxleyi*, and *Thalassiosira pseudonana*; and fungi such as *Aspergillus* sp., *Neurospora crassa, Saccharomyces cerevisiae*, and *Schizosaccharomyces pombe*.

G. Examples

I. Working Example #1: Ligation of Blocking Nucleic Acids to 5' End of miRNA Materials and Methods
Total RNA Isolation The protocol for collection of peripheral blood samples was approved by the Institutional Review Board at the University of Alabama at Birmingham, and all donors provided written, informed consent. Blood was collected into EDTA tubes. Within 30 min of collection, the plasma was isolated (~5 ml) and stored at −80° C. One milliliter plasma was centrifuged at 14,000 relative centrifugal force for 15 min and total RNA was isolated from the supernatant using the Plasma/Serum Circulating and Exosomal RNA Purification Kit (Slurry Format) (Norgen Biotek) following the manufacturer's directions. The eluate from this kit was further concentrated using the RNA Clean-Up and Concentration Kit (Norgen Biotek) using 20 µl elution buffer to collect the RNA.

Small RNA Sequencing and miRNA Blocking

Isolated total RNA containing miRNA was converted to cDNA sequencing libraries according to the method described in Vigneault et al. (2012) and Eminaga et al. (2013), with modification (the full protocol can be found in Supplemental Methods). Briefly, for each library, 4 µl isolated RNA was combined with one µl of 10 µl 3' adaptor and 1 µl T4 RNA Ligase 2, truncated (NEB) in the appropriate buffer for 1 h. Simultaneously, 1 µl 0.5 µM miRNA blocking oligonucleotide was incubated for 5 min at each of the following temperatures: 95° C., 65° C., 55° C., 45° C. and 35° C. to ensure the proper formation of the hairpin structure. Next, incubated blocking oligonucleotide was added to the 3' adaptor ligation product and incubated for 1 h at 30° C. and 15 min at 65° C. in the presence of T4 DNA Ligase (NEB) in the appropriate buffer to anneal and block the targeted miRNA from further reactions. One microliter of 10 µM reverse transcription primer was annealed to the 3' adaptor ligation product for 5 min at 75° C., 30 min at 37° C. and 15 min at 25° C. prior to the addition of the 5' adaptor in order to reduce formation of adaptor-dimer products. One microliter of 20 µM pooled 5' adaptor was incubated for 2 min at 70° C. and then ligated with T4 RNA Ligase 1 (NEB) to each reaction product for 1 h at 25° C. Ligated reaction products were reverse transcribed using SuperScript II (Invitrogen) and amplified via PCR using Phusion High-Fidelity PCR Master Mix (NEB). The thermal cycling conditions were 94° C. for 30 s, followed by 15 cycles of 94° C. for 10 s and 72° C. for 45 s and a final extension at 65° C. for 5 min.

Libraries were cleaned and concentrated using a MinElute PCR Purification Kit (Qiagen), following the manufacturer's instructions, and eluted into a final volume of 20 µl. Libraries were separated on a TBE-Urea 10% acrylamide gel (Bio-Rad) with warm buffer for 50 min. The band corresponding to miRNAs (~135-145 base pairs) was excised, eluted from the gel, precipitated and resuspended in 10 µl of EB Buffer (Qiagen). Small RNA library concentration was quantified by the Library Quantification Kit—Illumina/ABI Prism (KAPA Biosystems) and sequenced on a HiSeq2000 or aMiSeq according to standard Illumina protocols.

Data Processing and Analysis

Adaptor sequences were trimmed from the raw fastq files using Cutadapt (37). The trimmed reads were aligned to pre-miRNA sequences (miRBase version 19) (38) using Bowtie2 (39). The alignments were filtered to keep only those alignments that had two or fewer base mismatches and yielded a unique best alignment as measured by the Bowtie2 alignment score. The remaining unaligned reads were then aligned to the hg19 reference genome using Bowtie2. Again, unique best reads were required. For miRNAs, read counts were obtained by counting the overlaps of the reads aligned to the pre-miRNAs with the canonical mature form boundaries (miRBase version 19) using BEDtools (40). Any overlap with the mature region was counted. The miRNA read counts for each experiment were down-sampled to a common level using random sampling implemented in R (base package). When the 'average' of two replicates was taken (generally for plotting), the following procedure was used: the two libraries were down-sampled to a common total count value and then counts for each species were summed. This summed library was then down-sampled to the original common total count value. This processes is favored for averaging replicate libraries because it preserves the count nature of the data and accordingly the underlying distribution. Differential expression was calculated using the package DESeq2 (41) in R using 'local' dispersion estimates and 'LRT' tests. A significant result was defined as one with Benjamini-Hochberg adjusted P-value <0.01. Dispersion estimates were calculated with DESeq2 as well using the 'local' mode. Prior to plotting in FIG. 6A, the estimates were smoothed using the spline function in R (base package).

Results
Blocking Hsa-miR-16-5p in Sequencing Libraries

Figure 8:
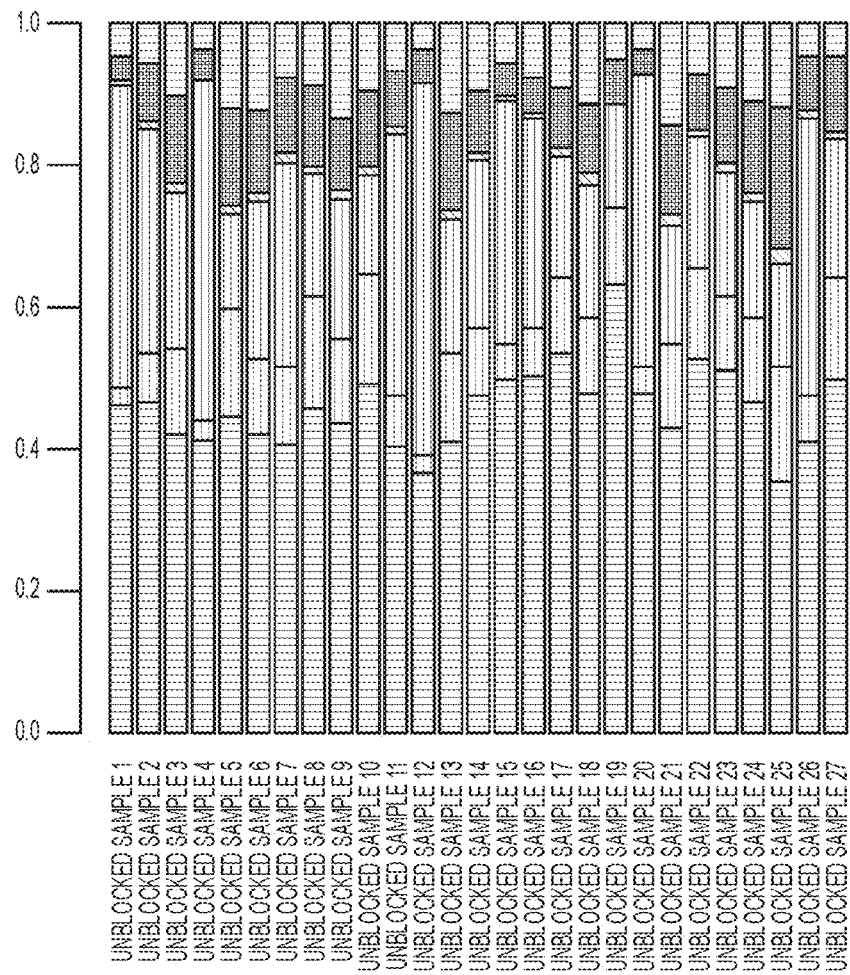
FIG. 8. Categorical distribution of reads from a set of unblocked human plasma libraries. The fraction of reads falling into six categories for 27 libraries derived from human plasma samples is shown. Solid horizontal lines indicate reads aligning to miRNAs but not to hsa-miR-16-5p. Vertical broken lines indicate reads that map to the human genome but are not miRNAs. Vertical solid lines indicate reads aligning to hsa-miR-16-5p. Horizontal crosshatching indicates reads that align to the spike-ins. Checks are reads that failed to align to miRNAs or the human genome. Broken horizontal lines are reads that are adaptor-dimer.

In a set of small RNA sequencing libraries from 27 human plasma samples that were prepared by using a slightly modified version of the protocol described by Alon et al. (28), reads mapping to hsa-miR-16-5p comprised between 20 and 60% of the total aligned reads in the libraries (FIG. 8). Furthermore, consistent with other reports (32, 33), hsa-miR-16-5p levels correlated with the degree of hemolysis present in the sample. The massive abundance of hsa-miR-16-5p in these libraries makes sequencing to a sufficient depth to detect lowly abundant miRNAs very expensive. Proper normalization of libraries in which one or few species dominate the reads is problematic. Also, because the hsa-miR-16-5p level varies, sequencing multiple samples to a common depth, in terms of non-hsa-miR-16-5p reads, is difficult.

To resolve these issues, an approach was devised to remove hsa-miR-16-5p from the sequencing libraries by blocking it as a substrate of T4 RNA Ligase 1 during the ligation of the adaptor to the 5' end (FIG. 2). In the standard protocol (FIG. 1), a pre-adenylated DNA oligonucleotide adaptor is ligated to the 3' ends of the pool of small RNA species using truncated T4 RNA Ligase 2. Subsequently, a RNA oligonucleotide adaptor is ligated to the 5' ends using unmodified T4 RNA Ligase 1. The resulting product is reverse transcribed and amplified with PCR. In the modified protocol (FIG. 2), use was made of an oligonucleotide comprised of a self-complementary hairpin with a 12-base overhang on its 5' end that is the reverse complement of the first 12 bases of the 5' end of the canonical sequence of the targeted miRNA. The 5' end of the oligonucleotide is modified with a C3 spacer (propyl group) to prohibit its participation in any unwanted ligation reactions. This 'blocker' oligonucleotide is introduced after the ligation of the pre-adenylated adaptor to the 3' ends of the small RNA pool but prior to the ligation of the adaptor to the 5' ends. The complementary portions of the targeted miRNA species and the blocker participate in Watson-Crick base pairing to form a double stranded RNA:DNA hybrid with a missing phosphodiester bond between the 3' end of the blocker and the 5' end of the targeted miRNA, comprising a 'nick'. T4 DNA Ligase recognizes this hybrid molecule and seals the nick (NEB product literature), resulting in the blocker being covalently bound to the 5' end of the target miRNA. The presence of the hairpin and the C3 blocker prevent the subsequent ligation of the adaptor to the 5' end of this product. Without the primer binding sequence contained in the adaptor, this 'blocked' product is not amplified in downstream PCR, effectively removing it from the final library.

Figure 3:
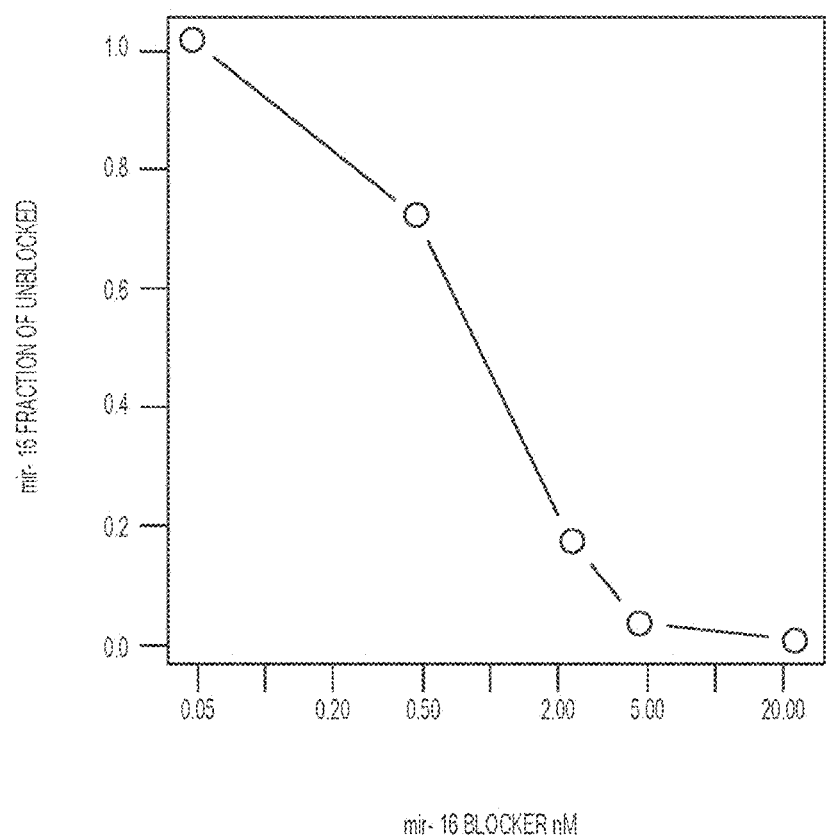
FIG. 3. Graph showing the fraction of hsa-miR-16-5p present in a blocked library generated from human heart total RNA using a titration of a blocking oligonucleotide targeting hsa-miR-16-5p compared to the unblocked library is shown on the y-axis.
Figure 9:
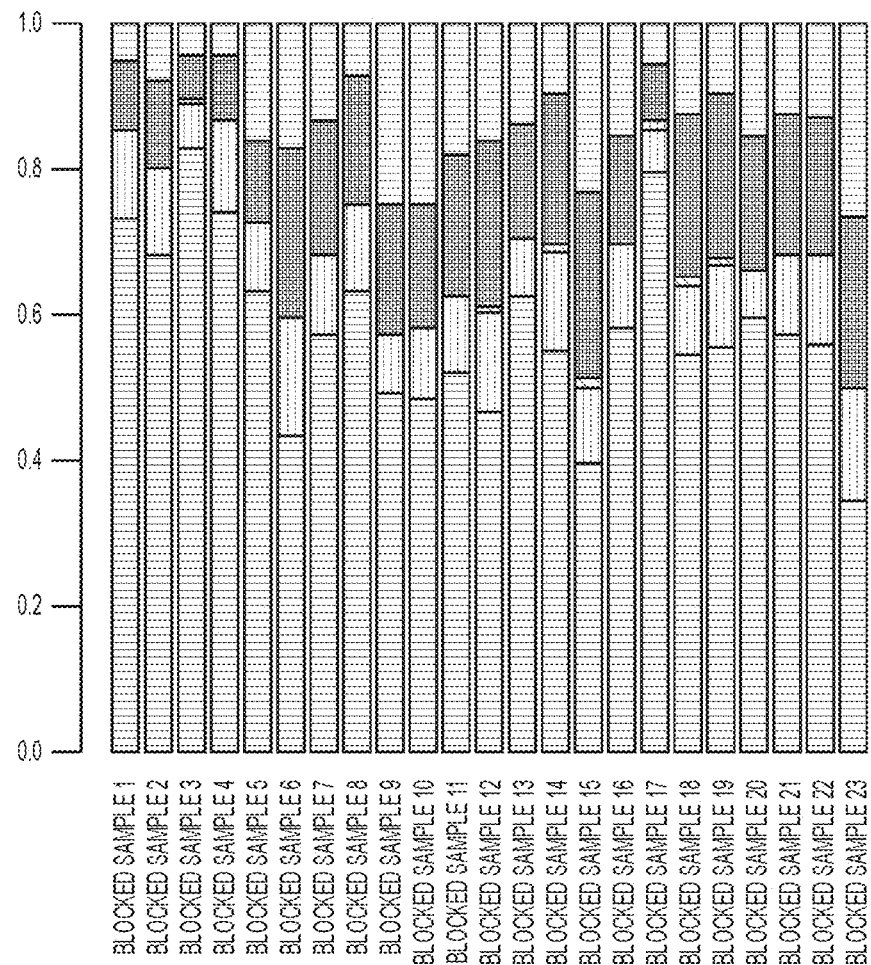
FIG. 9. Categorical distribution of reads from a set of hsa-miR-16-5p blocked human plasma libraries. The fraction of reads falling into six categories for 23 libraries derived from human plasma samples in which hsa-miR-16-5p was blocked is shown. Solid horizontal lines indicate reads aligning to miRNAs but not to hsa-miR-16-5p. Vertical broken lines indicate reads that map to the human genome but are not miRNAs. Vertical solid lines indicates reads aligning to hsa-miR-16-5p. Horizontal crosshatching indicates reads that align to the spike-ins. Checks are reads that failed to align to miRNAs or the human genome. broken horizontal lines are reads that are adaptor-dimer.

To demonstrate the efficacy of this approach, various concentrations of a blocker targeting hsa-miR-16-5p were titrated into library generation reactions using human heart total RNA as the input. Human heart total RNA is a suitable test sample since hsa-miR-16-5p is abundant in libraries derived from it, comprising ~10% of the miRNA reads. The effect on hsa-miR-16-5p read abundances in the final sequenced libraries shows dose-response behavior (FIG. 3), with a maximal effect in the 5-20 nM range. Furthermore, this blocking method was applied by using the hsa-miR-16-5p blocking oligonucleotide at 20 nM in a set of libraries derived from 23 human plasma samples. In the sequenced libraries, hsa-miR-16-5p was reduced to <1% of the reads in all cases (FIG. 9), far lower than in the previous set without blocking (FIG. 8).

Figure 10:
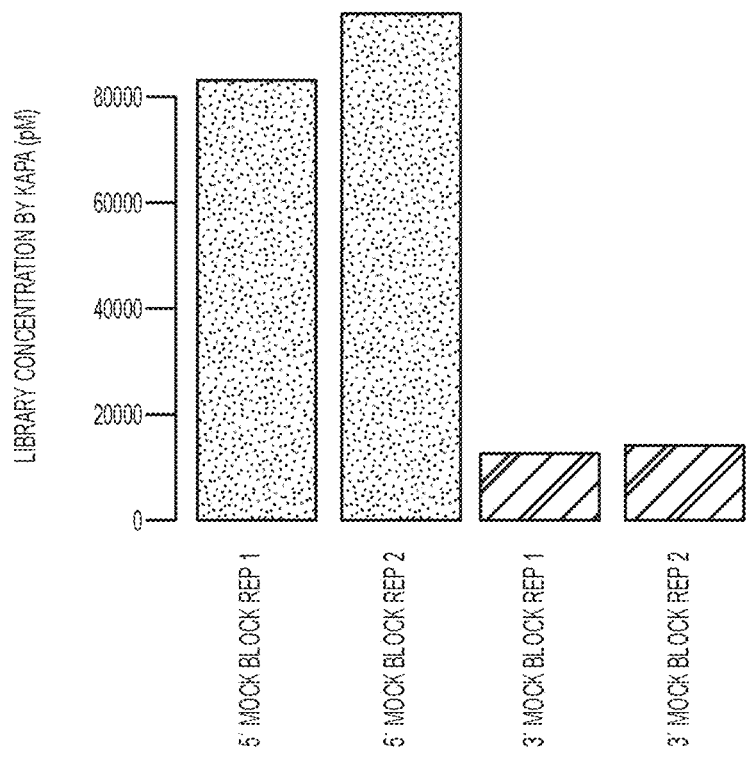
FIG. 10. Effect of the blocking ligation reaction when targeting the 5' end versus targeting the 3' end. Plotted is the total library concentration as determined using the Library Quantification Kit—Illumina/ABI Prism (KAPA Biosystems). The stippled bars are libraries in which a mock blocking ligation (all reagents except the blocking oligonucleotide) was run as would be performed to block the 5' end of a targeted miRNA. The crosshatched bars are libraries in which a mock blocking ligation was run as would be performed to block the 3' end of a targeted miRNA.
Figure 11:
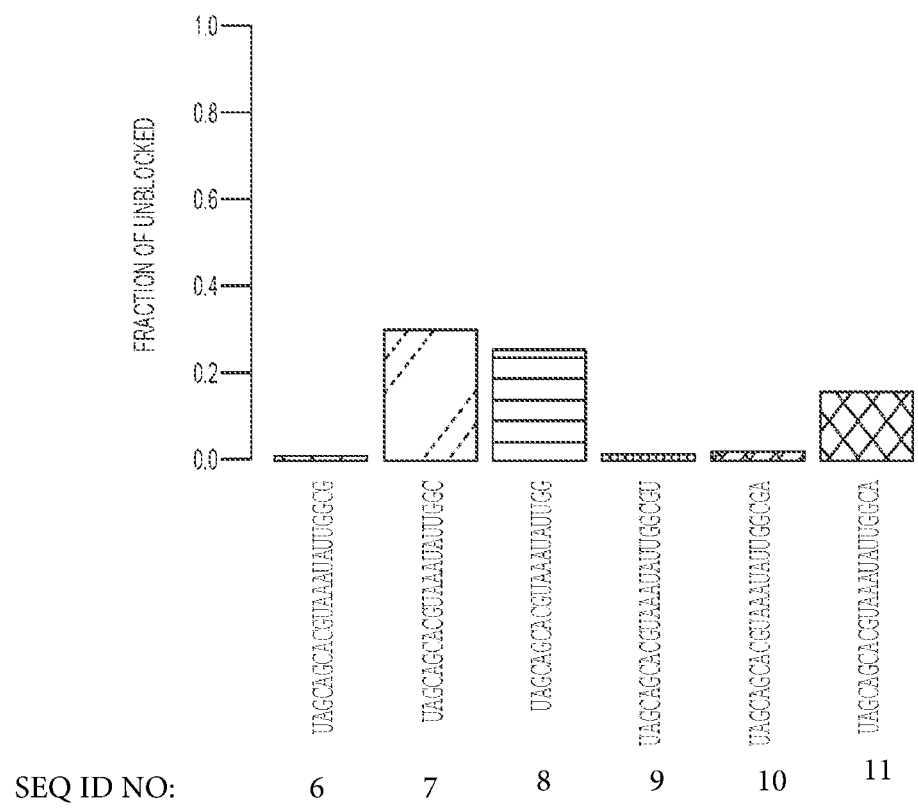
FIG. 11. Illustration of 3' end variations in hsa-miR-16-5p effects on blocking efficacy by a blocker targeting the 3' end. Shown are various sequence variants of hsa-miR-16-5p, with the canonical form displayed as the leftmost sequence. Together, the six plotted here comprise over 91% of the sequences aligning to hsa-miR-16-5p in this experiment. The bar height indicates the fraction remaining in the blocked library when compared to the unblocked library.
Figure 12A:
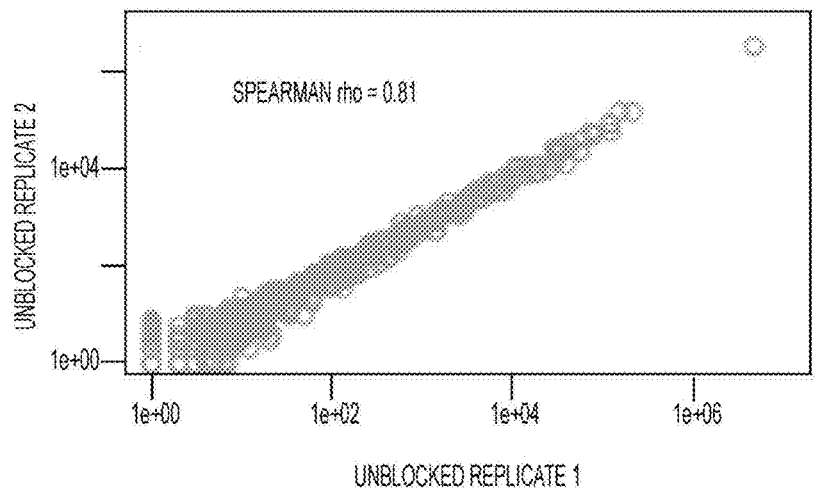
FIG. 12. Reproducibility of read counts in libraries with and without hsa-miR-16-5p blocking. (A-E) Read counts for replicate unblocked libraries from five human plasma samples are plotted versus each other. (F-J) Read counts for replicate hsa-miR-16-5p blocked libraries from five human plasma samples are plotted versus each other. For all experiments, the aligned reads were down-sampled to 6 million before plotting. The Spearman rho coefficient of correlation is shown for each replicate pair.
Figure 12B:
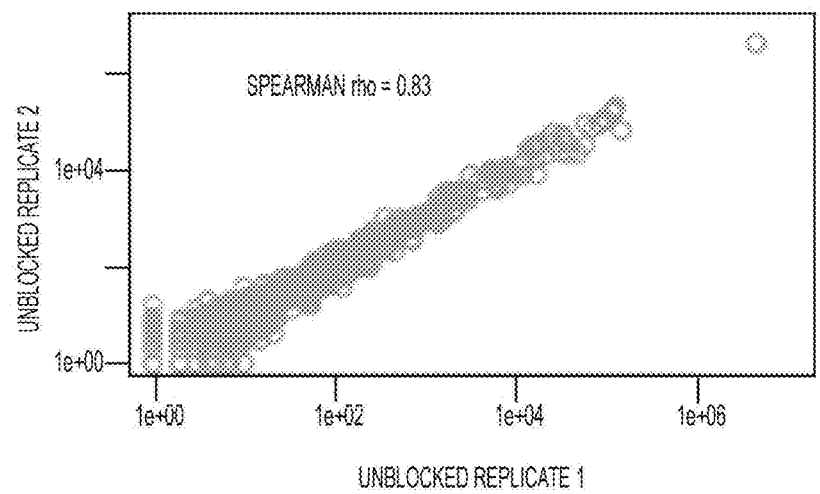
Figure 12C:
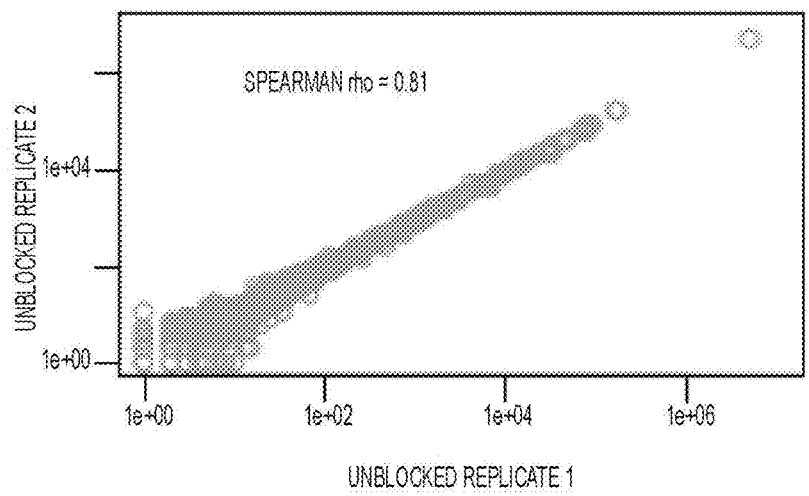
Figure 12D:
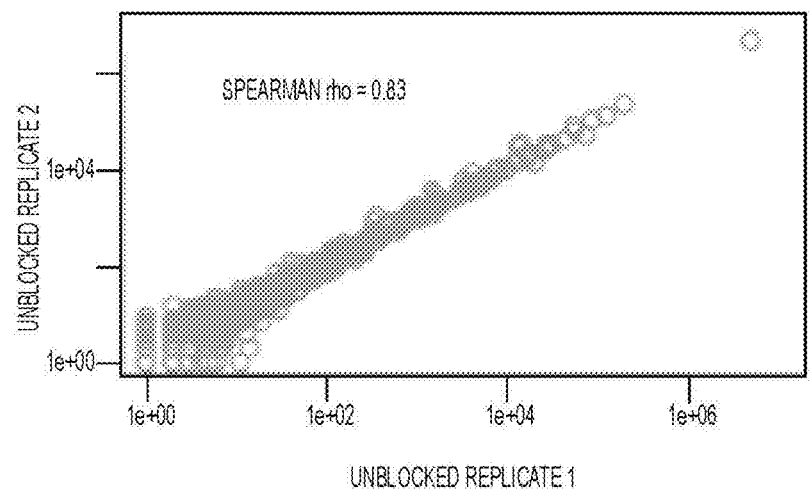
Figure 12E:
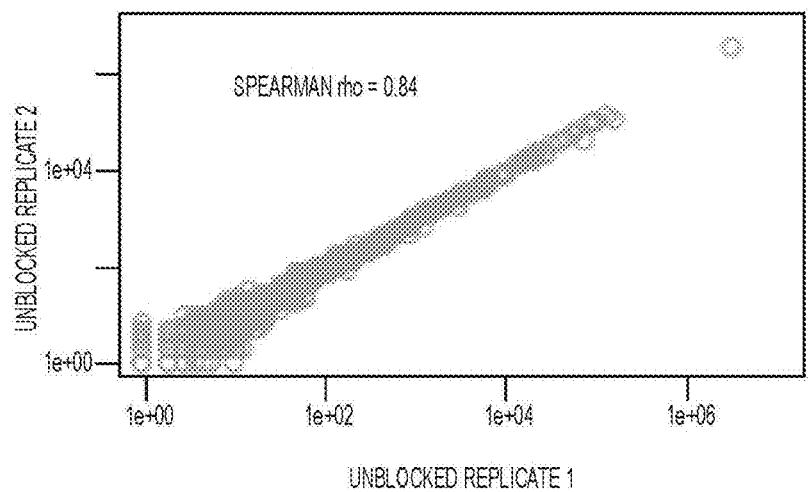
Figure 12F:
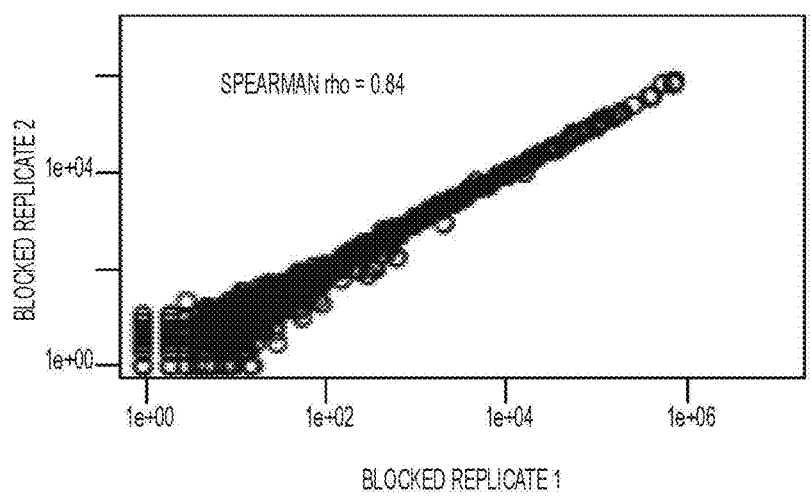
Figure 12G:
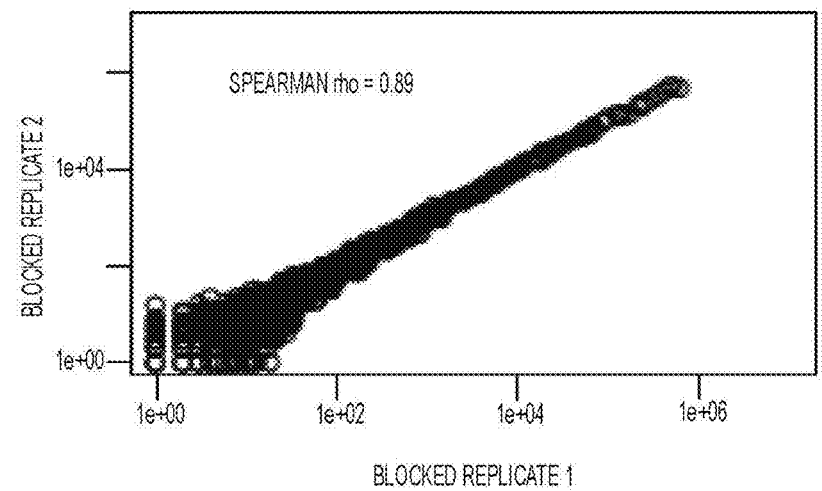
Figure 12H:
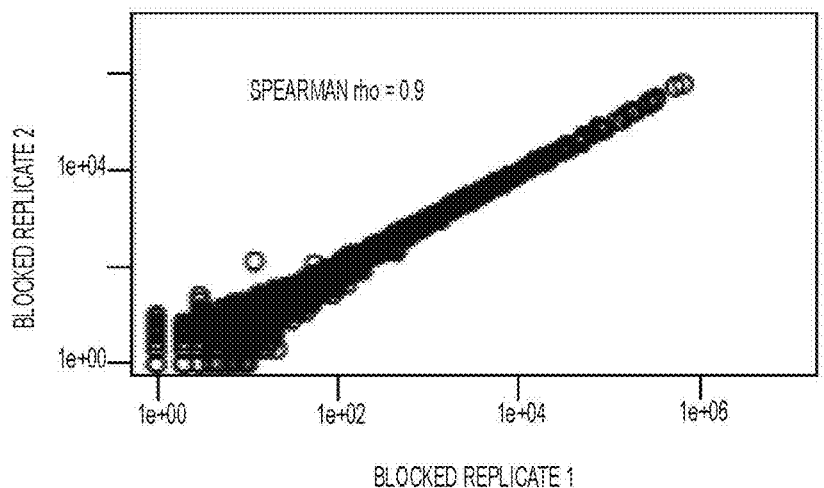
Figure 12I:
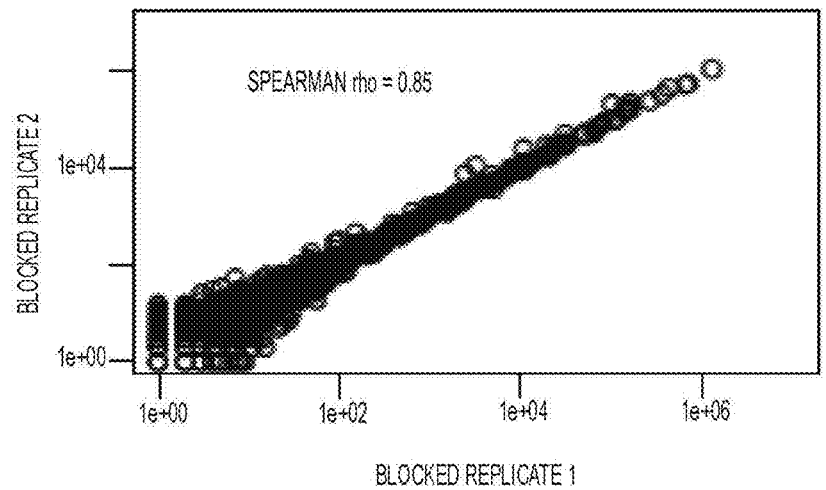
Figure 12J:
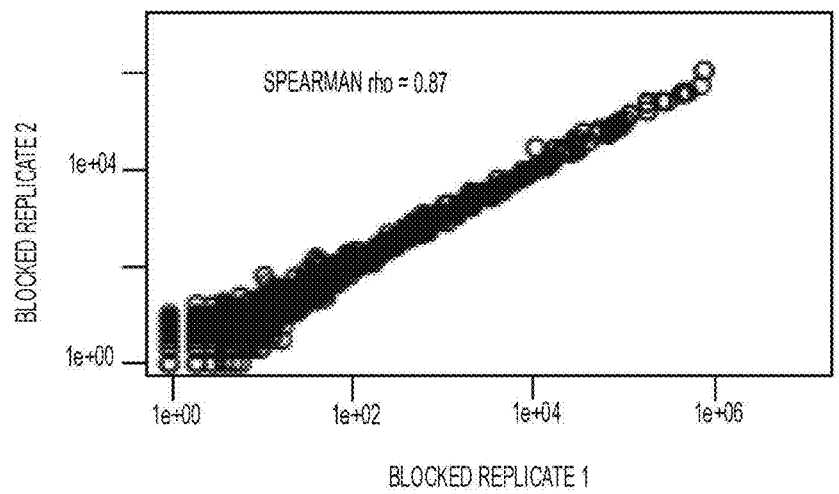
Figure 13:
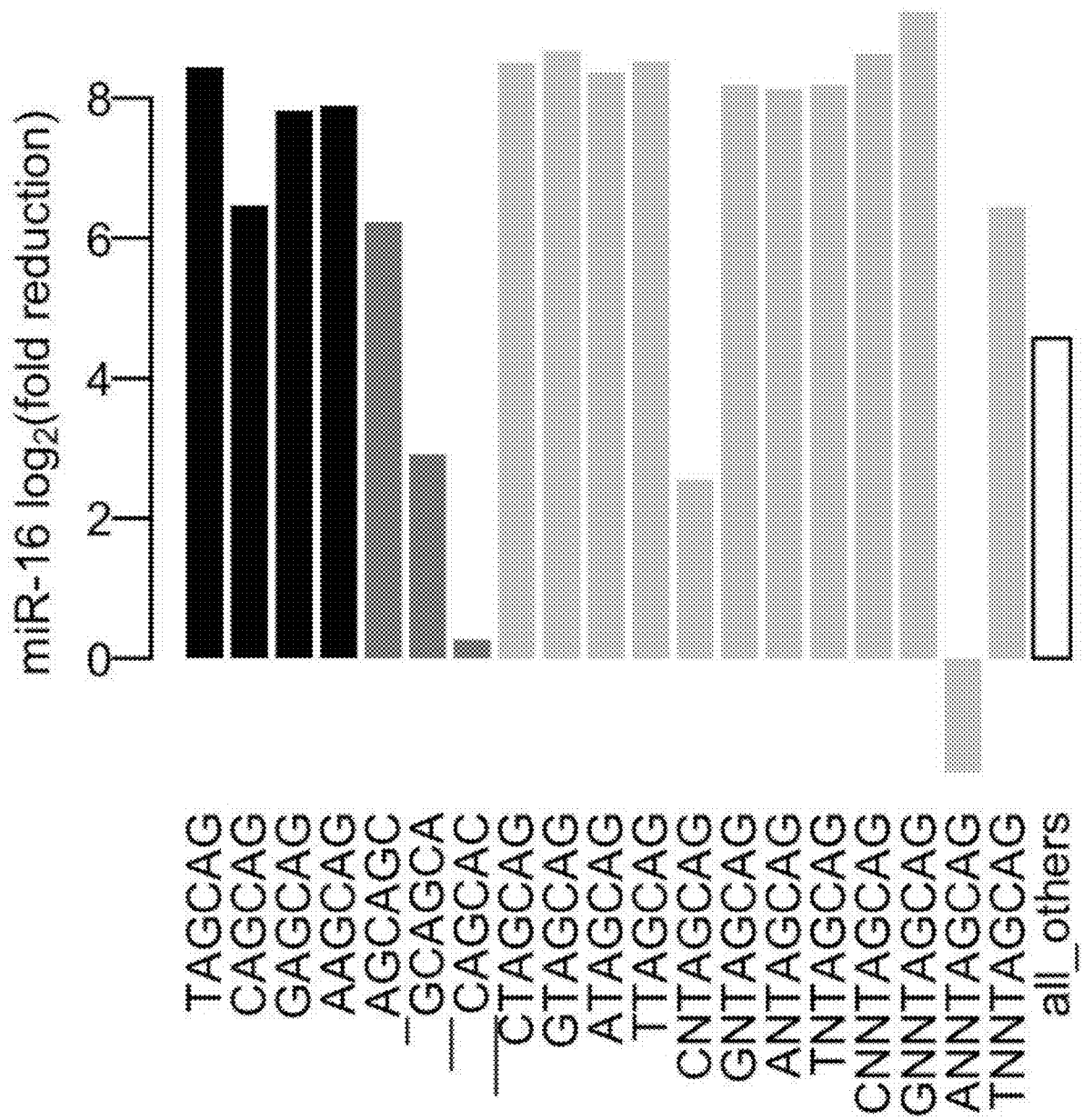
FIG. 13. Illustration of 5' end variations in hsa-miR-16-5p effects on blocking efficacy by a blocker targeting the 5' end. Shown are various sequence variants of hsa-miR-16-5p, with the canonical form displayed as the leftmost sequence. Underscores represent "missing" bases from the canonical form. Variants shorter than the canonical form, and certain longer forms show decreased blocking efficiency. Because these variants represent a very small fraction of the total reads (<2%), it is unclear if the base calls represent true variants or sequencing errors.

Because it was anticipated that targeting miRNAs at their 5' ends would lead to off-target activity due to sequence homology within miRNA families, it was initially attempted to target and block miRNAs from the 3' end. Analogous to the 5' approach, a hairpin oligonucleotide was used with a complementary 3' overhang, a 5' phosphate and 3' C3 blocker. The blocking ligation with T4 DNA Ligase occurs first, before the ligation of the adaptor to the 3' ends of the small RNA pool. Although this approach did effectively block hsa-miR-16-5p in human heart total RNA (data not shown), it had an adverse effect on the final library yields. In fact, even in libraries subjected to a mock blocking ligation reaction that included all reagents except the blocker oligonucleotide, this 3' approach yielded final library concentrations approximately five times lower than the 5' approach (FIG. 10). This decrease in yield in the 3' approach is likely due to the leftover ATP from the initial blocking ligation with T4 DNA Ligase inhibiting the truncated T4 RNA Ligase 2 in the subsequent ligation of the adaptor to the 3' ends of the small RNA pool. Although truncated T4 RNA Ligase 2 cannot turnover ATP, ATP can still bind to the remnants of the active site, leading to inhibition of the enzyme (personal communication with NEB). Thus, a 3' approach could likely be implemented without unwanted consequences if the reaction components of the blocking ligation were removed via column purification or some other suitable method. However, the fractional recovery of the small RNA from these methods can be low. Considering the intended application of this method to human plasma samples in which the RNA concentrations are already low, further reduction of the effective RNA input is undesirable. Furthermore, miRNAs are known to have considerable variation at their 3' ends due to differences in Dicer cut sites and non-templated nucleotide additions (42, 43). Because the approach relies on T4 DNA Ligase, which is sensitive to base-pair mismatches and gaps (44), these variations can adversely affect the efficacy of the blocking (FIG. 11). Although variation at the 5' end has similar effects on the 5' blocking approach (FIG. 13), 5' end variants generally represent a smaller fraction of the total. Considering these limitations of the 3' approach, it was decided to focus on the 5' approach for further studies.

Evaluating the Quantitative Performance of Blocked Libraries

To rigorously evaluate the effect of blocking hsa-miR-16-5p on the measurement of the non-targeted miRNA species in the library, libraries were generated from five human plasma samples. For each sample, two libraries were generated that were unblocked, that is, subjected to the blocking ligation reaction without a blocking oligonucleotide. Additionally, two libraries were generated using a blocking oligonucleotide targeting hsa-miR-16-5p, for a total of four libraries per sample. The plasma samples were chosen to have a high degree of hemolysis such that the blocking of hsa-miR-16-5p should have large effects.

Figure 4A:
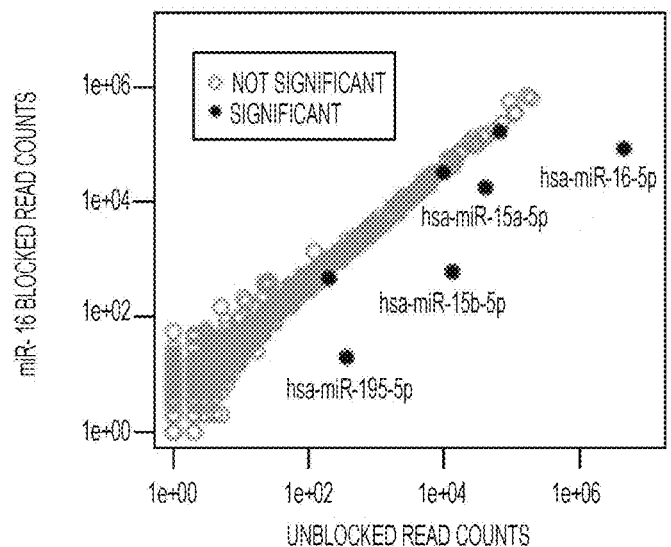
FIG. 4. Blocking of hsa-miR-16-5p in human plasma samples. (A-C) Sequencing results from five different human plasma samples are shown in A-E. Read counts from averaged (see Materials and Methods) replicate unblocked and hsa-miR-16-5p blocked libraries are shown on the x and y axes respectively. All libraries were down-sampled to 6 million aligned miRNA reads before plotting and analysis. A miRNA is considered significantly differentially expressed between the two conditions if the adjusted P-value as calculated by DESeq2 is <0.01. Not significantly differentially, expressed miRNAs are shown as open circles. Significantly differentially expressed miRNAs are shown as filled black circles. (F) Sequences of the mir-16 family members are shown with the seed region (bases 2-8) highlighted in gray.
Figure 4B:
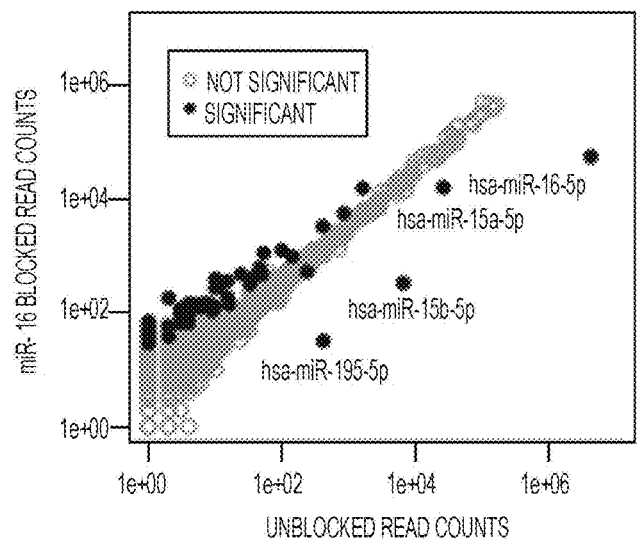
Figure 4C:
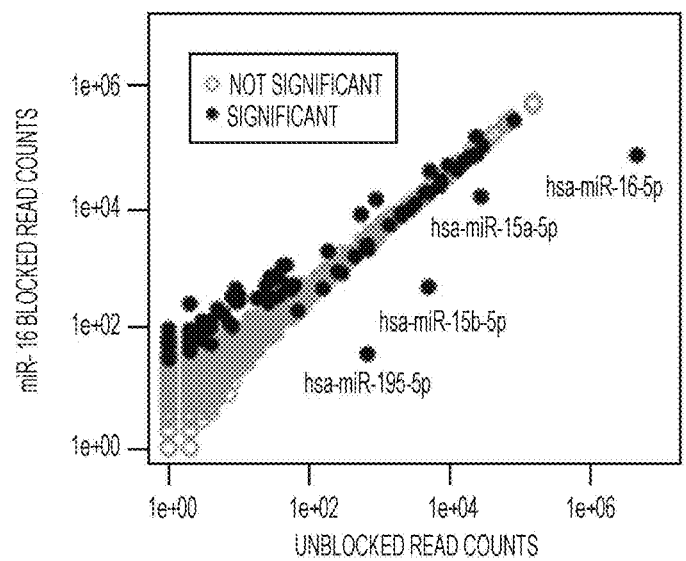
Figure 4D:
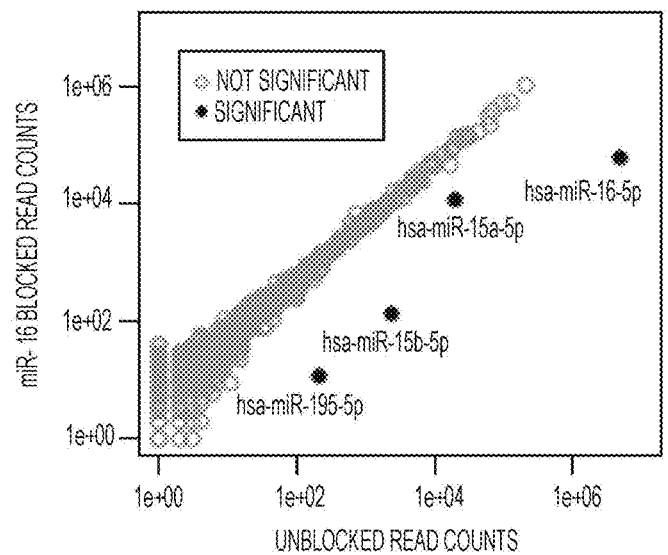
Figures 4E, 4F:
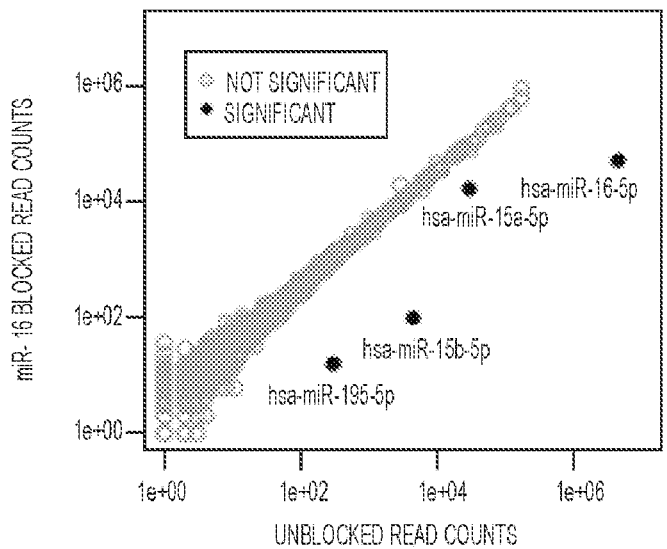

For each sample, the replicate unblocked and hsa-miR-16-5p blocked libraries were analyzed by using the application DESeq2 (see Materials and Methods) to establish those miRNAs differentially affected by the blocking. The analysis was limited to miRNA species alone because the accurate alignment of non-miRNA species was not universally precise enough to allow for meaningful comparisons. As expected, members of the mir-16 family are also blocked by this approach, due to sequence similarity at their 5' ends (FIG. 4A-E). Interestingly, mir-16 family members has-miR-424-5p and hsa-miR-497-5p are not blocked, likely because they have a cytosine in the first position rather than the uracil that the other four members have (FIG. 4D). This is consistent with the inability of T4 DNA Ligase to seal nicks at positions where a base pair mismatch is present at the nick site (44). It was observed that in two of the five samples, a small number of non-targeted miRNAs are significantly lower in the blocked libraries as well (FIG. 4A-C). Some of these miRNAs have several bases of sequence similarity with the blocker oligonucleotide and would form a duplex with a one-base gap between its 5' end and the 3' end of the blocking oligonucleotide. The inefficiency in sealing these gaps explains the moderate fold-changes. Other lowered species have no obvious sequence similarity. They are only significantly lower in one sample (FIG. 4C) and have small fold changes, suggesting that possibly the FDR correction used by DESeq2 did not sufficiently correct the multiple hypothesis effect. Several miRNAs are actually significantly higher in the blocked libraries (FIGS. 4B and C). Presumably, these miRNAs were able to be more effectively ligated during 5' adaptor ligation in the absence of the highly abundant and preferred ligation substrate hsa-miR-16-5p.

Figure 5:
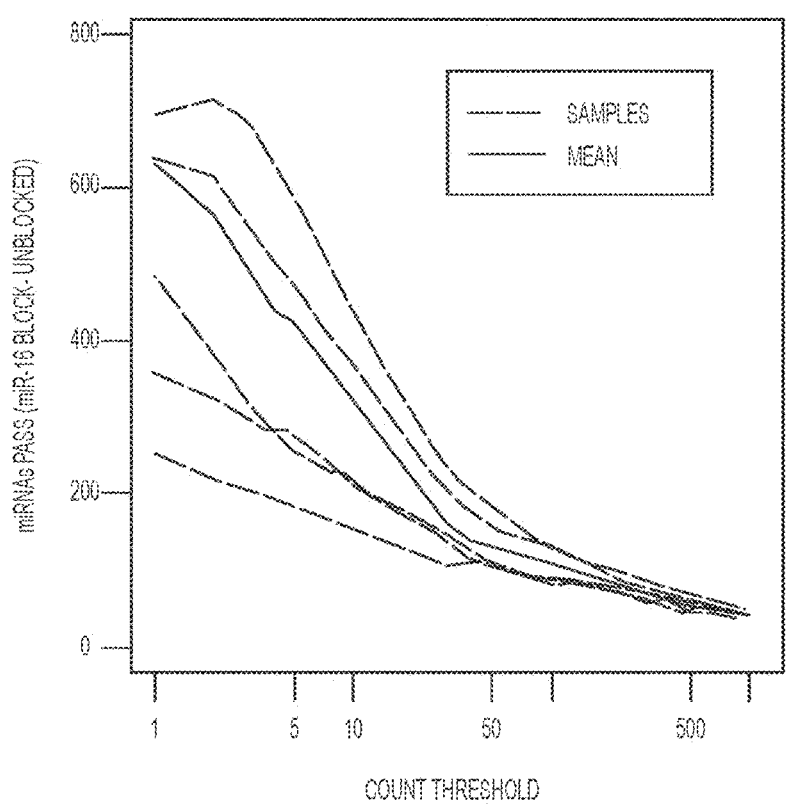
FIG. 5. Effect of hsa-miR-16-5p blocking on read depth in human plasma samples. A set of count thresholds is plotted on the x-axis versus the difference between the number of miRNAs passing that threshold in the hsa-miR-16-5p blocked samples versus the unblocked samples is plotted on the y-axis. The differences between individual samples are shown as gray dashed lines. The mean difference is shown as a solid black line. All libraries were down-sampled to 6 million aligned miRNA reads before plotting.

An important motivation for blocking hsa-miR-16-5p in these samples was to increase detection of the low abundance species. With a basis of an equivalent number of aligned reads, comparison of the unblocked libraries to the blocked libraries shows a marked increase in the number of miRNA species detected at a variety of count thresholds in all five plasma samples (FIG. 5). At a commonly chosen cutoff of 10 counts, between 180 and 450 more miRNAs are detected at this threshold in blocked samples compared to unblocked samples. This improvement in the detection of the low-abundance species was accomplished with negligible increase in library generation costs and no increase in sequencing costs.

A critical concern is that the blocking protocol adversely impacts the reproducibility of the measurement of less abundant miRNAs and by extension, the ability to precisely measure differential expression. While it is reassuring that the measured abundances of the vast majority of miRNAs are not affected by the blocking protocol (FIG. 4), it is important to note that given the known bias caused by the RNA ligases used in the library generation protocol, the absolute abundance of the miRNAs in the library does not represent a strictly meaningful measurement of the actual abundance in the sample. Nevertheless, the goal of many studies is to measure differential expression between sample groups. In these cases, the abundance of miRNAs needs only to be measured reproducibly.

Figure 6A:
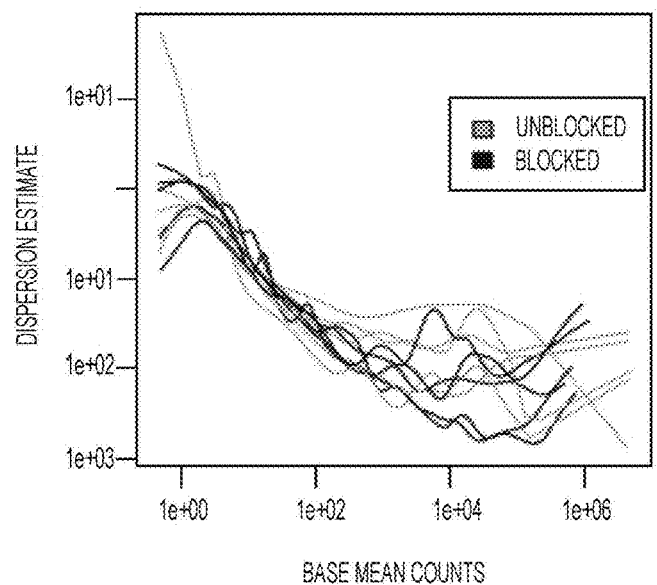
FIG. 6. Effect of hsa-miR-16-5p blocking on reproducibility and differential expression measurement in human plasma samples. (A) Dispersions were calculated for each set of plasma sample libraries based on the replicate unblocked libraries and replicate hsa-miR-16-5p blocked libraries using DESeq2. The dispersion values are plotted on the y-axis versus the base mean read counts, also calculated by DESeq2, on the x-axis. The unblocked dispersions are plotted in gray while the blocked dispersions are plotted in black. (B) Fold changes were calculated between all possible sample pairs (10) in both unblocked and hsa-miR-16-5p libraries. The $\log_2$ (fold changes) for all of those pairs are plotted on the same axes, with the $\log_2$ (fold change) for the unblocked library on the x-axis and the $\log_2$ (fold change) for the hsa-miR-16-5p blocked library on the y-axis. Thus each point represents a unique miRNA-sample pair combination. Only those miRNAs for which both samples had a DESeq2-calculated base mean >10 were plotted. The mean and standard deviation of the set of 10 Spearman rhos of the correlation of the fold changes between unblocked and hsa-miR-16-5p blocked libraries is listed on the plot.
Figure 6B:
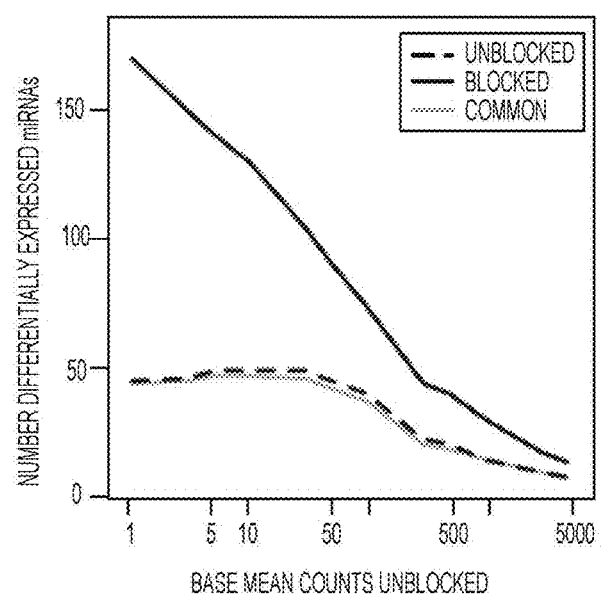

To assess the reproducibility of the five human plasma sample libraries, the Spearman rho coefficient of correlation was calculated between replicate libraries (FIG. 12). For all five samples, the Spearman rho was higher for the blocked. However there was concern that correlation may not be the best measure of reproducibility in these libraries because the biases introduced by the RNA ligases are consistent. Thus, correlation may be imposed upon a set of two libraries simply because they were subjected to the same bias. As an alternative, DESeq2 was used to estimate the dispersions of each library based on its replicates (see Materials and Methods). DESeq2 proposes a negative binomial distribution as the appropriate distribution for count data (41) and estimates the dispersion as function of read depth. As seen in the data, the dispersion is generally highest at low counts and decreases with increasing read depth (FIG. 6A). The blocked libraries show no greater dispersion in any count regime, and may be less dispersed, particularly in the middle-to-high count range.

Figure 21:
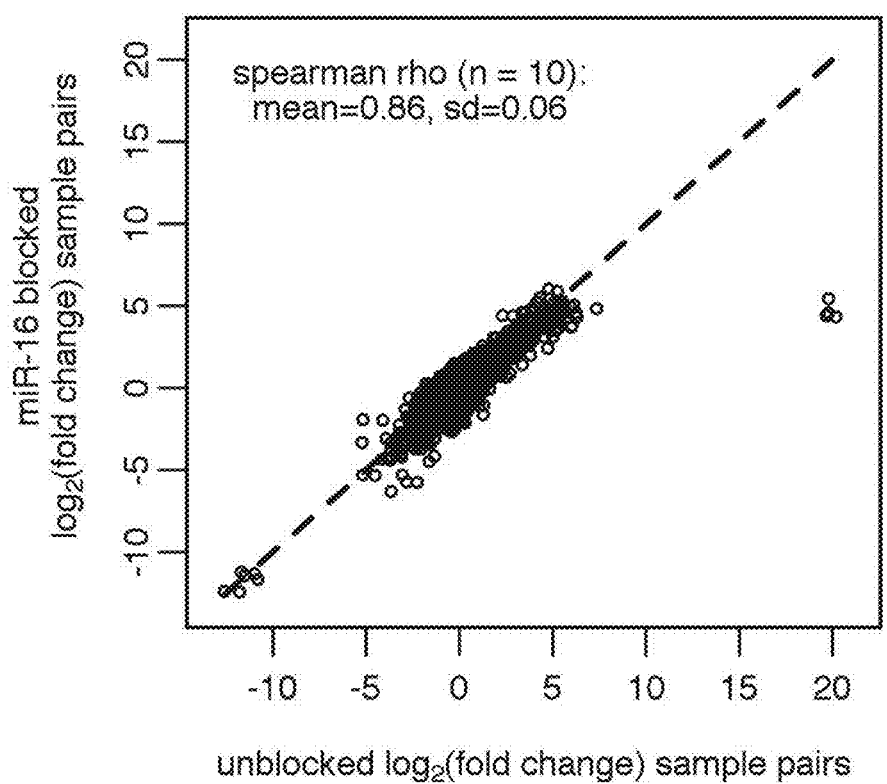
FIG. 21. Effect of hsa-miR-16-5p blocking on reproducibility and differential expression measurement in human plasma samples. Fold changes were calculated between all possible sample pairs (10) in both unblocked and hsa-miR-16-5p libraries. The $\log_2$ (fold changes) for all of those pairs are plotted on the same axes, with the $\log_2$ (fold change) for the unblocked library on the x-axis and the $\log_2$ (fold change) for the hsa-miR-16-5p blocked library on the y-axis. Thus each point represents a unique miRNA-sample pair combination. Only those miRNAs for which both samples had a DESeq2-calculated base mean >10 were plotted. The mean and standard deviation of the set of 10 Spearman rhos of the correlation of the fold changes between unblocked and hsa-miR-16-5p blocked libraries is listed on the plot.

Lastly, for blood-based biomarker studies, the ability to measure differential expression is paramount. Using DESeq2, the fold changes were calculated between all possible pairs of samples (10 pairs) separately in both the unblocked libraries and the hsa-miR-16-5p blocked libraries. The measurement of the fold change of miRNAs between two samples is highly similar in the unblocked and hsa-miR-16-5p blocked libraries (FIG. 21). With the exception of a few outliers, the vast majority of fold changes scatter around the unity slope line (dashed line in FIG. 21). The Spearman coefficient of correlation was calculated between the unblocked and hsa-miR-16-5p blocked libraries for each of the 10 pairs. The coefficient values were very high, with a mean of 0.86 (FIG. 21). These data indicate that the blocking of hsa-miR-16-5p has very little effect on the measurement of differential expression in this sample set.

Extension of the Blocking Technique to Other miRNAs and Multiplexing

Figure 7A:
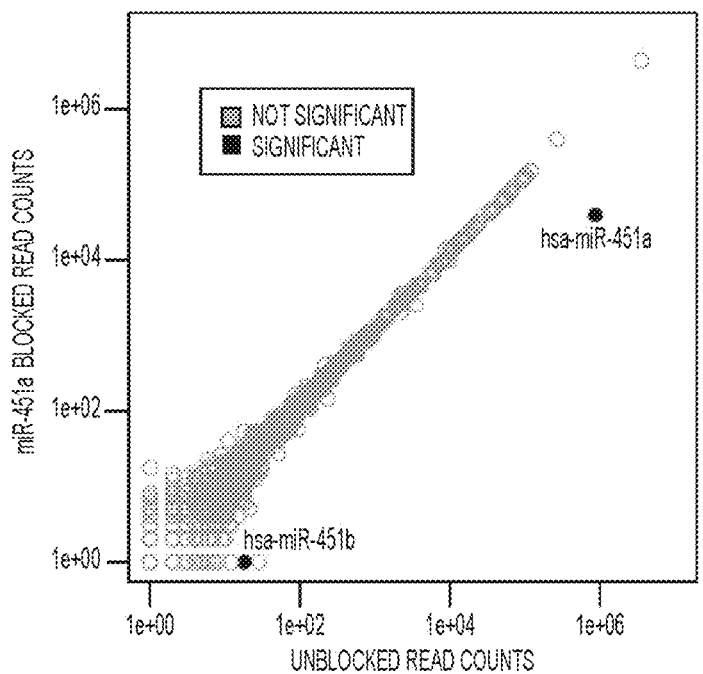
FIG. 7. Blocking of hsa-miR-451a alone and in concert with blocking hsa-miR-16-5p in human plasma samples. (A-B) Sequencing results from two human plasma samples are shown. Read counts from an unblocked library and a hsa-miR-451a blocked library are shown on the x and y axes respectively. (C-D) Sequencing results from the same two human plasma samples are shown. Read counts from an unblocked library and a hsa-miR-451a and hsa-miR-16-5p simultaneously blocked library are shown on the x and y axes respectively. A miRNA is considered significantly differentially expressed between the two conditions if the adjusted P-value as calculated by DESeq2 is <0.01 and if its base mean count is above 50. Not significantly differentially expressed miRNAs are shown as open circles. Significantly differentially expressed miRNAs are shown as filled black circles. All libraries were down-sampled to 6 million aligned miRNA reads before plotting and analysis.
Figure 7B:
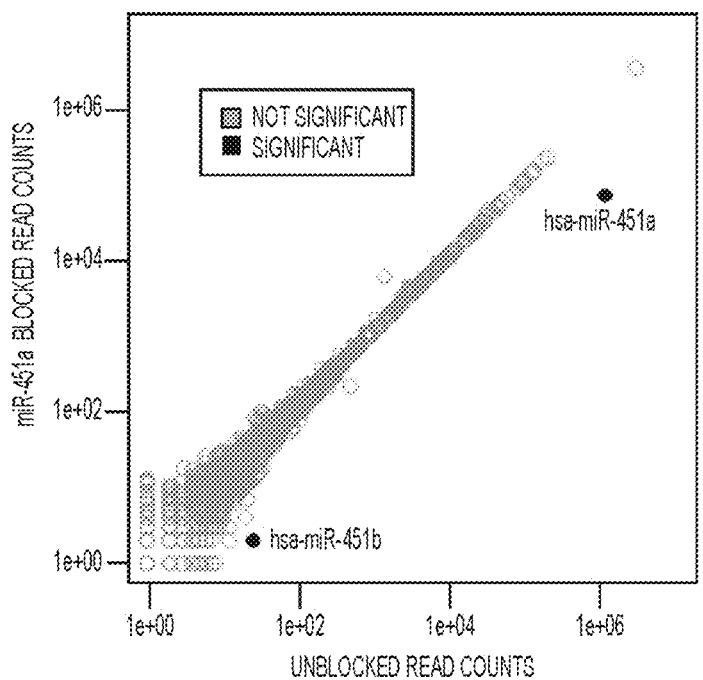

To establish the ability of the blocking method to block species other than hsa-miR-16-5p, hsa-miR-451a was blocked with an appropriately designed blocker oligonucleotide in a set of two human plasma samples. A selection of hsa-miR-451a was made because it is also abundant in the libraries prepared from human plasma samples and because it has been implicated to be derived from blood cells, like hsa-miR-16-5p (32). The analysis found hsa-miR-451a to be effectively blocked by this approach with minimal off-target effects (FIGS. 7A and B). Other than the intended target, hsa-miR-451a, only hsa-miR-451b was significantly affected by the blocking. Although the canonical mature form of hsa-miR-451b lacks significant sequence similarity to hsa-miR-451a, it was found that the reads mapping to the hsa-miR-451b hairpin actually aligned near its stem-loop portion and do show sequence similarity with the 5' portion of the hsa-miR-451a canonical mature form.

Figure 7C:
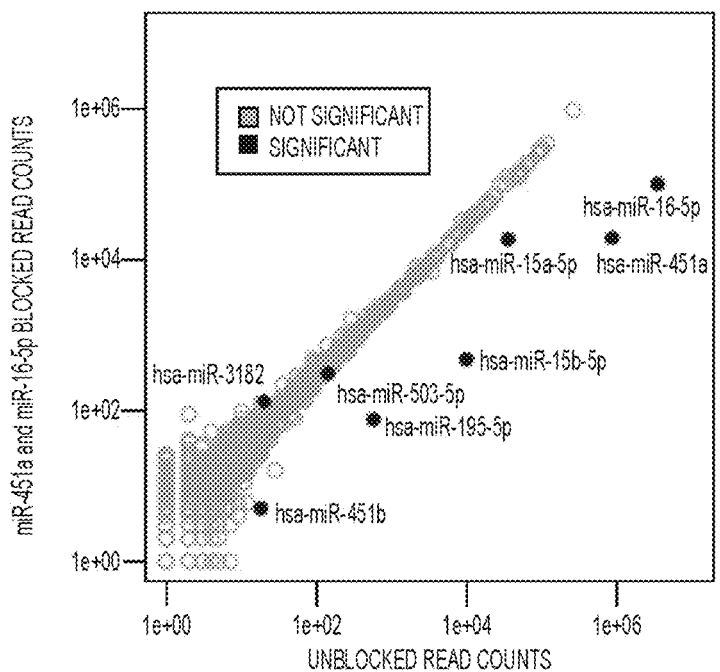
Figure 7D:
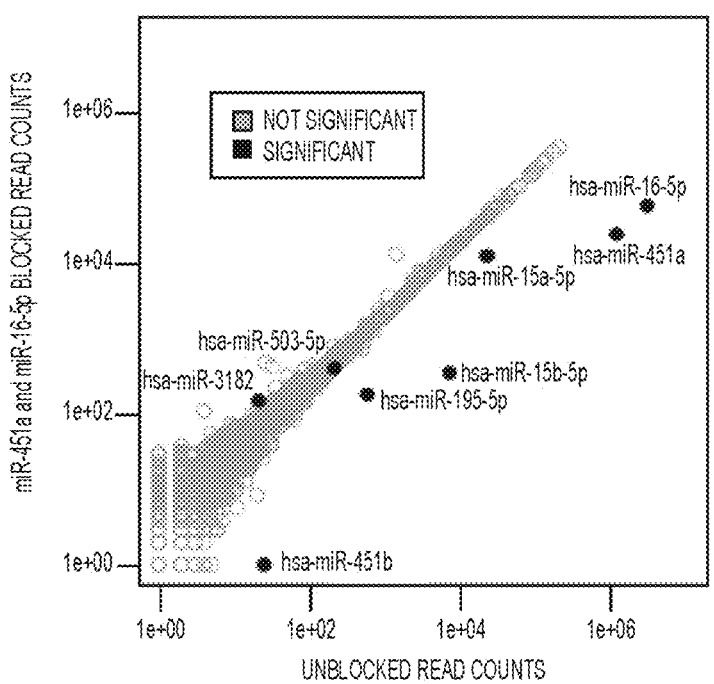

The ability to combine blocking oligonucleotides in a single blocking reaction would allow for reduction of a chosen set of miRNAs. Blocking oligonucleotides were combined targeting hsa-miR-16-5p and hsa-miR-451a into a single blocking reaction. The combination resulted in both blocking oligonucleotides behaving as they did when in isolation (FIGS. 7C and D). Other than the miRNAs expected to change based on the single blocker experiments, only hsa-miR-503-5p was significantly down regulated, albeit with a small fold-change. hsa-miR-503-5p shares seven bases of identical sequence with hsa-miR-16-5p on the 5' end. The combination of blocking oligonucleotides had no discernible effect on the total library yield. Overall, combining multiple blocking oligonucleotides seems to be a viable strategy. The extent to which blocking oligonucleotides can be multiplexed is the subject of future research.

DISCUSSION

Highly abundant and likely marginally informative miRNAs in NGS datasets from human serum or plasma hinder one's ability to discover true small RNA species functioning as biomarkers. This problem has been ameliorated by demonstrating a method to block miRNAs from representation in sequencing libraries. This method uses inexpensive reagents and requires no additional clean-up steps. Application of the method in human plasma samples resulted in a robust blocking of hsa-miR-16-5p, an abundant blood cell contaminant.

As a result of this blocking, the read depth of low abundance miRNAs was dramatically increased, leading to the detection of a greater number of species and a more accurate measurement of differential expression. Off-target effects do occur based on sequence homology at the targeted end of the miRNA, in this case the 5' end, especially within miRNA family members. However, these off-target effects are limited and predictable. The method does not decrease the reproducibility of the measurement of low abundance miRNAs and has no ill effects on the measurement of differential expression.

The approach has been generalized by targeting a second miRNA, hsa-miR-451a. Again, the performance of the blocking method on hsa-miR-451a is specific and has very small effects on non-targeted species. Additionally, the combination of two blocking oligonucleotides targeted to hsa-miR-16-5p and hsa-miR-451a in one blocking ligation reaction produced the same results seen by each one separately and without any interaction effects. This result implies the ability to combine several blocking oligonucleotides into a single reaction, although it remains to be tested.

It is anticipated that this technology could fill a role in small RNA sequencing similar to that which ribosomal RNA and globin RNA reduction methods have in messenger RNA sequencing. Although the research focused on small RNA sequencing in human plasma samples, the method could be useful in other tissue types as well. Custom pools of blocking oligonucleotides could be tailored to a particular application to maximize the use of sequencing resources. Also, even though the experimentation focused on the use of the Illumina platform, it is expected that this method would be applicable to other platforms as long as the library generation method relies on the ligation of adaptors directly to small RNAs. When it is anticipated that the small RNAs of interest will be rare and lowly expressed, as is likely true in many applications, the method offers a robust and cost-effective way to precisely measure them.

Supplemental Methods

Overview

This protocol describes the preparation of multiplexed (barcoded) libraries of miRNA from total RNA samples suitable for sequencing on the Illumina HiSeq and GAII platforms. The total RNA must be prepared by a technique that captures short RNA species (15nt-25nt). Acceptable techniques are phenol-chloroform extraction followed by ethanol precipitation or NorGen columns, amongst others. MicroRNA species in the samples have an adaptor oligo (referred to as the 3' adaptor) ligated to their 3' ends. Next a different oligo (referred to as the 5' adaptor) is ligated to the 5' end. The 3' adaptor provides a binding site for a complementary RT primer. This allows for cDNA to be made from the miRNA-adaptor complex via reverse transcription. The cDNA is then used as a template for several rounds of PCR. The PCR primers have long tails (~30 nt) that extend the length of the product. The tails contain the barcoding sequences (with an index read primer binding site), the Illumina sequencing primer site, and the Illumina cluster—generating sequences.

Considerations

The first step, the 3' ligation, is probably the most important step in the protocol. It hinges on the use of a truncated form of T4 RNA ligase. The truncation renders the enzyme unable to use ATP for energy and instead must use an already adenylated oligo as a substrate. Consequently, the 3' adaptor oligo is adenylated on its 3' end. If a fully functional RNA ligase capable of using ATP were used in this step, it would ligate the various RNA species present into concatamers, instead of only ligating the adaptor to the target RNA species. However, one must appreciate that all RNA species are targets, not just the miRNAs, leading to the formation of numerous unintended ligation products. Not only must these products be removed prior to sequencing, the other RNA species distract the adaptor from the miRNA population. Although it is difficult to calculate directly, the effective efficiency of ligation of the miRNAs present, in terms of the percent of miRNAs that actually get ligated to a 3' adaptor, is likely low. The 3' adaptor also has a 3-carbon spacer on its 5' end. This is to prevent RNA from being ligating to its 5' end in the subsequent 5' ligation reaction, which uses full length T4 RNA ligase.

Although the unintended ligation products that occur when an RNA molecule present in the sample other than a miRNA is ligated are somewhat problematic, the most problematic product formed in this protocol arises when unligated 3' adaptor is ligated to the 5' adaptor creating an adaptor dimer in the second ligation step.

This creates a short product that following PCR is highly complementary to the intended miRNA ligation product. In fact, they only differ by the internal ~22 bp of the miRNA. The adaptor dimer will hybridize efficiently to the intended miRNA product, making the separation of the two difficult. This problem is somewhat helped by hybridizing the RT primer to the 3' ligation product. Since the RT primer is complementary to the entire length of the 3' adaptor, the hybridization serves to bind some of the unligated 3' adaptor, preventing adaptor dimer formation in the 5' ligation reaction. While this technique reduces the formation of the adaptor dimer, much still persists and is present after PCR. It must be separated from the intended product by gel electrophoresis. However, because of the strong hybridization between the adaptor dimer and the intended miRNA product, the gel must be run under extremely denaturing conditions. To accomplish this, 10% acrylamide TBE-Urea gels are used. Furthermore, the gels are run in pre-heated buffer (90° C.). Although it is inconvenient to run the hot gels, the studies have shown that the 10% acrylamide TBE-Urea gels run at room temperature are not sufficiently denaturing for this application.

Detailed Procedure

General Notes

For those steps in which multiple components are added to the reaction, best practice is to make a "master mix" of the components sufficient for all reactions being performed. The samples throughout the course of the protocol should always be kept on ice or at ice temperature when not being otherwise incubated. In the development of this protocol, the samples were kept in a metal block that was kept cool in a refrigerator when not in use. (For simplicity, the protocol will say "on ice", however.) Furthermore, the T4 RNA Ligase 2, truncated; the RNAse Inhibitor, murine; the T4 RNA Ligase 1, the SuperScript II, and the Phusion PCR Master Mix should all be kept on ice. In the following step, "STOPPING POINT" is written at points where the protocol can be stopped overnight. This protocol can be completed in 3 days. If the precipitation overnight incubations at −30° C. are shortened to 2 hour incubations at −80° C., the protocol can be done in 2 busy days.

3' Ligation

1. Prepare the following stock buffer, called "2×3" Ligation Buffer. This recipe is sufficient for many reactions and does not need to be prepared fresh each time the protocol is run. Store at −20° C. between uses:

250 μL 50% PEG 8000 (from T4 RNA Ligase 1 kit)
200 μL 10×T4 RNA Ligase Buffer (from T4 RNA Ligase 1 kit) 550 μL DNAse, RNAse free water 2. Make a stock solution of the spike-in controls. Make a large batch suitable for multiple runs of this protocol. Store at −80° C. The concentrations listed here are suitable for human plasma samples. However, it is expected that the total input of the spike-ins will need to be adjusted for different sample types.

Final Concentrations:
20 μM miRNASeq Multiplex 22 bp Spike In 2 μM miRNASeq Multiplex 25 bp Spike In
0.2 μM miRNASeq Multiplex 20 bp Spike In 3. Combine the following in a 0.2 mL PCR tube.
   1 μL 10 uM miRNASeq Multiplex 3' Adaptor 1 μL Spike In stock (from step 2)
   4 μL of total RNA 4. Gently mix by flicking the tube and spin down the tube in a tabletop mini-centrifuge. Incubate for 2 min at 70° C. in a pre-heated thermal cycler. Immediately chill on ice following incubation.

5. To each sample add the following: 10 µL 2×3' Ligation Buffer

2 µL T4 RNA Ligase 2, truncated 1 µL RNAse Inhibitor, murine

6. Gently mix the components and spin down. Incubate for 1 hour at 25° C. in a thermal cycler. (Note: Incubation times longer than 1 hour have been shown to produce undesired products.)

Blocking Ligation

1. Pre-anneal the blocking oligonucleotide (do this every time). Incubate a 0.5 µM blocking oligonucleotide stock in 1×T4 DNA Ligase buffer as follows:

95° C. for 5 min, 65° C. for 5 min, 55° C. for 5 min, 45° C. for 5 min, 35° C. for 5 min, 25° C. for 5 min, 4° C. for infinity.

2. Make a master mix of the following:

1 µL of pre-annealed blocking oligonucleotide working stock 1 µL of 10 mM ATP

1 µL of T4 DNA Ligase

3. Add 3 µL of the above master mix to each 3' ligation reaction.

4. Incubate at 30° C. for 1 hr followed by 65° C. for 10 min and hold at 4° C.

RT Primer Hybridization, and 5' Ligation

1. To the 3' ligation product, add 1 µL of 10 uM miRNASeq Multiplex RT Primer. Incubate as follows in a thermal cycler: 75° C. for 5 min, 37° C. for 30 min, 25° C. for 15 min, 4° C. for inf 2. While the samples are incubating, thaw the 20 uM miRNASeq Multiplex 5' Adaptor. Once thawed, incubate the adaptor at 70° C. for 2 min and then immediately chill on ice.

3. A pool of 4 5' adaptors is used in the next step. These are an equimolar mix of miRNASeq Multiplex 5' Adaptor Mod 1, 2, 3, and 4 at 5 uM final concentration each, for a total adaptor concentration of 20 uM.

4. When the samples are finished incubating, transfer them to ice. Add the following:

0.64 µL T4 RNA Ligase 1

1 µL RNAse Inhibitor, murine 0.86 µL RNAse, DNAse free water

1 µL 20 uM miRNASeq Multiplex 5' Adaptor Mod pool 1 µL 10×T4 RNA Ligase Buffer (T4 RNA Ligase 1 kit) 1 µL 10 mM ATP (T4 RNA Ligase 1 kit)

5. Mix gently and spin down briefly. Incubate the samples for 1 hour at 25° C. in a thermal cycler. STOPPING POINT (The samples can be placed in −80° C. and left overnight after this step, although it is ideal to take the samples through reverse transcription before stopping)

Reverse Transcription and PCR

1. Setup the following reaction. The protocol up this point has generated ~26.5 µL of ligated product. Only 11 µL of the product is carried forward, so that the remainder is available for a repeat if needed. The unused product should be stored at −80° C.

4 µL 5×FS Buffer (SuperScript II kit) 2 µL 0.1 M DTT (SuperScript II kit)

1 µL Deoxynucleotide Mix (10 mM each) 1 µL RNAse Inhibitor, murine

1 µL SuperScript II (SuperScript II kit)

11 µL ligation product (from previous step)

2. Incubate the samples in a thermal cycler as follows: 42° C. for 50 min

70° C. for 15 min 4° C. for inf

3. Add the following to each sample:

25 µL Phusion High-Fidelity PCR Master Mix 2.5 µL 20 uM miRNASeq Multiplex R Primer To each individual sample add 2.5 µL of one of the twelve different indexed miRNASeq Multiplex F Primers at 20 uM, being sure to note which sample received which barcoded primer. Mix the samples and spin down.

4. Incubate the samples in a thermal cycler as follows: 94° C. for 30 s 15 cycles of: 94° C. for 10 s 72° C. for 45 s 65° C. for 5 min 4° C. for inf STOPPING POINT (The samples can be stored at −20° C.) Concentration, Gel Separation, and Purification The gels run in this protocol are the Mini-PROTEAN format from BioRad and run in the Mini-PROTEAN Tetra Cell gel system. It is expected that using a different gel system would require that extensive modifications be made to this protocol.

1. Transfer each sample to a 1.7 mL microcentrifuge tube. Add 250 µL of Buffer PB (MinElute Kit). Mix well and transfer to a MinElute column placed in a 2 mL collection tube. Centrifuge for 1 min at max speed. Discard flow through.

2. Add 750 µL of Buffer PE (MinElute kit, ensure ethanol has been added) to the MinElute column. Centrifuge for 1 min at max speed. Discard flow through and place column back into the same collection tube. Centrifuge again for 1 min at max speed.

3. Transfer the column to a clean 1.7 mL microcentrifuge tube. Add 17.5 µL of RNAse, DNAse free water. Let stand for 5 min. Centrifuge for 1 min at max speed. Discard column, keeping the flow through in the microcentrifuge tube.

4. To each sample, add 17.5 µL of 2×TBE—Urea Sample Buffer. Mix well and spin down. Set the samples aside at room temperature.

5. Prepare DNA ladder working solutions. This recipe makes enough for several runs and need not be made fresh. Store at 4° C.

20 bp Ladder

200 µL 2×TBE-Urea Sample Buffer 180 µL DNAse, RNAse free water

20 µL 20 bp DNA Ladder stock solution (Bayou BioLabs)

100 bp Ladder

200 µL 2×TBE—Urea Sample Buffer 190 µL DNAse, RNAse free water

10 µL 100 bp DNA Ladder stock solution (NEB)

6. At this point in the protocol, a hot gel will be run. Since this involves using nea-boiling TBE buffer, extreme caution should be used. Additionally, protective equipment such as aprons and gloves should be worn.

7. Preheat a heating block to 95° C.

8. Make 1×TBE buffer from 10×TBE buffer stock. Make 1 liter, sufficient for one or two gels. A single gel, can accommodate four samples with no spacer lane between samples. Each sample will be split and run in two lanes to avoid interference from the adaptor dimer. It is not recommended to run more than two gels at a time.

9. Pre-warm 10% TBE-Urea Mini-PROTEAN gel(s) in hot tap water (no hotter than what comes out of the tap). Leave them in their packaging and weigh them down so they don't float. Also, warm the gel holder in the water.

10. In a microwave, heat 900 mL of 1×TBE buffer split into aliquots of 450 mL in two 500 mL Pyrex beakers with Saran wrap partially covering the top to 80-85° C. Heat in increments of 2-5 min (depending on microwave power).

Between heating increments, carefully stir the buffer with a thermometer and check the temperature. Do not boil the buffer.

11. When the heating of the buffer is nearing completion, place the samples into the preheated heating block at 95° C. Also place the 20 bp and 100 bp working solutions in the heating block. Ensure that every sample resides at 95° C. for at least two minutes before it is loaded onto the gel. It is not detrimental for the samples to remain in the heating block for more than 2 min, up to ~30 min.

12. Remove the gels and gel holder from the warm water. Remove the gels from their packaging, ensuring to remove the green tape at the bottom of the gel and the lane comb. Assemble the gels in the gel holder.

13. Pour the now hot 1×TBE buffer (80-85° C.) into the gel assembly, filling it to the top.

14. With a p20 set to 15 µL, pipet up and down in each well of the gel. This is to remove any urea that often crystalizes in the wells during storage. Remove any bubbles in the wells.

15. Remove the two ladder tubes (carefully, they are hot). Spin them down briefly in a tabletop mini centrifuge. Add 15 µL of the 20 bp ladder to lane 1 of the gel, pipetting carefully to avoid contamination of other lanes. The tube may make a "pop" when opened. Add 15 µL of the 100 bp ladder to lane 2.

16. Remove a pair of sample tubes from the heating block. Spin them down briefly in a tabletop mini centrifuge. Load two 15 µL aliquots of each sample into two adjacent lanes of the gel. Repeat for all of the samples. Work quickly because the gel is cooling, but carefully and deliberately.

17. Once all the samples are loaded, gently place the gel assembly into the gel box. Re-heat the remaining 1×TBE buffer to 90° C. in the microwave. Pour all the remaining 1×TBE into the gel box (not inside the gel assembly).

18. With a 10 mL pipet, top-off the buffer inside of the gel assembly with buffer in the gel box, filling it as near to the top as possible. This is important because the hot buffer will evaporate during the course of the run.

19. Begin running the gel at 200V. Closely monitor the current. If the current begins to rise more than 10 mA from the initial current (this is likely to happen), turn the voltage down 10V to 190V. Continue to monitor the current and adjust the voltage lower until the current stabilizes. However, do not run the gel below 160V. The current rises because the gel and buffer are hot. The conductivity of the system is much higher than when run at room temperature. The increased conductivity allows more current to flow, which in turn heats the gel, further increasing conductivity, and creating a positive feedback loop. Thus, the current must be monitored closely during the run. Under these conditions, the gel should be run for 45 minutes.

20. Turn off the power source and disassemble the gel box. Allow the gels to cool on the bench top prior to opening their plastic cases. While the gels are cooling, for each gel, add 50 mL of 1×TBE to a suitably sized gel staining container. Add 5 µL of SYBR Gold 10,000× stock to each 50 mL TBE aliquot and mix. Wrap the container in aluminum foil to protect it from light. Open the plastic case of the now cooled gel and place the gel into the staining container with the TBE and SYBR Gold. Re-cover the container with the aluminum foil and rock on a gel rocker for 10 minutes.

21. While the gel is staining, prepare the following for each sample. With a 20-gauge needle, poke a hole in the bottom of a 0.5 mL microcentrifuge tube. Place this tube into a 1.7 mL centrifuge tube.

22. Place a sheet of Saran wrap on a UV-transilluminator. Transfer the gel from the staining solution onto the Saran wrap sheet. Capture an image of the gel under UV illumination with an appropriate gel visualization system (i.e. UVP EC3 Imaging System).

23. Transfer the gel by picking up the Saran wrap to a UV-transilluminator that can be accessed for subsequent gel excision steps (maybe the same as where the image was taken). With razor blades and forceps, carefully excise the 135 bp band for each sample. Since each sample was loaded in two aliquots in adjacent lanes, cut both bands from the same sample out together. Replace the razor blades and forceps after every time they touch the gel to avoid cross-contamination. Place the gel fragments into the 0.5 mL microcentrifuge tube with the hole in the bottom.

24. Transfer the 0.5 mL microcentrifuge tubes nested in 1.7 mL microcentrifuge tubes containing the gel pieces into a microcentrifuge. Spin at max speed for 1 min. The gel fragment should be in the bottom of 1.7 mL microcentrifuge tube in small pieces. If some of the gel fragment is retained in the 0.5 mL, spin at max speed for another minute.

25. Prepare the following stock, called "Soaking Solution". This recipe makes enough for many samples as does not need to be prepared fresh every time. Store at room temperature.

2 mL 5M Ammonium Acetate 2 mL 1% SDS solution
4 µL 0.5M EDTA
16 mL RNAse, DNAse free water 26. Add 300 µL of the Soaking Solution to each sample. Incubate with agitation at 70° C. for 2 hours.

21. Transfer each sample (including gel pieces) to a Spin-X Centrifuge Tube Filter, 0.22 urn Cellulose Acetate, sitting in its accompanying microcentrifuge tube. Spin in a microcentrifuge at max speed for 1 min.

28. Transfer the flow-though to a new 1.7 mL microcentrifuge tube. Add 1 µL of 10 ug/µL glycogen. Add 300 µL of 100% isopropanol. Vortex and spin down briefly. Incubate overnight at −30° C. STOPPING POINT (The samples can be kept in the precipitating conditions at −3° C. for several days.)

29. Spin the samples in a refrigerated centrifuge (4° C.) for 20 min at 14,000 rpm (max speed). Again, place the hinges of the tubes outward so that the location of the pellet in predictable.

30. While the samples are in the centrifuge, chill an aliquot of 80% ethanol by place in it in ice water or by some other suitable method.

31. After centrifugation, pipet off the supernatant. Using a p200, place the tip of the pipet near the bottom of the tube away from the hinge side and gently remove the liquid. Add 100 µL of the chilled 80% ethanol and centrifuge again in a refrigerated centrifuge (4 C) for 10 min at 14,000 rpm (max speed).

32. Again carefully remove the supernatant with the p200 as described above. After removing as much as possible with the p200, use a p20 to get the remainder, leaving behind as little liquid as possible.

33. Resuspend the pellet in 10 µL of EB buffer (MinElute Kit). Measure the concentration of the sample with a suitable method (QBit HS DNA is preferred with 1 µL of sample input). The sample is ready for sequencing. Typically, this protocol yields 10 µL of 1-4 ng/µL product, depending on sample input mass and sample type. Although it depends on the level of multiplexing, 0.5 ng/µL or higher libraries are concentrated enough for sequencing. If a lower yield is expected, the pellet can be resuspended in a lower volume to yield a higher concentration product.

It is highly recommended to run KAPA qPCR to quantify library concentrations before sequencing.

REFERENCES

1. Ivey, K. N. and Srivastava, D. (2010) MicroRNAs as regulators of differentiation and cell fate decisions. *Cell Stem Cell*, 7, 36-41. 2. Hu, H. and Gatti, R. a. (2011) MicroRNAs: new players in the DNA damage response. *J. Mol. Cell Biol.*, 3, 151-158. 3. Carleton, M., Cleary, M. A. and Linsley, P. S. (2007) MicroRNAs and cell cycle regulation. *Cell Cycle*, 6, 2127-2132. 4. Wilson, R. C. and Doudna, J. A. (2013) Molecular mechanisms of RNA interference. *Annu. Rev. Biophys.*, 42, 217-239. 5. Fabbri, M., Paone, A., Calore, F., Galli, R., Gaudio, E. and Santhanam, R. (2012) MicroRNAs bind to Toll-like receptors to induce prometastatic inflammatory response. *Proc. Natl. Acad. Sci. U.S.A.*, 109, E2110-E2116. 6. Place, R. F., Li, L.-C., Pookot, D., Noonan, E. J. and Dahiya, R. (2008) MicroRNA-373 induces expression of genes with complementary promoter sequences. *Proc. Natl. Acad. Sci. U.S.A*, 105, 1608-1613. 7. Dumortier, O., Hinault, C. and Van Obberghen, E. (2013) MicroRNAs and metabolism crosstalk in energy homeostasis. *Cell Metab.*, 18, 312-324. 8. Jin, Y., Yang, C.-J., Xu, X., Cao, J.-N., Feng, Q.-T. and Yang, J. (2015) MiR-214 regulates the pathogenesis of patients with coronary artery disease by targeting VEGF. *Mol. Cell. Biochem.*, 402, 111-122. 9. Santa-maria, I., Alaniz, M. E., Renwick, N., Cela, C., Fulga, T. a, Van Vactor, D, Tuschl, T., Clark, L. N., Shelanski, M. L., Mccabe, B. D. et al. (2015) Dysregulation of microRNA-219 promotes neurodegeneration through post-transcriptional regulation of tau. *J. Clin. Invest.*, 125, 681-686. 10. Heneghan, H. M., Miller, N., McAnena, O. J., O'Brien, T. and Kerin, M. J. (2011) Differential miRNA expression in omental adipose tissue and in the circulation of obese patients identifies novel metabolic biomarkers. *J. Clin. Endocrinol. Metab.*, 96, 846-850. 11. Mall, C., Rocke, D. M., Durbin-Johnson, B. and Weiss, R. H. (2013) Stability of miRNA in human urine supports its biomarker potential. *Biomark Med.*, 7, 1-17. 12. Wang, K., Zhang, S., Weber, J., Baxter, D. and Galas, D. J. (2010) Export of microRNAs and microRNA-protective protein by mammalian cells. *Nucleic Acids Res.*, 38, 7248-7259. 13. Turchinovich, A., Weiz, L., Langheinz, A. and Burwinkel, B. (2011) Characterization of extracellular circulating microRNA. *Nucleic Acids Res.*, 39, 7223-7233. 14. Mitchell, P. S., Parkin, R. K., Kroh, E. M., Fritz, B. R., Wyman, S. K., Pogosova-Agadjanyan, E. L., Peterson, A., Noteboom, J., O'Briant, K. C., Allen, A. et al. (2008) Circulating microRNAs as stable blood-based markers for cancer detection. *Proc. Natl. Acad. Sci. U.S.A.*, 105, 10513-10518. 15. Weber, J., Baxter, D. H., Zhang, S., Huang, D. Y., Huang, K. H., Lee, M. J., Galas, D. J. and Wang, K. (2010) The microRNA spectrum in 12 body fluids. *Clin. Chem.*, 56, 1733-1741. 16. Arroyo, J. D., Chevillet, J. R., Kroh, E. M., Ruf, I. K., Pritchard, C. C., Gibson, D. F., Mitchell, P. S., Bennett, C. F., Pogosova-Agadjanyan, E. L., Stirewalt, D. L. et al. (2011) Argonaute2 complexes carry a population of circulating microRNAs independent of vesicles in human plasma. *Proc. Natl. Acad. Sci. U.S.A.*, 108, 5003-5008. 17. Toiyama, Y., Okugawa, Y. and Goel, A. (2014) DNA methylation and microrna biomarkers for noninvasive detection of gastric and colorectal cancer. *Biochem. Biophys. Res. Commun.*, 455, 43-57. 18. Xu, L., Li, M., Wang, M., Yan, D., Feng, G. and An, G. (2014) The expression of microRNA-375 in plasma and tissue is matched in human colorectal cancer. *BMC Cancer*, 14, 714. 19. Schrauder, M. G., Strick, R., Schulz-Wendtland, R., Strissel, P. L., Kahmann, L., Loehberg, C. R., Lux, M. P., Jud, S. M., Hartmann, A., Hein, A. et al. (2012) Circulating micro-RNAs as potential blood-based markers for early stage breast cancer detection. *PLoS One*, 7, e29770. 20. Heneghan, H. M., Miller, N., Lowery, A. J., Sweeney, K. J., Newell, J. and Kerin, M. J. (2010) Circulating microRNAs as novel minimally invasive biomarkers for breast cancer. *Ann. Surg.*, 251, 499-505. 21. Zhou, W., Fong, M. Y., Min, Y., Somlo, G., Liu, L., Palomares, M. R., Yu, Y., Chow, A., O'Connor, S. T, F., Chin, A. R. et al. (2014) Cancer-Secreted miR-105 destroys vascular endothelial barriers to promote metastasis. *Cancer Cell*, 25, 501-515. 22. Kumar, P., Derso, Z., MacKenzie, C., Oestreicher, J., Agoulnik, S., Byrne, M., Bernier, F., Yanagimachi, M., Aoshima, K. and Oda, Y. (2013) Circulating miRNA biomarkers for Alzheimer's disease. *PLoS One*, 8, e69807. 23. Duong Van Huyen, J.-P., Tible, M., Gay, a., Guillemain, R., Aubert, O., Varnous, S., Iserin, F., Rouvier, P., Francois, a., Vernerey, D. et al. (2014) MicroRNAs as non-invasive biomarkers of heart transplant rejection. *Eur. Heart J.*, 35, 3194-3202. 24. Wang, K, Zhang, S., Marzolf, B., Troisch, P., Brightman, A., Hu, Z., Hood, L. E. and Galas, D. J. (2009) Circulating microRNAs, potential biomarkers for drug-induced liver injury. *Proc. Natl. Acad. Sci. U.S.A.*, 106, 4402-4407. 25. Vickers, K, C., Palmisano, B, T., Shoucri, B. M., Shamburek, R. D. and Remaley, A. T. (2011) MicroRNAs are transported in plasma and delivered to recipient cells by high-density lipoproteins. *Nat. Cell Biol.*, 13, 423-433. 26. Mestdagh, P., Hartmann, N., Baeriswyl, L., Andreasen, D., Bernard, N., Chen, C., Cheo, D., D'Andrade, P., DeMayo, M., Dennis, L. et al. (2014) Evaluation of quantitative miRNA expression platforms in the microRNA quality control (miRQC) study. *Nat. Methods*, 11, 809-815. 27. Vigneault, F., Sismour, a. M. and Church, G. M. (2008) Efficient microRNA capture and bar-coding via enzymatic oligonucleotide adenylation. *Nat. Methods*, 5, 777-779. 28. Alon, S., Vigneault, F., Eminaga, S., Christodoulou, D. C., Seidman, J. G., Church, G. M. and Eisenberg, E. (2011) Barcoding bias in high-throughput multiplex sequencing of miRNA. *Genome Res.*, 21, 1506-1511. 29. Eminaga, S., Christodoulou, D. C, Vigneault, F., Church, G. M. and Seidman, J. G. (2013) Quantification of microRNA expression with next-generation sequencing. *Curr. Protoc. Mol. Biol.*, doi:10.1002/0471142727.mb0417s103. 30. Hafner, M., Renwick, N., Brown, M., Mihailovic, A., Holoch, D., Lin, C., Pena, J. T. G., Nusbaum, J. D., Morozov, P., Ludwig, J. et al. (2011) RNA-ligase-dependent biases in miRNA representation in deep-sequenced small RNA cDNA libraries. *RNA*, 17, 1697-1712. 31. Zhang, Z., Lee, J. E., Riemondy, K., Anderson, E. M. and Yi, R. (2013) High-efficiency RNA cloning enables accurate quantification of miRNA expression by deep sequencing. *Genome Biol.*, 14, R109. 32. Pritchard, C. C., Kroh, E., Wood, B., Arroyo, J. D., Dougherty, K. J., Miyaji, M. M., Tait, J. F. and Tewari, M. (2012) Blood cell origin of circulating microRNAs: a cautionary note for cancer biomarker studies. *Cancer Prev. Res.*, 5, 492-497. 33. Yamada, A., Cox, M. a., Gaffney, K. a., Moreland, A., Boland, C. R. and Goel, A. (2014) Technical factors involved in the measurement of circulating microRNA biomarkers for the detection of colorectal neoplasia. *PLoS One*, 9, e112481. 34. Williams, Z., Ben-Dov, I. Z., Elias, R., Mihailovic, A., Brown, M., Rosenwaks, Z. and Tuschl, T. (2013) Comprehensive profiling of circulating microRNA via small RNA sequencing of cDNA libraries reveals biomarker potential and limitations. *Proc. Natl. Acad. Sci. U.S.A.*, 110, 4255-4260. 35. Leidner, R. S., Li, L. and Thompson, C. L. (2013) Dampening enthusiasm for circulating microRNA in breast cancer. *PLoS One*, 8, 1-11. 36. Witwer, K. W. (2014) Circulating microRNA biomarker studies: pitfalls and potential solutions. *Clin. Chem.*, 61, 56-63. 37. Martin, M. (2011) Cutadapt removes adapter sequences from high-throughput sequencing reads. *EMBnet.journal*, 17, 10-12. 38. Kozomara, A. and Griffiths-Jones, S. (2014) MiRBase: annotating high confidence microRNAs using deep sequencing data. *Nucleic Acids Res.*, 42, 68-73. 39. Langmead, B. and Salzberg, S. L. (2012) Fast gapped-read alignment with Bowtie 2. *Nat. Methods*, 9, 357-359. 40. Quinlan, A. R. and Hall, I. M. (2010) BEDTools: a flexible suite of utilities for comparing genomic features. *Bioinformatics*, 26, 841-842. 41. Anders, S. and Huber, W. (2010) Differential expression analysis for sequence count data. *Genome Biol.*, 11, R106. 42. Wyman, S. K., Knouf, E. C., Parkin, R. K., Fritz, B. R., Lin, D. W., Dennis, L, M., Krouse, M. a., Webster, P. J. and Tewari, M. (2011) Post-transcriptional generation of miRNA variants by multiple nucleotidyl transferases contributes to miRNA transcriptome complexity. *Genome Res.*, 21, 1450-1461. 43. Newman, M. A, Mani, V. and Hammond, S. M. (2011) Deep sequencing of microRNA precursors reveals extensive 3' end modification. RNA, 17, 1795-1803. 44. Landegren, U., Kaiser, R., Sanders, J. and Hood, L. (1988) A ligase-mediated gene detection technique. *Science*, 241, 1077-1080.

2. Working Example #2: Determination of Relative Counts of Unwanted miRNA in Blocked and Unblocked Samples Initial attempts to use blocking nucleic acids that ligate to the 3' end of the unwanted miRNA were unsuccessful, resulting in miRNA libraries with low efficiency of adaptor binding. Eventually it was hypothesized that residual ATP used in the T4 DNA ligation reaction was inhibiting the effectiveness of T4 RNA ligase 2, truncated. The following protocol was developed to solve the problem.

3' Blocking Protocol

Initially, 1 µl 0.5 µM miRNA blocking oligonucleotide was incubated for five minutes at each of the following temperatures: 95° C., 65° C., 55° C., 45° C., and 35° C. to ensure the proper formation of the hairpin structure. The incubated blocking oligonucleotide was combined with 4 µl of isolated RNA containing microRNAs along with 1 µl T4 DNA Ligase (NEB), 1 µl 10×T4 DNA Ligase Buffer (NEB), 1 µl Murine RNAse inhibitor (NEB), and 2 µl of water and incubated for one hour at 30° C. and 15 minutes at 65° C. to anneal and block the unwanted miRNA from further reactions. After incubation, the reaction products were isolated using a column capable of binding microRNAs and eluted in 20 µl of water in order to remove the ATP present from the 10×T4 DNA Ligase buffer, which is inhibitory to T4 RNA Ligase 2, truncated. After the column clean-up, 10 µl of the column eluate, 1 µl of 10 µM 3' adaptor, 1 µl T4 RNA Ligase 2, truncated (NEB), 1 µl Murine RNAse inhibitor (NEB), 2.5 µl 50% PEG 8000 (NEB), 2 µl 10×T4 RNA Ligase Buffer (RNA), and 0.5 µl of water were combined to a final volume of 19 µl and incubated at 25° C. for one hour. One µl of 10 µM reverse transcription primer was annealed to the 3' ligation product for five minutes at 75° C., 30 minutes at 37° C., and 15 minutes at 25° C. prior to the addition of the 5' adaptor in order to reduce formation of adaptor-dimer products. One µl of 20 µM pooled 5' adaptor was incubated for two minutes at 70° C. and then combined with the previous reaction as well as 1 µl T4 RNA Ligase 1 (NEB), 1 µl Murine RNAse Inhibitor (NEB) 1 µl 10 mM ATP, and 1 µl 10×T4 RNA Ligase Buffer, and incubated for one hour at 25° C. Ligated reaction products were reverse transcribed by combining 11 µl of the ligation reaction with 1 µl SuperScript II (Invitrogen), 4 µl 5× First Strand Reaction Buffer (Invitrogen), 2 µl of 100 mM DTT (Invitrogen), 1 µl Murine RNAse Inhibitor (NEB), and 1 µl 10 mM dNTPs each and incubated for 50 minutes at 42° C. and 15 minutes at 70° C. The resulting cDNA containing reaction was amplified via PCR by adding 25 µl of 2× Phusion High-Fidelity PCR Master Mix (NEB) along 2.5 µl each of the 20 µM forward and reverse primers. The thermal cycling conditions were 94° C. for 30 sec, followed by 15 cycles of 94° C. for 10 sec, and 72° C. for 45 sec, and a final extension at 65° C. for five minutes. Libraries were cleaned and concentrated using a MinElute PCR Purification Kit (Qiagen), following the manufacturer's instructions, and eluted into a final volume of 20 µl. Libraries were separated on a TBE-Urea 10 percent acrylamide gel (Bio-Rad) with warm buffer for 50 minutes. The band corresponding to miRNAs (~135-145 base pairs) was excised, eluted from the gel, precipitated, and resuspended in 10 µl of EB Buffer (Qiagen). Small RNA library concentration was quantified by the Library Quantification Kit—Illumina/ABI Prism (KAPA Biosystems) and sequenced on a HiSeq2000 or a MiSeq according to standard Illumina protocols.

Study of Blocking Efficiency Using Singular and Pooled 5' and 3' Blockers

Using the same methods described above, miRNA libraries of human heart miRNA were constructed using the blocking protocol and without the blocking protocol. The improved 3' blocking protocol from the previous section was used to test the efficacy of a 3' blocker to miR-16.

Figure 14:
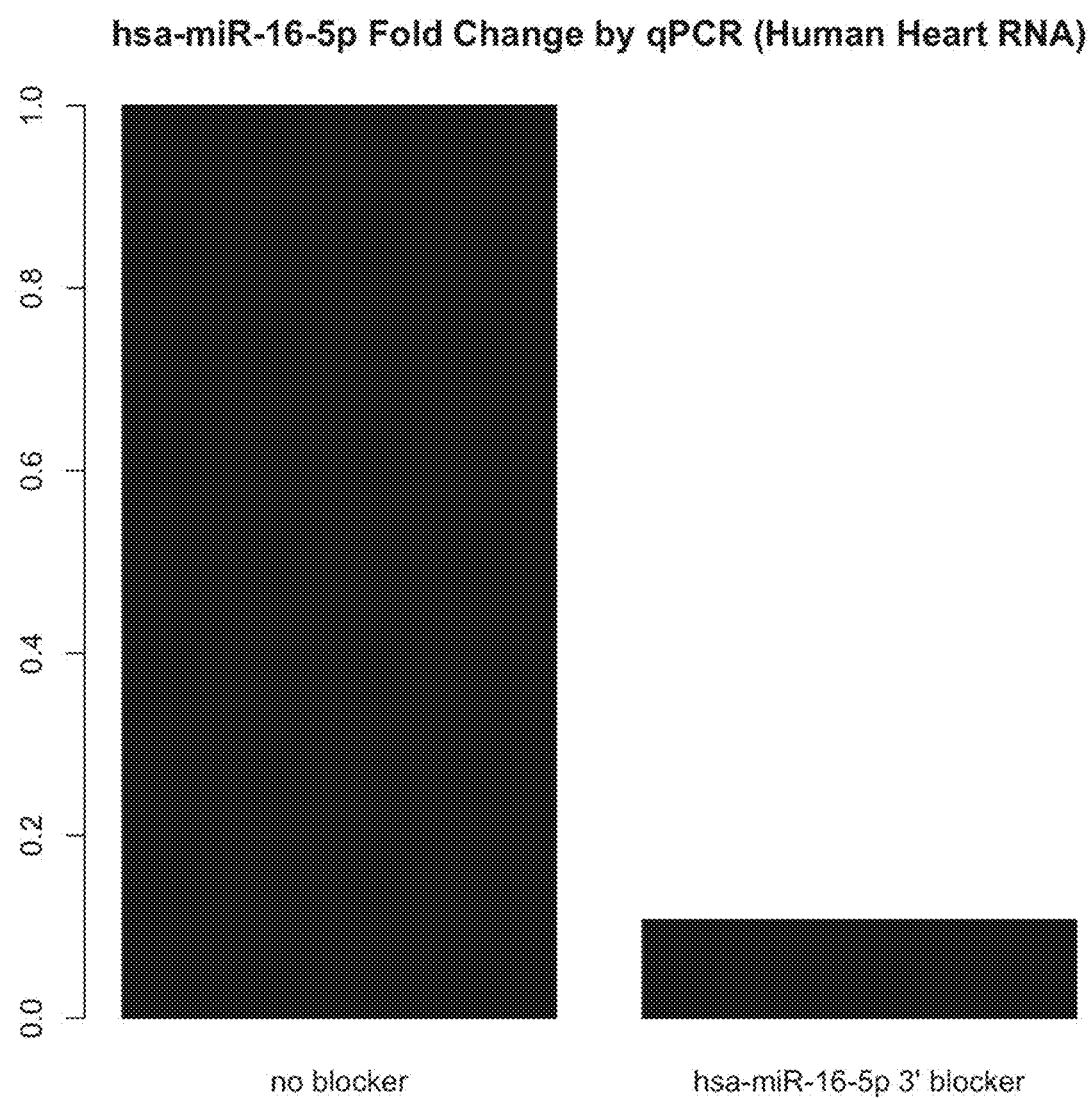
FIG. 14. Side by side comparison of abundance of hsa-miR-16-5p in unblocked library and blocked library using hsa-miR-15-5p 3' blocker.
Figure 15:
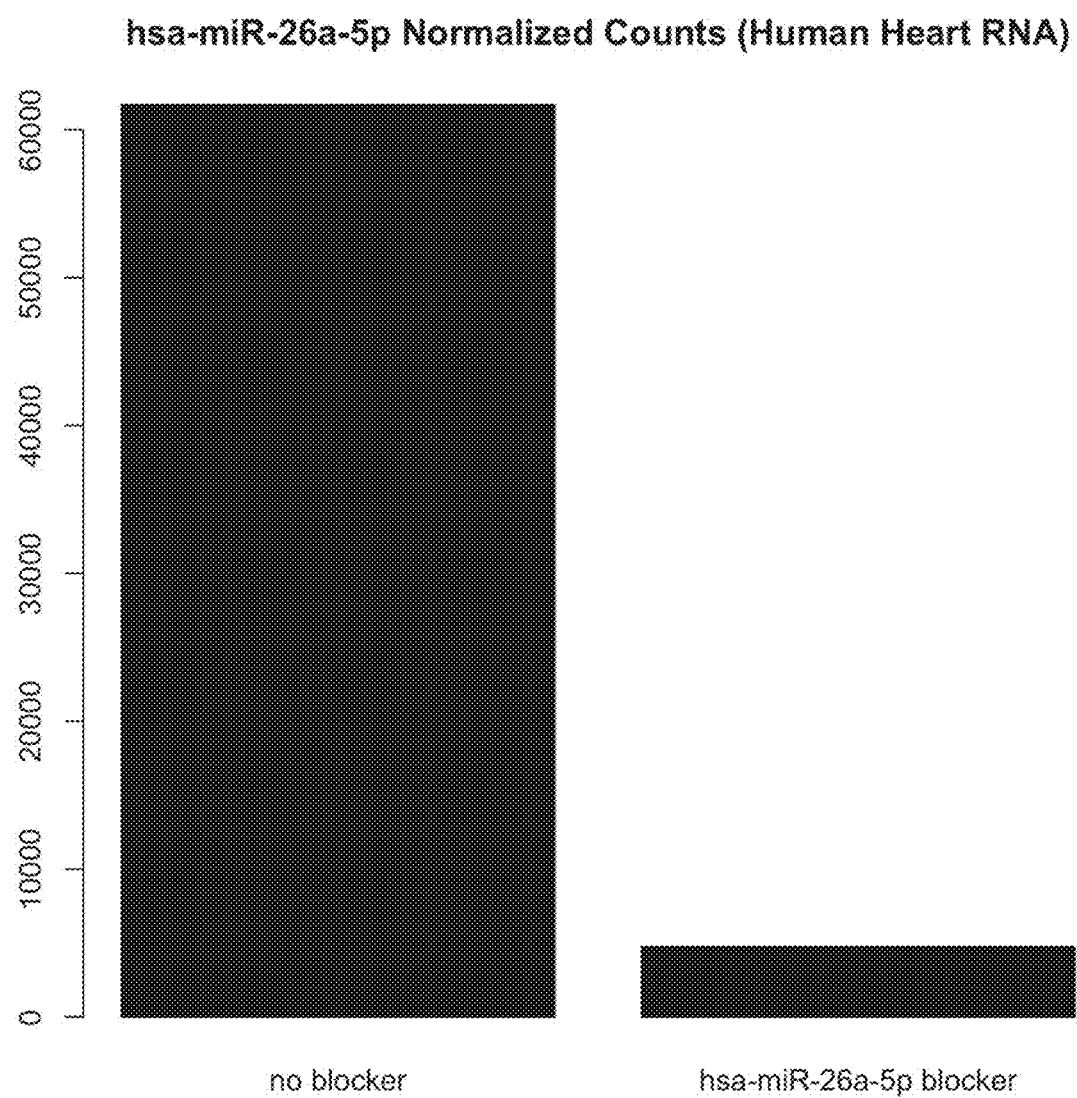
FIG. 15. Side by side comparison of abundance of hsa-miR-26a-5p in unblocked library and blocked library using hsa-miR-26a-5p 5' blocker.
Figure 16:
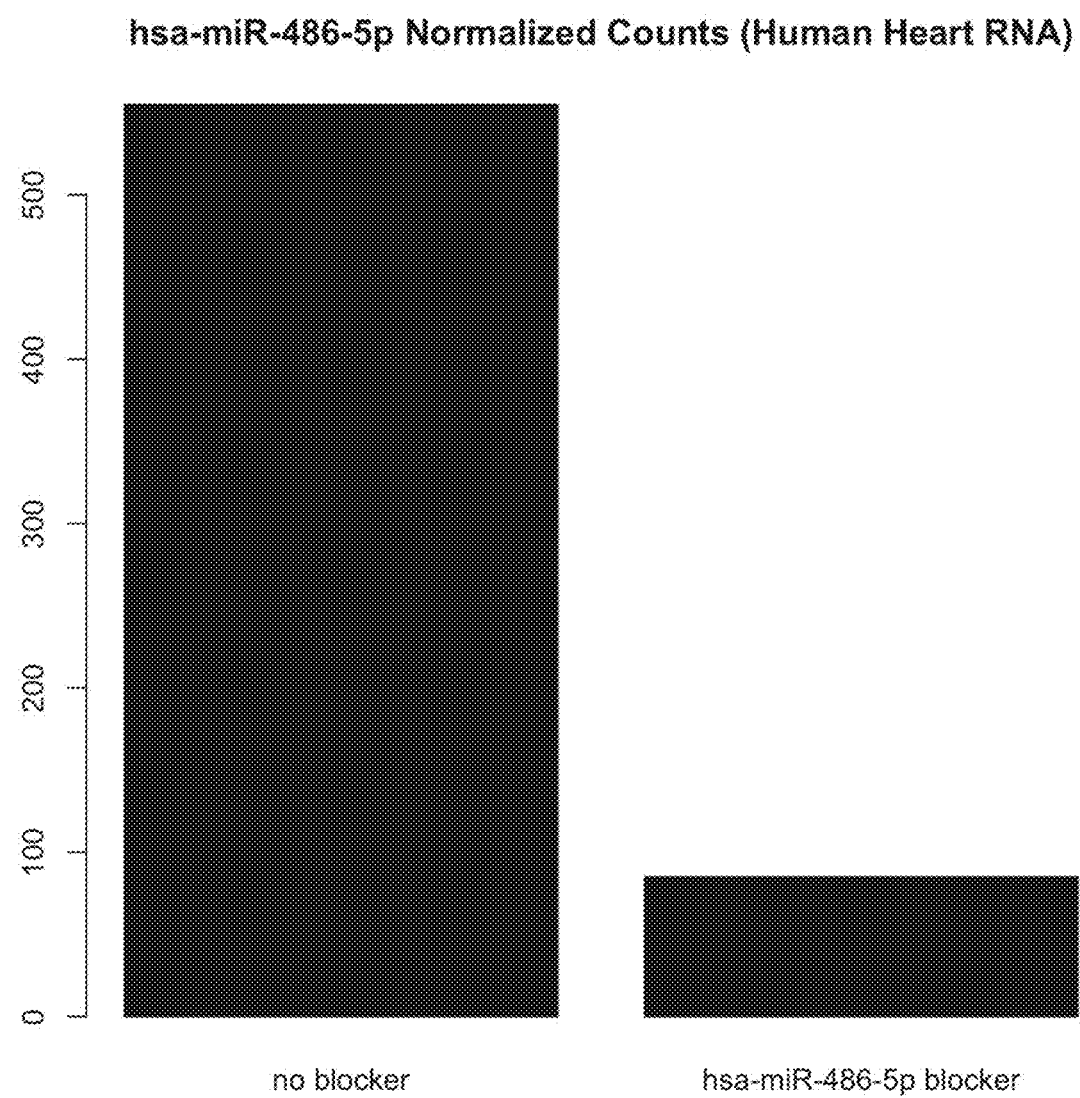
FIG. 16. Side by side comparison of abundance of hsa-miR-486-5p in unblocked library and blocked library using hsa-miR-486-5p 5' blocker.
Figure 17:
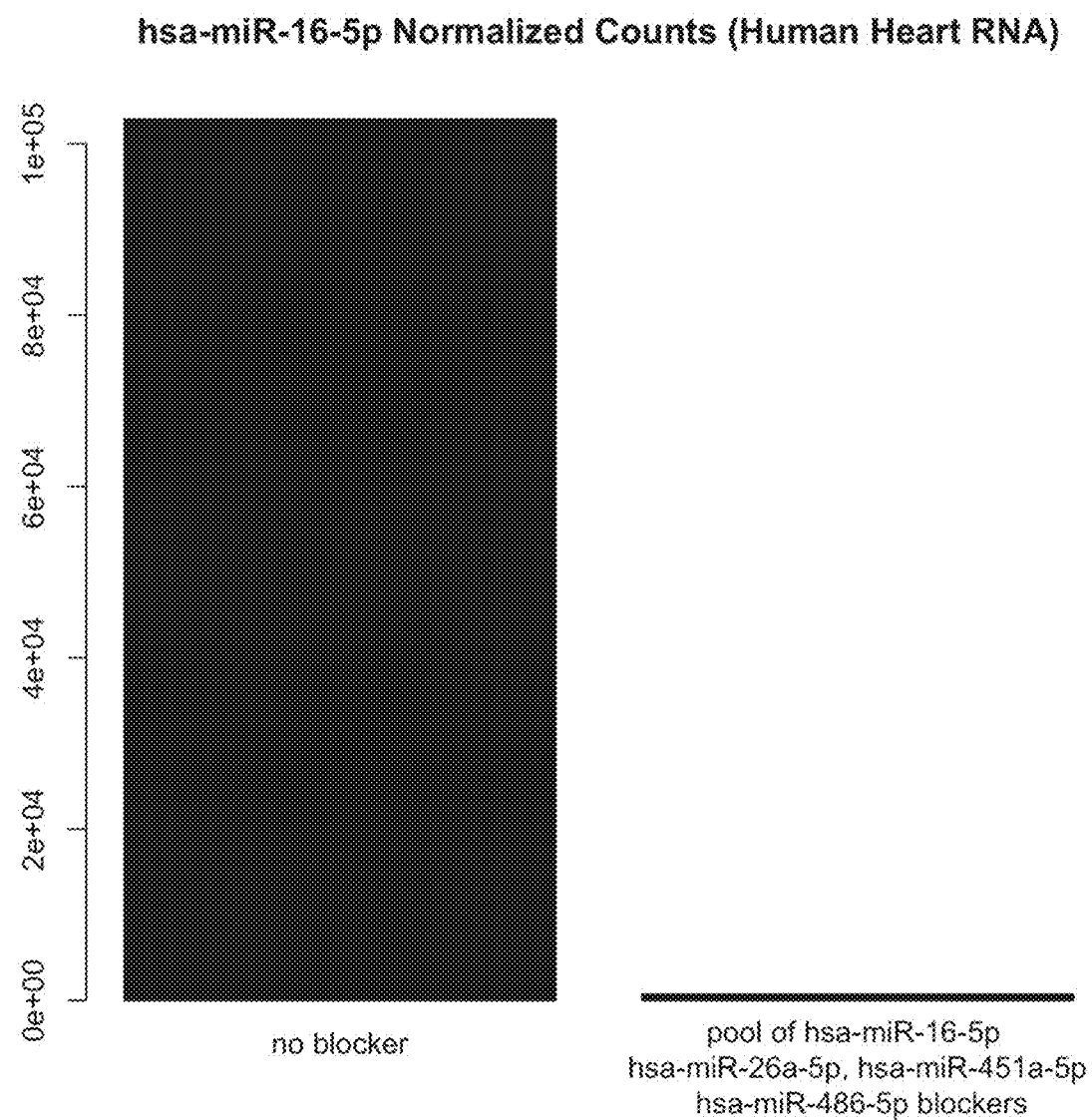
FIG. 17. Side by side comparison of abundance of hsa-miR-16-5p in unblocked library and blocked library using pool of blockers.
Figure 18:
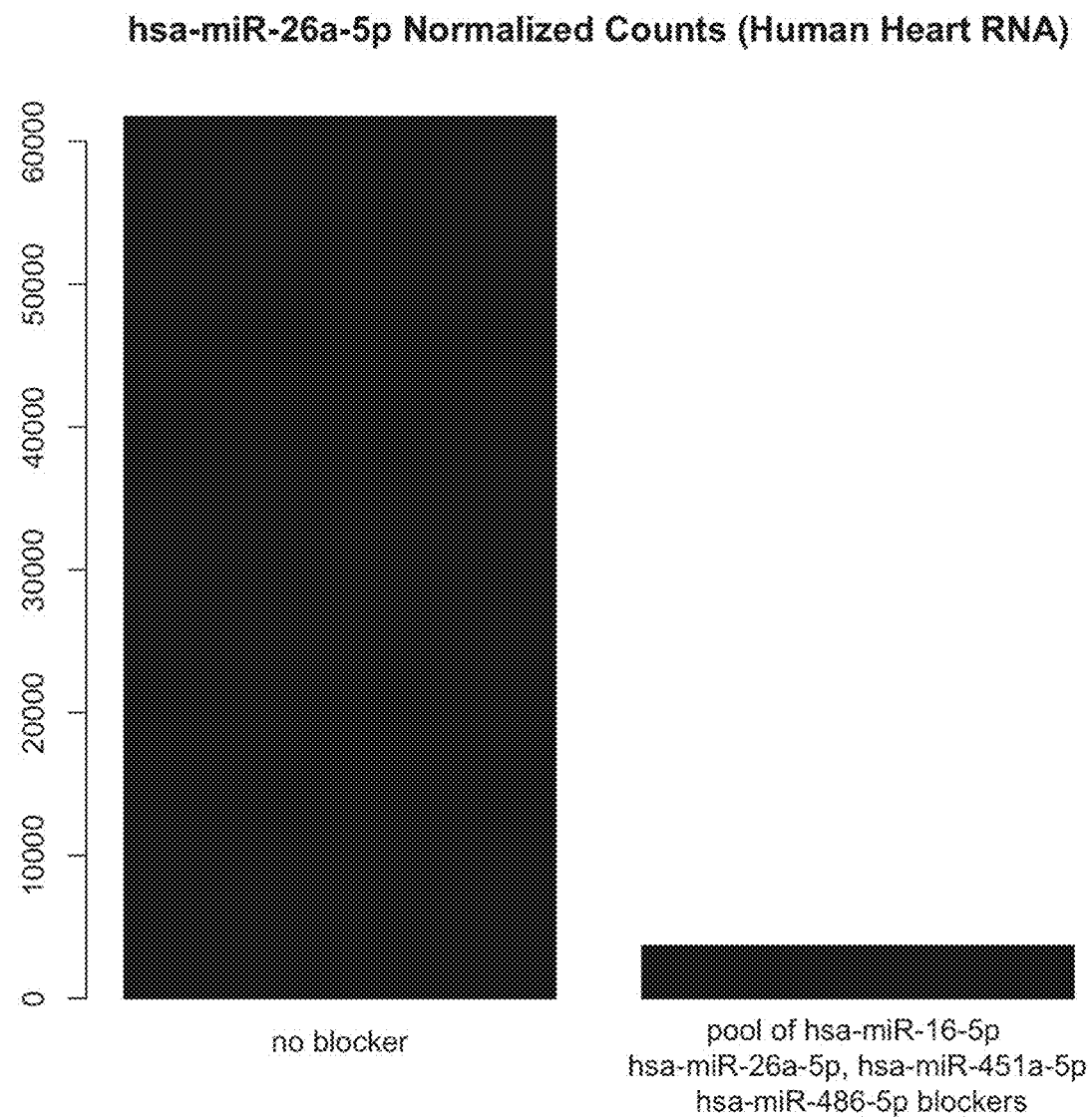
FIG. 18. Side by side comparison of abundance of hsa-miR-26a-5p in unblocked library and blocked library using pool of blockers.
Figure 19:
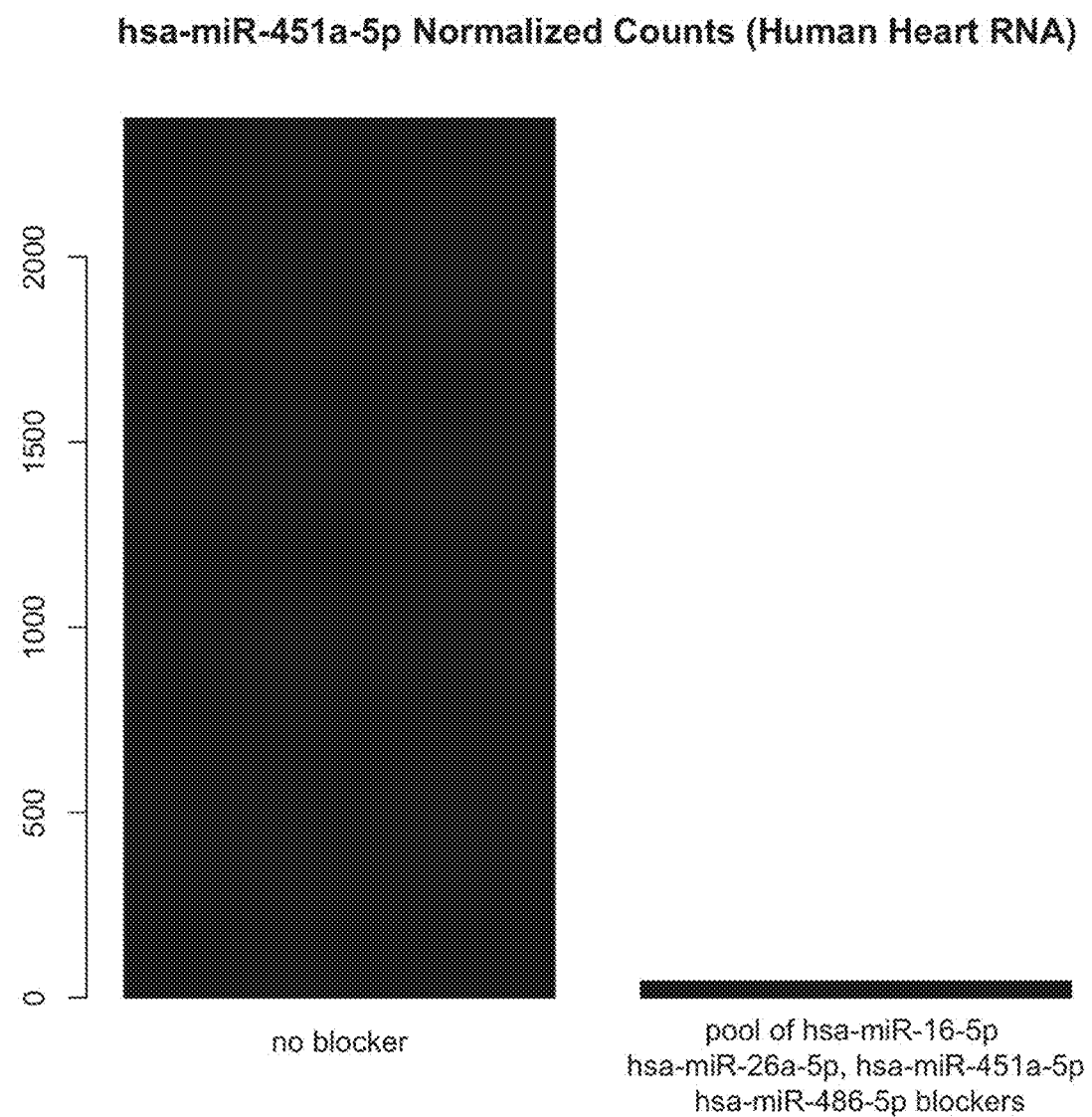
FIG. 19. Side by side comparison of abundance of hsa-miR-451a-5p in unblocked library and blocked library using pool of blockers.
Figure 20:
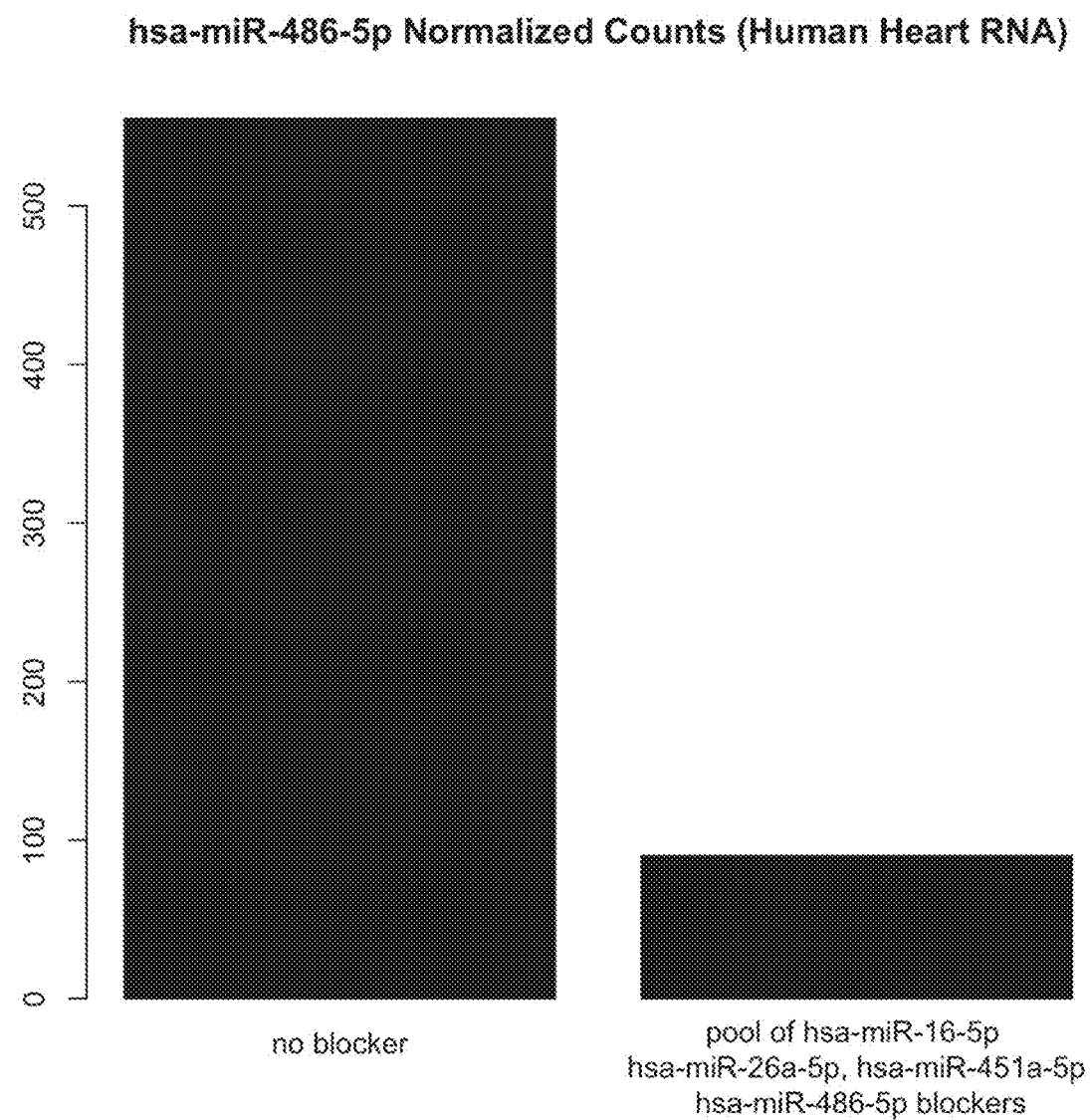
FIG. 20. Side by side comparison of abundance of hsa-miR-486-5p in unblocked library and blocked library using pool of blockers.

Comparisons were made to libraries without blocker and libraries made using an hsa-miR-16-5p 3' blocker (SEQ ID NO: 13 with a 3' C3 phosphoramidite spacer), an hsa-miR-26a-5p 5' blocker (SEQ ID NO: 2 with a 5' C3 phosphoramidite spacer), and an hsa-miR-486-5p 5' blocker (SEQ ID NO: 1 with a 5' C3 phosphoramidite spacer). As shown in FIG. 14-16 respectively, in each case the normalized counts of the blocked miRNA was reduced significantly compared to the control.

The blocking protocol was then tested using a mixed pool of blockers. A pool of blockers was prepared containing an hsa-miR-16-5p 3' blocker (SEQ ID NO: 13 with a 3' C3 phosphoramidite spacer), an hsa-miR-26a-5p 5' blocker (SEQ ID NO: 2 with a 5' C3 phosphoramidite spacer), hsa-miR-451-5p 5' blocker (SEQ ID NO: 3 with a 5' C3 phosphoramidite spacer) and an hsa-miR-486-5p 5' blocker (SEQ ID NO: 1 with a 5' C3 phosphoramidite spacer). miRNA libraries of human heart miRNA were constructed using the blocking protocol with the pool and without the blocking protocol. The abundances of each of hsa-miR-16-5p, hsa-miR-26a-5p, and hsa-miR-486-5p were measured. As can be seen in FIG. 17-20, the pooled blockers significantly reduced the abundance of each of the unwanted miRNAs in the resultant library.

G. Supported Embodiments

This disclosure specifically but non-exclusively supports claims to the following embodiments: Emb 1. A blocking nucleic acid for use in reducing the abundance of an unwanted micro-RNA (miRNA) in an miRNA library, the blocking nucleic acid comprising: (a) a Crick strand having a 3' end and a 5' end; (b) a single stranded complementary region at one of the 5' end of the Crick strand or the 3' end of the Crick strand, that anneals with a binding region at a first end of the unwanted miRNA under stringent conditions, wherein said first end is the 5' end or the 3' end of the unwanted miRNA; (c) a double-stranded region on the Crick strand adjacent to the complementary region, the double-stranded region comprising a Watson strand that is annealed to the Crick strand, the Watson strand having a 5' end and a 3' end; (d) a first blocking moiety linked to the 3' end of the Crick strand, wherein the first blocking moiety cannot serve as a substrate for ligases; (e) a second blocking moiety linked to the 5' end of the Crick strand, wherein the second blocking moiety cannot serve as a substrate for ligases; (f) a third blocking moiety linked to the 3' end of the Watson strand if the complementary region is at the 3' end of the Crick strand, or linked to the 5' end of the Watson strand if the complementary region is at the 5' end of the Crick strand, wherein the third blocking moiety cannot serve as a substrate for ligases; and (g) a ligative terminal end on the Watson strand, the ligative terminal end located at the 3' end of the Watson strand if the complementary region is at the 5' end of the Crick strand, or at the 5' end of the Watson strand if the complementary region is at the 3' end of the Crick strand. Emb 2. A blocking nucleic acid for use in reducing the abundance of an unwanted micro-RNA (miRNA) in an miRNA library, the blocking nucleic acid comprising: (a) a 5' end of the blocking nucleic acid and a 3' end of the blocking nucleic acid; (b) a single-stranded complementary region at one of the 5' end of the blocking nucleic acid or the 3' end of the blocking nucleic acid, that anneals with a binding region at a first end of the unwanted miRNA under stringent conditions, wherein said first end is either the 5' end or the 3' end of the unwanted miRNA, and wherein the complementary region has a terminal end; (c) a hairpin loop forming region adjacent to the complimentary region, the hairpin loop forming region having a ligative terminal end; and (d) a first blocking moiety linked to the terminal end of the complementary region, in which said first blocking moiety cannot serve as a substrate for ligases. Emb 3. The blocking nucleic acid of any one of the above, wherein the complementary region anneals with the binding region under highly stringent conditions. Emb 4. The blocking nucleic acid of any one of the above, wherein the complementary region anneals with the binding region under maximally stringent conditions Emb 5. The blocking nucleic acid of any one of the above, wherein the blocking nucleic acid comprises a linker group between the first blocking moiety and the complementary region. Emb 6. The blocking nucleic acid of any one of the above, wherein the blocking nucleic acid comprises a linker group between the first blocking moiety and the complementary region, wherein the linker group is selected from the group consisting of: Spacer 9 (triethylene glycol) and Spacer 18 (hexa-ethyleneglycol). Emb 7. The blocking nucleic acid of any one of the above, wherein the complementary region is 5-50 nucleotides in length. Emb 8. The blocking nucleic acid of any one of the above, wherein the complementary region is 8-20 nucleotides in length. Emb 9. The blocking nucleic acid of any one of the above, wherein the complementary region is 10-15 nucleotides in length. Emb 10. The blocking nucleic acid of any one of the above, wherein the complementary region comprises a sequence having at least 90% identity with positions 1-12 of one of SEQ ID NO: 1-4. Emb 11. The blocking nucleic acid of any one of the above, wherein the complementary region comprises a sequence having greater than 95% identity with positions 1-12 of one of SEQ ID NO: 1-4. Emb 12. The blocking nucleic acid of any one of the above, wherein the complementary region comprises a sequence having at least 90% identity with positions 1-12 of SEQ ID NO: 4. Emb 13. The blocking nucleic acid of any one of the above, wherein the complementary region comprises a sequence having greater than 95% identity with positions 1-12 of SEQ ID NO: 4. Emb 14. The blocking nucleic acid of any one of the above, wherein the first blocking moiety is a modified nucleotide that either lacks an available 5' phosphate group, lacks an available 3' hydroxyl group, or both. Emb 15. The blocking nucleic acid of any one of the above, wherein the first blocking moiety is selected from the group consisting of: an inverted deoxynucleotide, dideoxynucleotide, an inverted dideoxynucleotide, C3 spacer (phosphoramidite), Spacer 9 (triethylene glycol), propyl group, propanol group, and Spacer 18 (hexa-ethyleneglycol). Emb 16. The blocking nucleic acid of Emb 2, wherein said hairpin loop forming region group comprises a sequence having at least 90% identity with SEQ ID NO: 5. Emb 17. The blocking nucleic acid of any one of Emb 2 or 16, wherein said hairpin loop forming region group comprises a sequence having greater than 95% identity with SEQ ID NO: 5. Emb 18. The blocking nucleic acid of any one of the above, wherein the complementary region anneals under stringent conditions with at least 5 consecutive bases of at least one of SEQ ID NOS: 6-11. Emb 19. The blocking nucleic acid of any one of the above, wherein the complementary region anneals under stringent conditions with at least 8 consecutive bases of at least one of SEQ ID NOS: 6-11. Emb 20. The blocking nucleic acid of any one of the above, wherein the complementary region anneals under stringent conditions with at least 10 consecutive bases of at least one of SEQ ID NOS: 6-11. Emb 21. The blocking nucleic acid of any one of the above, wherein the complementary region anneals under stringent conditions with positions 1-8 of at least one of SEQ ID NO:6 and SEQ ID NO: 10. Emb 22. The blocking nucleic acid of any one of the above, wherein the complementary region anneals under stringent conditions with positions 1-9 of at least one of SEQ ID NOS: 6-11. Emb 23. The blocking nucleic acid of any one of the above, wherein the complementary region anneals under highly stringent conditions with at least 5 consecutive bases of at least one of SEQ ID NOS: 6-11. Emb 24. The blocking nucleic acid of any one of the above, wherein the complementary region anneals under highly stringent conditions with at least 8 consecutive bases of at least one of SEQ ID NOS: 6-11. Emb 25. The blocking nucleic acid of any one of the above, wherein the complementary region anneals under highly stringent conditions with at least 10 consecutive bases of at least one of SEQ ID NOS: 6-11. Emb 26. The blocking nucleic acid of any one of the above, wherein the complementary region anneals under highly stringent conditions with positions 1-8 of at least one of SEQ ID NO:6 and SEQ ID NO: 10. Emb 27. The blocking nucleic acid of any one of the above, wherein the complementary region anneals under highly stringent conditions with positions 1-9 of at least one of SEQ ID NOS: 6-11. Emb 28. The blocking nucleic acid of any one of the above, wherein the complementary region anneals under maximally stringent conditions with at least 5 consecutive bases of at least one of SEQ ID NOS: 6-11. Emb 29. The blocking nucleic acid of any one of the above, wherein the complementary region anneals under maximally stringent conditions with at least 8 consecutive bases of at least one of SEQ ID NOS: 6-11. Emb 30. The blocking nucleic acid of any one of the above, wherein the complementary region anneals under maximally stringent conditions with at least 10 consecutive bases of at least one of SEQ ID NOS: 6-11. Emb 31. The blocking nucleic acid of any one of the above, wherein the complementary region anneals under maximally stringent conditions with positions 1-8 of at least one of SEQ ID NO:6 and SEQ ID NO: 10. Emb 32. The blocking nucleic acid of any one of the above, wherein the complementary region anneals under maximally stringent conditions with positions 1-9 of at least one of SEQ ID NOS: 6-11. Emb 33. The blocking nucleic acid of any one of the above, wherein the blocking nucleic acid is composed of a nucleic acid selected from the group consisting of: DNA, RNA, locked nucleic acid, and bridged nucleic acid. Emb 34. The blocking nucleic acid of any one of Emb 2, 16 and 17 wherein the blocking nucleic acid is a DNA molecule comprising a sequence having at least 90% identity with at least one of: SEQ ID NOS: 1-4. Emb 35. The blocking nucleic acid of any one of Emb 2, 16, 17, and 34 wherein the blocking nucleic acid is a DNA molecule comprising a sequence having greater than 95% identity with at least one of: SEQ ID NOS: 1-4. Emb 36. The blocking nucleic acid of any one of Emb 2, 16, 17, 34, and 35 wherein the blocking nucleic acid is a DNA molecule comprising a sequence having at least 90% identity with SEQ ID NO: 4. Emb 37. The blocking nucleic acid of any one of Emb 2, 16, 17, and 34-36, wherein the blocking nucleic acid is a DNA molecule comprising a sequence having greater than 95% identity with SEQ ID NO: 4. Emb 38. The blocking nucleic acid of any one of Emb 2, 16 and 17, wherein the blocking nucleic acid is a DNA molecule comprising a sequence having at least 90% identity with SEQ ID NO: 13. Emb 39. The blocking nucleic acid of any one of Emb 2, 16, 17, and 38 wherein the blocking nucleic acid is a DNA molecule comprising a sequence having greater than 95% identity with SEQ ID NO: 13. Emb 40. The blocking nucleic acid of any one of the above, wherein the ligative terminal end is a nucleotide having one of an available 5' phosphate group or an available 3' hydroxyl group. Emb 41. A method of preventing a unwanted microRNA (miRNA) from participating in reverse transcription polymerase chain reactions (RT-PCR), the unwanted miRNA having a 5' end and a 3' end, the method comprising: annealing the complementary region of the blocking nucleic acid of any one Emb 1-Emb 40 to the binding site at the first end of the unwanted miRNA, wherein the first end of the unwanted miRNA is one of the 5' end or the 3' end. Emb 42. The method of Emb 41, wherein annealing is conducted under stringent conditions. Emb 43. The method of any one of Emb 41-42, wherein annealing is conducted under highly stringent conditions. Emb 44. The method of any one of Emb 41-43, wherein annealing is conducted under maximally stringent conditions. Emb 45. The method of any one of Emb 41-44, comprising ligating the blocking nucleic acid to the first end of the unwanted miRNA. Emb 46. The method of any one of Emb 41-45, wherein the first end of the unwanted miRNA is the 5' end and the complementary region is at the 5' end of the blocking nucleic acid. Emb 47. The method of any one of Emb 41-46, wherein the first end of the unwanted miRNA is the 3' end and the complementary region is at the 3' end of the blocking nucleic acid. Emb 48. The method of any one of Emb 41-47, comprising ligating the blocking nucleic acid to the first end of the unwanted miRNA, wherein the ligating step is performed using a DNA/RNA ligase. Emb 49. The method of any one of Emb 41-48, comprising ligating the blocking nucleic acid to the first end of the unwanted miRNA, wherein the ligating step is performed using a T4 DNA ligase. Emb 50. The method of any one of Emb 41-49, wherein the unwanted miRNA is selected from the group consisting of: mir-16, mir-15a, mir-15b, mir-195, mir-424, mir-497, mir-486, mir-451, and mir-26. Emb 51. A blocked micro RNA (miRNA) complex that is the product of the method of any one of Emb 41-50. Emb 52. A method of reducing the abundance of a unwanted micro-RNA (miRNA) in an miRNA library, the unwanted miRNA having a 5' end and a 3' end, the method comprising: (a) purifying RNA from a sample comprising a plurality of miRNAs; (b) introducing an adenylated nucleic acid adapter and a first DNA/RNA ligase under conditions to allow the adenylated nucleic acid adapter to ligate to the 3' ends of the plurality of miRNAs; (c) introducing the blocking nucleic acid of any one Emb 1-Emb 40 under conditions to allow the complementary region of the blocking nucleic acid to anneal to the binding region of the unwanted miRNA, to produce a blocked sample; (d) introducing an RNA adapter and an RNA ligase under conditions to allow the RNA adapter to ligate the 5' end of the plurality of miRNAs; (e) introducing a reverse transcriptase to the blocked sample under conditions to allow reverse transcription of the plurality of miRNAs, to produce a cDNA sample; and (f) performing the polymerase chain reaction (PCR) on the cDNA sample to produce the miRNA library with reduced abundance of unwanted miRNA. Emb 53. The method of Emb 52, comprising introducing a second DNA/RNA ligase under conditions to allow the blocking nucleic acid to ligate to one of the 5' end and the 3' end of the unwanted miRNA. Emb 54. The method of Emb 53, wherein the second DNA/RNA ligase is T4 DNA ligase. Emb 55. The method of any one of Emb 52-54, comprising incubating the blocking nucleic acid with the unwanted miRNA under stringent conditions to allow the complementary region of the blocking nucleic acid to anneal to the binding region of the unwanted miRNA. Emb 56. The method of any one of Emb 52-55, comprising incubating the blocking nucleic acid with the unwanted miRNA under highly stringent conditions to allow the complementary region of the blocking nucleic acid to anneal to the binding region of the unwanted miRNA. Emb 57. The method of any one of Emb 52-56, comprising incubating the blocking nucleic acid with the unwanted miRNA under maximally stringent conditions to allow the complementary region of the blocking nucleic acid to anneal to the binding region of the unwanted miRNA. Emb 58. The method of any one of Emb 52-57, wherein said adenylated nucleic acid adapter comprises a reverse transcriptase primer binding site. Emb 59. The method of any one of Emb 52-58, wherein the adenylated nucleic acid adapter is an adenylated DNA adapter. Emb 60. The method of any one of Emb 52-59, wherein the adenylated nucleic acid adapter is an adenylated RNA adapter. Emb 61. The method of any one of Emb 52-60, wherein the first DNA/RNA ligase is T4 ligase 2, truncated. Emb 62. The method of any one of Emb 52-61, wherein the RNA adapter is 5-30 base pairs in length. Emb 63. The method of any one of Emb 52-62, wherein the RNA adapter is 18-22 base pairs in length. Emb 64. The method of any one of Emb 52-63, wherein the RNA ligase is T4 RNA ligase 1. Emb 65. The method of any one of Emb 52-64, wherein step (c) is performed before at least one of steps (b) and (d). Emb 66. The method of any one of Emb 52-65, wherein the binding region of the unwanted miRNA is the 5' end of the unwanted miRNA. Emb 67. The method of any one of Emb 52-66, wherein the binding region of the unwanted miRNA is the 5' end of the unwanted miRNA, and wherein the steps are performed in the following order: (a), (b), (c), (d), (e), and (f). Emb 68. The method of any one of Emb 52-67, wherein the binding region of the unwanted miRNA is the 3' end of the unwanted miRNA. Emb 69. The method of any one of Emb 52-68, wherein the binding region of the unwanted miRNA is the 3' end of the unwanted miRNA; wherein step (c) is performed before step (b); and wherein the concentration of ATP is reduced between steps (c) and (b). Emb 70. An miRNA library with reduced abundance of an unwanted miRNA that is the product of the method of any one of Emb 52-69. Emb 71. The miRNA library of Emb 70, wherein the abundance of unwanted miRNA has been reduced at least by an amount selected from the group consisting of: 50%, 60%, 70%, 75%, 80%, 85%, 90%, 95%, 97.5%, 98%, 99%, 99.5%, 99%, and 100%. Emb 72. A kit for reducing the frequency of an miRNA in an miRNA library, the kit comprising any the blocking nucleic acids of any one of Emb 1-40. Emb 73. The kit of Emb 72, comprising a container of a DNA/RNA ligase capable of ligating DNA to RNA when annealed. Emb 74. The kit of any one of Emb 72-73, comprising a container of T4 DNA ligase. Emb 75. The kit of any one of The kit of any one of Emb 72-74, comprising a container of an RNA/RNA ligase. Emb 76. The kit of any one of The kit of any one of Emb 72-75, comprising a container of T4 RNA ligase 1. Emb 77. The kit of any one of The kit of any one of Emb 72-75, comprising a container of an RNA/DNA ligase. Emb 78. The kit of any one of Emb The kit of any one of Emb 72-77, comprising a container of T4 RNA ligase 2 truncated. Emb 79. The kit of any one of Emb The kit of any one of Emb 72-78, comprising a container of a reverse transcriptase. Emb 80. The kit of any one of Emb The kit of any one of Emb 72-79, comprising a container of adenylated nucleic acid adapter. Emb 81. The kit of any one of Emb The kit of any one of Emb 72-80, comprising a container of adenylated nucleic acid adapter, wherein said adenylated nucleic acid adapter comprises a reverse transcriptase primer binding site. Emb 82. The kit of any one of Emb The kit of any one of Emb 72-81, comprising a container of adenylated nucleic acid adapter, wherein said adenylated nucleic acid adapter is an adenylated DNA adapter. Emb 83. The kit of any one of Emb The kit of any one of Emb 72-82, comprising a container of adenylated nucleic acid adapter, wherein said adenylated nucleic acid adapter is an adenylated RNA adapter. Emb 84. The kit of any one of Emb The kit of any one of Emb 72-83, comprising a container of an RNA adapter. Emb 85. The kit of any one of Emb The kit of any one of Emb 72-84, comprising a plurality of DNA primers, a nucleotide solution, a PCR buffer, and a thermophilic DNA polymerase. Emb 86. A blocked micro RNA (miRNA) complex, comprising an miRNA annealed to the blocking nucleic acid of any one of Emb 1-40 at the binding region of the miRNA, wherein the first end is one of the 5' end or the 3' end. Emb 87. The blocked miRNA complex of Emb 86, wherein the first end is the 5' end of the miRNA. Emb 88. The blocked miRNA complex of Emb 86, wherein the first end is the 3' end of the miRNA. Emb 89. The blocked miRNA complex of any one of Emb 86-88, wherein the miRNA is selected from the group consisting of: mir-16, mir-15a, mir-15b, mir-195, mir-424, mir-497, mir-486, mir-451, and mir-26. Emb 90. A nucleic acid molecule comprising a sequence having at least 90% identity with one of SEQ ID NOS: 1-4 AND 13. Emb 91. A nucleic acid molecule comprising a sequence having greater than 95% identity with one of SEQ ID NOS: 1-4 AND 13. Emb 92. A nucleic acid molecule comprising a sequence that is one of SEQ ID NOS: 1-4 AND 13. Emb 93. A nucleic acid molecule that anneals under stringent conditions with the nucleic acid molecule of any one of Emb 90-92. Emb 94. A nucleic acid molecule that anneals under highly stringent conditions with the nucleic acid molecule of any one of 90-92. Emb 95. A nucleic acid molecule that anneals under maximally stringent conditions with the nucleic acid molecule of any one of Emb 90-92. Emb 96. A cell comprising any one of the nucleic acid molecules of any one of Emb 90-95. Emb 97. The cell of Emb 96, wherein the cell is a prokaryotic cell. Emb 97. A vector comprising any one of the nucleic acid molecules of any one of Emb 90-95.

H. Conclusions

It is to be understood that any given elements of the disclosed embodiments of the invention may be embodied in a single structure, a single step, a single substance, or the like. Similarly, a given element of the disclosed embodiment may be embodied in multiple structures, steps, substances, or the like.

The foregoing description illustrates and describes the processes, machines, manufactures, compositions of matter, and other teachings of the present disclosure. Additionally, the disclosure shows and describes only certain embodiments of the processes, machines, manufactures, compositions of matter, and other teachings disclosed, but, as mentioned above, it is to be understood that the teachings of the present disclosure are capable of use in various other combinations, modifications, and environments and are capable of changes or modifications within the scope of the teachings as expressed herein, commensurate with the skill and/or knowledge of a person having ordinary skill in the relevant art. The embodiments described hereinabove are further intended to explain certain best modes known of practicing the processes, machines, manufactures, compositions of matter, and other teachings of the present disclosure and to enable others skilled in the art to utilize the teachings of the present disclosure in such, or other, embodiments and with the various modifications required by the particular applications or uses. Accordingly, the processes, machines, manufactures, compositions of matter, and other teachings of the present disclosure are not intended to limit the exact embodiments and examples disclosed herein. Any section headings herein are provided only for consistency with the suggestions of 37 C.F.R. § 1.77 or otherwise to provide organizational queues. These headings shall not limit or characterize the invention(s) set forth herein.

TABLE 2

| SEQUENCE LISTING KEY | |
| --- | --- |
| SEQ ID NO | DESCRIPTION |
| 1 | Example of DNA portion of 5' blocking molecule that targets mir-486 |
| 2 | Example of DNA portion of 5' blocking molecule that targets mir-26 |
| 3 | Example of DNA portion of 5' blocking molecule that targets mir-451 |
| 4 | Example of DNA portion of 5' blocking molecule that targets mir-16 |
| 5 | Consensus sequence between SEQ ID NOS: 1-5 |
| 6 | hsa-miR-16-5p (RNA) |
| 7 | hsa-miR-15a-5p (RNA) |
| 8 | hsa-miR-15b-5p (RNA) |
| 9 | hsa-miR-195-5p (RNA) |
| 10 | hsa-miR-424-5p (RNA) |
| 11 | hsa-miR-497-5p (RNA) |
| 12 | Consensus sequence between SEQ ID NOS: 6-11 |
| 13 | Example of DNA portion of 3' blocking molecule that targets mir-16. |

What is claimed is:

1. A method of reducing the ability of an unwanted micro-RNA (miRNA) that is one of a plurality of miRNAs from participating in reverse transcription polymerase chain reactions (RT-PCR), the unwanted miRNA having a 5' end and a 3' end, the method comprising:
   (a) annealing a complementary region of a blocking nucleic acid to a binding site at a first end of the unwanted miRNA, wherein the first end of the unwanted miRNA is one of the 5' end or the 3' end; and wherein the blocking nucleic acid comprises
   (i) a 5' end of the blocking nucleic acid and a 3' end of the blocking nucleic acid;
   (ii) a single-stranded complementary region at one of the 5' end of the blocking nucleic acid or the 3' end of the blocking nucleic acid, that anneals with the binding site under stringent conditions;
   (iii) a hairpin loop forming region adjacent to the complementary region, the hairpin loop forming region having a ligative terminal end; and (iv) a first blocking moiety linked to the terminal end of the complementary region, in which said first blocking moiety cannot serve as a substrate for ligases;

(b) ligating an adenylated nucleic acid adapter to a 3' end of at least one of the plurality of miRNAs, ligating an RNA adapter to a 5' end of at least one of the plurality of miRNAs, or a combination thereof, wherein step (b) occurs after step (a), and (i) when the blocking nucleic acid is a 3' blocking nucleic acid, the blocking nucleic acid prevents ligation of the adenylated nucleic acid adapter to the 3' end of the unwanted miRNA; and (ii) when the blocking nucleic acid is a 5' blocking nucleic acid, the blocking nucleic acid prevents ligation of the RNA adapter to the 5' end of the unwanted miRNA; and (c) performing RT-PCR on the plurality of miRNAs, wherein:

(i) when the blocking nucleic acid is a 3' blocking nucleic acid, performing RT-PCR comprises introducing a reverse transcription primer that hybridizes to the adenylated nucleic acid adapter;

(ii) when the blocking nucleic acid is a 5' blocking nucleic acid, the RNA adapter provides a primer binding site for PCR and performing RT-PCR comprises introducing a primer that targets the primer binding site; or (iii) a combination thereof.

2. The method of claim 1, wherein annealing is conducted under stringent conditions.

3. The method of claim 1, wherein annealing is conducted under maximally stringent conditions.

4. The method of claim 1, comprising ligating the blocking nucleic acid to the first end of the unwanted miRNA.

5. The method of claim 1, wherein the first end of the unwanted miRNA is the 5' end and the complementary region is at the 5' end of the blocking nucleic acid.

6. The method of claim 1, wherein the first end of the unwanted miRNA is the 3' end and the complementary region is at the 3' end of the blocking nucleic acid.

7. The method of claim 1, comprising ligating the blocking nucleic acid to the first end of the unwanted miRNA, wherein the ligating step is performed using a DNA/RNA ligase.

8. The method of claim 1, wherein the unwanted miRNA is one or more of: mir-16, mir-15a, mir-15b, mir-195, mir-424, mir-497, mir-486, mir-451, and mir-26.

9. The method of claim 1, wherein an miRNA library with reduced abundance of unwanted miRNA is produced by step (c).

10. The method of claim 1, wherein the blocking nucleic acid is a 5' blocking nucleic acid, the method further comprising introducing the RNA adapter and an RNA ligase under conditions to allow the RNA adapter to ligate to a 5' end of at least one of the plurality of miRNAs prior to step (c).

11. The method of claim 1, wherein the plurality of miRNAs is isolated from a sample from a subject.

12. The method of claim 1, wherein the plurality of miRNAs is obtained from an miRNA library.

13. The method of claim 1, wherein the blocking nucleic acid is one of a plurality of blocking nucleic acids present.

14. The method of claim 1, wherein the blocking nucleic acid comprises one of SEQ ID NOs: 1-4 and 13.

15. The method of claim 1, wherein the first blocking moiety is one or more of: a nucleotide from which the 3' hydroxyl group has been removed, a nucleotide from which the 5' phosphate group has been removed, phosphoramidite, triethylene glycol, hexa-ethyleneglycol, a propyl group, a propanol group, an organic alcohol, a glycol compound, an inverted deoxynucleotide, a dideoxynucleotide, and an inverted dideoxynucleotide.

* * * * *